(12) United States Patent
Alsop et al.

(10) Patent No.: US 8,617,843 B2
(45) Date of Patent: Dec. 31, 2013

(54) RECOMBINANT PEPTIDE PRODUCTION USING A CROSS-LINKABLE SOLUBILITY TAG

(75) Inventors: Albert W. Alsop, Wilmington, DE (US); Qiong Cheng, Wilmington, DE (US); Linda Jane Solomon, Wilmington, DE (US); Stephen R. Fahnestock, Wilmington, DE (US); Tanja Maria Gruber, Media, PA (US); Pierre E. Rouviere, Wilmington, DE (US)

(73) Assignee: E I du Pont de Nemours and Company, Wilmington, DE (US)

( * ) Notice: Subject to any disclaimer, the term of this patent is extended or adjusted under 35 U.S.C. 154(b) by 477 days.

(21) Appl. No.: 13/080,917

(22) Filed: Apr. 6, 2011

(65) Prior Publication Data

US 2011/0183373 A1 Jul. 28, 2011

Related U.S. Application Data

(62) Division of application No. 12/172,395, filed on Jul. 14, 2008, now Pat. No. 7,951,559.

(60) Provisional application No. 60/951,754, filed on Jul. 25, 2007.

(51) Int. Cl.
*C12P 21/06* (2006.01)
*C07K 14/00* (2006.01)

(52) U.S. Cl.
USPC .......................................... 435/69.1; 530/350

(58) Field of Classification Search
USPC .......................................... 435/69.1; 530/350
See application file for complete search history.

(56) References Cited

U.S. PATENT DOCUMENTS

| | | |
|---|---|---|
| 5,206,154 A | 4/1993 | Lai et al. |
| 5,215,896 A | 6/1993 | Keck et al. |
| 5,223,409 A | 6/1993 | Ladner et al. |
| 5,302,526 A | 4/1994 | Keck et al. |
| 5,330,902 A | 7/1994 | Keck et al. |
| 5,403,484 A | 4/1995 | Ladner et al. |
| 5,449,754 A | 9/1995 | Nishioka |
| 5,480,971 A | 1/1996 | Houghten et al. |
| 5,571,698 A | 11/1996 | Ladner et al. |
| 5,585,275 A | 12/1996 | Hudson et al. |
| 5,639,603 A | 6/1997 | Dower et al. |
| 5,643,768 A | 7/1997 | Kawasaki |
| 5,648,244 A | 7/1997 | Kuliopulos et al. |
| 5,658,754 A | 8/1997 | Kawasaki |
| 5,837,500 A | 11/1998 | Ladner et al. |
| 6,037,145 A | 3/2000 | Yabuta et al. |
| 6,207,446 B1 | 3/2001 | Szostak et al. |
| 6,214,553 B1 | 4/2001 | Szostak et al. |
| 6,228,994 B1 | 5/2001 | Yanagawa et al. |
| 6,242,219 B1 | 6/2001 | Better et al. |
| 6,258,558 B1 | 7/2001 | Szostak et al. |
| 6,261,804 B1 | 7/2001 | Szostak et al. |
| 6,281,344 B1 | 8/2001 | Szostak et al. |
| 6,312,927 B1 | 11/2001 | Hammond |
| 6,361,943 B1 | 3/2002 | Yanagawa et al. |
| 6,416,950 B1 | 7/2002 | Lohse et al. |
| 6,429,300 B1 | 8/2002 | Kurz et al. |
| 6,436,665 B1 | 8/2002 | Kuimelis |
| 6,518,018 B1 | 2/2003 | Szostak et al. |
| 6,602,685 B1 | 8/2003 | Lohse |
| 6,613,548 B1 | 9/2003 | Chu |
| 6,620,419 B1 | 9/2003 | Lintner |
| 6,696,089 B2 | 2/2004 | Kabanov et al. |
| 6,815,426 B2 | 11/2004 | Scialdone et al. |
| 6,846,655 B1 | 1/2005 | Wagner et al. |
| 6,924,120 B1 * | 8/2005 | Gan .............................. 435/68.1 |
| 7,074,557 B2 | 7/2006 | Osbourn et al. |
| 7,078,197 B2 | 7/2006 | Kurz et al. |
| 7,220,405 B2 | 5/2007 | Huang et al. |
| 7,276,088 B2 | 10/2007 | Huang et al. |
| 7,285,264 B2 | 10/2007 | O'Brien et al. |
| 7,309,482 B2 | 12/2007 | Buseman-Williams et al. |
| 7,427,656 B2 | 9/2008 | Decarolis et al. |
| 7,452,528 B2 | 11/2008 | Huang et al. |
| 7,632,919 B2 | 12/2009 | Cunningham et al. |
| 7,662,913 B2 | 2/2010 | Decarolis et al. |
| 7,678,883 B2 | 3/2010 | Cheng et al. |

(Continued)

FOREIGN PATENT DOCUMENTS

| | | |
|---|---|---|
| WO | 8807085 | 9/1988 |
| WO | 9404688 | 3/1994 |

(Continued)

OTHER PUBLICATIONS

Kuliopolos et al. 1987; Isolation and sequencing of the gene encoding D5-3-ketosteroid isomerase of *Pseudomonas testosteroni*: Overexpression of the protein. PNAS 84:8893-8897.*
Kemp, D. J., Proc. Natl. Acad. Sci. USA 78(7): 4520-4524 (1981).
Chien et al., Proc. Natl. Acad. Sci. USA 88(21): 9578-82 (1991).
Helfman et al., Proc. Natl. Acad. Sci. USA 80(1):31-35, (1983).
Dykes et al., Eur. J. Biochem., 174:411 (1988).
Schellenberger et al., Int. J. Peptide Protein Res., 41:326 (1993).
Shen et al., Proc. Nat. Acad. Sci. USA 81:4627 (1984).
Kempe et al., Gene, 39:239 (1985).
Ray et al., Bio/Technology, 11:64 (1993).

(Continued)

*Primary Examiner* — Karen Cochrane Carlson

(57) ABSTRACT

The invention relates to the recombinant expression of a peptide of interest in the form of a fusion protein comprising a solubility tag. The fusion protein comprises at least two portions separated by a cleavable peptide sequence wherein one portion is devoid of cysteine residues and the second portion comprises an effective number of cross-linkable cysteine residues. After cell lysis and isolation of the fusion protein, the fusion protein is subsequently cleaved into a mixture of first and second portions. Oxidative cross-linking is used to selectively precipitate one of the two portions to facilitate simple and effective separation of the peptide of interest.

12 Claims, 4 Drawing Sheets

(56) References Cited

U.S. PATENT DOCUMENTS

| | | | |
|---|---|---|---|
| 7,700,716 | B2 | 4/2010 | Cunningham et al. |
| 7,709,601 | B2 | 5/2010 | Cunningham et al. |
| 7,732,569 | B2 | 6/2010 | Decarolis et al. |
| 7,736,633 | B2 | 6/2010 | Beck et al. |
| 7,749,957 | B2 | 7/2010 | Ittel et al. |
| 7,858,581 | B2 | 12/2010 | Cunningham et al. |
| 7,906,617 | B2 | 3/2011 | Cunningham et al. |
| 7,928,076 | B2 | 4/2011 | Cunningham et al. |
| 2002/0098524 | A1 | 7/2002 | Murray et al. |
| 2003/0152976 | A1 | 8/2003 | Janssen et al. |
| 2003/0185870 | A1 | 10/2003 | Grinstaff et al. |
| 2005/0050656 | A1 | 3/2005 | Huang et al. |
| 2005/0054752 | A1 | 3/2005 | O'Brien et al. |
| 2005/0221444 | A1 | 10/2005 | Williams et al. |
| 2005/0226839 | A1 | 10/2005 | Huang et al. |
| 2006/0073111 | A1 | 4/2006 | O'Brien et al. |
| 2006/0199206 | A1 | 9/2006 | Wang et al. |
| 2006/0222609 | A1 | 10/2006 | O'Brien et al. |
| 2008/0280810 | A1 | 11/2008 | O'Brien et al. |

FOREIGN PATENT DOCUMENTS

| | | |
|---|---|---|
| WO | 9830684 | 7/1998 |
| WO | 0006763 | 2/2000 |
| WO | 0179479 | 10/2001 |
| WO | 2004000257 | 12/2003 |
| WO | 2004048399 | 6/2004 |

OTHER PUBLICATIONS

Lai et al., Antimicrob. Agents & Chemo., 37:1614 (1993).
Gram et al., Bio/Technology, 12:1017 (1994).
Kuliopulos et al., J. Am. Chem. Soc. 116:4599-4607 (1994).
Pilon et al., Biotechnol. Prog., 13:374-79 (1997).
Haught et al., Biotechnol. Bioengineer. 57:55-61 (1998).
Aggeli et al., J. Amer. Chem. Soc., 125:9619-9628 (2003).
Aggeli et al., PNAS, 98(21):11857-11862 (2001).
Aggeli et al., Nature, 386-259-262 (1997).
Aggeli et al., J. Mater. Chem., 7(7):1135-1145 (1997).
Lerner and Inouye, Nucleic Acids Research, 18;4631 (1990).
Sulter et al., Arch. Microbiol., 153:485-489 (1990).
Bellion et al., Microb. Growth C1 COMPD., [Int. Symp.], 7TH (1993), 415-32.
Gavit, P. and Better, M., J. Biotechnol., 79:127-136 (2000).
Szoka et al., DNA, 5(1):11-20 (1986).
Thornberry et al., J. Biol. Chem., 272:17907-17911 (1997).
Tyas et al., EMBO Reports, 1(3):266-270 (2000).
Fahnert et al., Advances in Biochemical Engineering, Biotechnology, vol. 89, pp. 93-142 (2004).
Menzella et al., Protein Expression and Purification, vol. 25, No. 2, pp. 248-255 (2002).
International Search Report and Written Opinion of Corresponding PCT Patent Application No. PCT/US2008/070800 Mailed Dec. 30, 2008.
Miller et al., The Journal of Biological Chemistry vol. 255, No. 16, pp. 7521-7524 (1980).

* cited by examiner

SEQUENCE LISTING

<160> NUMBER OF SEQ ID NOS: 224

<210> SEQ ID NO 1
<211> LENGTH: 4945
<212> TYPE: DNA
<213> ORGANISM: artificial sequence
<220> FEATURE:
<223> OTHER INFORMATION: plasmid

<400> SEQUENCE: 1

```
agatctcgat cccgcgaaat taatacgact cactataggg agaccacaac ggtttccctc      60
tagaaataat tttgtttaac tttaagaagg agatatacat atgtcgtact accatcacca     120
tcaccatcac ctcgaatcaa caagtttgta caaaaaagca ggctccgcgg ccgccccctt     180
caccggatcc atcgatccac gtttccacga aaactggccg tctgccggcg gtacctctac     240
ttccaaagct tccaccacta cgacttctag caaaaccacc actacatcct ctaagactac     300
cacgactacc tccaaaacct ctactacctc tagctcctct acgggcggcg ccactcacaa     360
gacctctact cagcgtctgc tggctgcata atgaaagggt gggcgcgccg acccagcttt     420
cttgtacaaa gtggttgatt cgaggctgct aacaaagccc gaaaggaagc tgagttggct     480
gctgccaccg ctgagcaata actagcataa ccccttgggg cctctaaacg ggtcttgagg     540
ggttttttgc tgaaaggagg aactatatcc ggatatccac aggacgggtg tggtcgccat     600
gatcgcgtag tcgatagtgg ctccaagtag cgaagcgagc aggactgggc ggcggccaaa     660
gcggtcggac agtgctccga gaacgggtgc gcatagaaat tgcatcaacg catatagcgc     720
tagcagcacg ccatagtgac tggcgatgct gtcggaatgg acgatatccc gcaagaggcc     780
cggcagtacc ggcataacca agcctatgcc tacagcatcc agggtgacgg tgccgaggat     840
gacgatgagc gcattgttag atttcataca cggtgcctga ctgcgttagc aatttaactg     900
tgataaacta ccgcattaaa gcttatcgat gataagctgt caaacatgag aattcttgaa     960
gacgaaaggg cctcgtgata cgcctatttt tataggttaa tgtcatgata ataatggttt    1020
cttagacgtc aggtggcact tttcggggaa atgtgcgcgg aacccctatt tgtttatttt    1080
tctaaataca ttcaaatatg tatccgctca tgagacaata accctgataa atgcttcaat    1140
aatattgaaa aaggaagagt atgagtattc aacatttccg tgtcgccctt attccctttt    1200
ttgcggcatt ttgccttcct gtttttgctc acccagaaac gctggtgaaa gtaaaagatg    1260
ctgaagatca gttgggtgca cgagtgggtt acatcgaact ggatctcaac agcggtaaga    1320
tccttgagag ttttcgcccc gaagaacgtt ttccaatgat gagcactttt aaagttctgc    1380
tatgtggcgc ggtattatcc cgtgttgacg ccgggcaaga gcaactcggt cgccgcatac    1440
actattctca gaatgacttg gttgagtact caccagtcac agaaaagcat cttacggatg    1500
```

```
gcatgacagt aagagaatta tgcagtgctg ccataaccat gagtgataac actgcggcca   1560
acttacttct gacaacgatc ggaggaccga aggagctaac cgcttttttg cacaacatgg   1620
gggatcatgt aactcgcctt gatcgttggg aaccggagct gaatgaagcc ataccaaacg   1680
acgagcgtga caccacgatg cctgcagcaa tggcaacaac gttgcgcaaa ctattaactg   1740
gcgaactact tactctagct tcccggcaac aattaataga ctggatggag gcggataaag   1800
ttgcaggacc acttctgcgc tcggcccttc cggctggctg gtttattgct gataaatctg   1860
gagccggtga gcgtgggtct cgcggtatca ttgcagcact ggggccagat ggtaagccct   1920
cccgtatcgt agttatctac acgacgggga gtcaggcaac tatggatgaa cgaaatagac   1980
agatcgctga gataggtgcc tcactgatta agcattggta actgtcagac caagtttact   2040
catatatact ttagattgat ttaaaacttc attttttaatt taaaaggatc taggtgaaga   2100
tcctttttga taatctcatg accaaaatcc cttaacgtga gttttcgttc cactgagcgt   2160
cagaccccgt agaaaagatc aaaggatctt cttgagatcc ttttttttctg cgcgtaatct   2220 gctgcttgca aacaaaaaaa ccaccgctac cagcggtggt ttgtttgccg gatcaagagc   2280
taccaactct ttttccgaag gtaactggct tcagcagagc gcagatacca atactgtcc   2340 ttctagtgta gccgtagtta ggccaccact tcaagaactc tgtagcaccg cctacatacc   2400
tcgctctgct aatcctgtta ccagtggctg ctgccagtgg cgataagtcg tgtcttaccg   2460
ggttggactc aagacgatag ttaccggata aggcgcagcg gtcgggctga cggggggtt   2520 cgtgcacaca gcccagcttg gagcgaacga cctacaccga actgagatac ctacagcgtg   2580
agctatgaga aagcgccacg cttcccgaag ggagaaaggc ggacaggtat ccggtaagcg   2640
gcagggtcgg aacaggagag cgcacgaggg agcttccagg gggaaacgcc tggtatcttt   2700
atagtcctgt cgggtttcgc cacctctgac ttgagcgtcg attttttgtga tgctcgtcag   2760 gggggcggag cctatggaaa aacgccagca acgcggcctt tttacggttc ctggccttt   2820 gctggccttt tgctcacatg ttctttcctg cgttatcccc tgattctgtg ataaccgta   2880 ttaccgcctt tgagtgagct gataccgctc gccgcagccg aacgaccgag cgcagcgagt   2940
cagtgagcga ggaagcggaa gagcgcctga tgcggtattt tctccttacg catctgtgcg   3000
gtatttcaca ccgcatatat ggtgcactct cagtacaatc tgctctgatg ccgcatagtt   3060
aagccagtat acactccgct atcgctacgt gactgggtca tggctgcgcc ccgacacccg   3120
ccaacacccg ctgacgcgcc ctgacgggct tgtctgctcc cggcatccgc ttacagacaa   3180
gctgtgaccg tctccgggag ctgcatgtgt cagaggtttt caccgtcatc accgaaacgc   3240
gcgaggcagc tgcggtaaag ctcatcagcg tggtcgtgaa gcgattcaca gatgtctgcc   3300
tgttcatccg cgtccagctc gttgagtttc tccagaagcg ttaatgtctg gcttctgata   3360
aagcgggcca tgttaagggc ggttttttcc tgtttggtca ctgatgcctc cgtgtaaggg   3420
ggatttctgt tcatgggggt aatgataccg atgaaacgag agaggatgct cacgatacgg   3480
gttactgatg atgaacatgc ccggttactg gaacgttgtg agggtaaaca actggcggta   3540
tggatgcggc gggaccagag aaaaatcact cagggtcaat gccagcgctt cgttaataca   3600
gatgtaggtg ttccacaggg tagccagcag catcctgcga tgcagatccg gaacataatg   3660
gtgcagggcg ctgacttccg cgtttccaga ctttacgaaa cacggaaacc gaagaccatt   3720
catgttgttg ctcaggtcgc agacgttttg cagcagcagt cgcttcacgt tcgctcgcgt   3780
atcggtgatt cattctgcta accagtaagg caaccccgcc agcctagccg ggtcctcaac   3840
gacaggagca cgatcatgcg cacccgtggc caggacccaa cgctgcccga gatgcgccgc   3900
```

```
gtgcggctgc tggagatggc ggacgcgatg gatatgttct gccaagggtt ggtttgcgca    3960
ttcacagttc tccgcaagaa ttgattggct ccaattcttg gagtggtgaa tccgttagcg    4020
aggtgccgcc ggcttccatt caggtcgagg tggcccggct ccatgcaccg cgacgcaacg    4080
cggggaggca gacaaggtat agggcggcgc ctacaatcca tgccaacccg ttccatgtgc    4140
tcgccgaggc ggcataaatc gccgtgacga tcagcggtcc agtgatcgaa gttaggctgg    4200
taagagccgc gagcgatcct tgaagctgtc cctgatggtc gtcatctacc tgcctggaca    4260
gcatggcctg caacgcgggc atcccgatgc cgccggaagc gagaagaatc ataatgggga    4320
aggccatcca gcctcgcgtc gcgaacgcca gcaagacgta gcccagcgcg tcggccgcca    4380
tgccggcgat aatggcctgc ttctcgccga aacgtttggt ggcgggacca gtgacgaagg    4440
cttgagcgag ggcgtgcaag attccgaata ccgcaagcga caggccgatc atcgtcgcgc    4500
tccagcgaaa gcggtcctcg ccgaaaatga cccagagcgc tgccggcacc tgtcctacga    4560
gttgcatgat aaagaagaca gtcataagtg cggcgacgat agtcatgccc cgcgcccacc    4620
ggaaggagct gactgggttg aaggctctca agggcatcgg tcgatcgacg ctctccctta    4680
tgcgactcct gcattaggaa gcagcccagt agtaggttga ggccgttgag caccgccgcc    4740
gcaaggaatg gtgcatgcaa ggagatggcg cccaacagtc ccccggccac ggggcctgcc    4800
accatcccca cgccgaaaca agcgctcatg agcccgaagt ggcgagcccg atcttcccca    4860
tcggtgatgt cggcgatata ggcgccagca accgcacctg tggcgccggt gatgccggcc    4920
acgatgcgtc cggcgtagag gatcg                                          4945
```

<210> SEQ ID NO 2  
<211> LENGTH: 5388  
<212> TYPE: DNA  
<213> ORGANISM: artificial sequence  
<220> FEATURE:  
<223> OTHER INFORMATION: plasmid

<400> SEQUENCE: 2

```
agatctcgat cccgcgaaat taatacgact cactataggg agaccacaac ggtttccctc      60
tagaaataat tttgtttaac tttaagaagg agatatacat atgcataccc cagaacacat     120
caccgccgtg gtacagcgct tgtggctgc gctcaatgcc ggcgatctgg acggcatcgt     180
cgcgctgttt gccgatgacg ccacggtgga agagcccgtg ggttccgagc caggtccgg     240 tacggctgcg tgtcgtgagt tttacgccaa ctcgctcaaa ctgcctttgg cggtggagct     300
gacgcaggag tgccgcgcgg tcgccaacga agcggccttc gctttcaccg tcagcttcga     360
gtatcagggc cgcaagaccg tagttgcgcc ctgtgatcac tttcgcttca atggcgccgg     420
caaggtggtg agcatccgcg ccttgtttgg cgagaagaat attcacgcat gccagggatc     480
cgatccgact ccgccgacga atgtactgat gctggcaacc aaaggcggtg gtacgcattc     540
cacgcacaac catggcagcc cgcgccacac gaatgctgac gcaggcaatc cgggcggcgg     600
caccccacca accaatgtcc tgatgctggc tactaaaggc ggcggcacgc attctaccca     660
caaccatggt agcccgcgcc atactaatgc agatgccgga aacccgggcg gtggtacccc     720
gccaaccaac gttctgatgc tggcgacgaa aggtggcggt acccattcca cgcataatca     780
tggcagccct cgccacacca acgctgatgc tggtaatcct ggtggcggta agaagaaata     840
ataaggcgcg ccgacccagc tttcttgtac aaagtggttg attcgaggct gctaacaaag     900
cccgaaagga agctgagttg gctgctgcca ccgctgagca ataactagca taaccccttg     960
gggcctctaa acgggtcttg aggggttttt tgctgaaagg aggaactata tccggatatc    1020
```

```
cacaggacgg gtgtggtcgc catgatcgcg tagtcgatag tggctccaag tagcgaagcg    1080
agcaggactg ggcggcggcc aaagcggtcg gacagtgctc cgagaacggg tgcgcataga    1140
aattgcatca acgcatatag cgctagcagc acgccatagt gactggcgat gctgtcggaa    1200
tggacgatat cccgcaagag gcccggcagt accggcataa ccaagcctat gcctacagca    1260
tccagggtga cggtgccgag gatgacgatg agcgcattgt tagatttcat acacggtgcc    1320
tgactgcgtt agcaatttaa ctgtgataaa ctaccgcatt aaagcttatc gatgataagc    1380
tgtcaaacat gagaattctt gaagacgaaa gggcctcgtg atacgcctat ttttataggt    1440
taatgtcatg ataataatgg tttcttagac gtcaggtggc acttttcggg gaaatgtgcg    1500
cggaacccct atttgtttat ttttctaaat acattcaaat atgtatccgc tcatgagaca    1560
ataaccctga taaatgcttc aataatattg aaaaaggaag agtatgagta ttcaacattt    1620
ccgtgtcgcc cttattccct ttttgcggc attttgcctt cctgttttg ctcacccaga    1680 aacgctggtg aaagtaaaag atgctgaaga tcagttgggt gcacgagtgg gttacatcga    1740
actggatctc aacagcggta agatccttga gagttttcgc cccgaagaac gttttccaat    1800
gatgagcact tttaaagttc tgctatgtgg cgcggtatta tcccgtgttg acgccgggca    1860
agagcaactc ggtcgccgca tacactattc tcagaatgac ttggttgagt actcaccagt    1920
cacagaaaag catcttacgg atggcatgac agtaagagaa ttatgcagtg ctgccataac    1980
catgagtgat aacactgcgg ccaacttact tctgacaacg atcggaggac cgaaggagct    2040
aaccgctttt ttgcacaaca tgggggatca tgtaactcgc cttgatcgtt gggaaccgga    2100
gctgaatgaa gccataccaa acgacgagcg tgacaccacg atgcctgcag caatggcaac    2160
aacgttgcgc aaactattaa ctggcgaact acttactcta gcttcccggc aacaattaat    2220
agactggatg gaggcggata agttgcagg accacttctg cgctcggccc ttccggctgg    2280
ctggtttatt gctgataaat ctggagccgg tgagcgtggg tctcgcggta tcattgcagc    2340
actggggcca gatggtaagc cctcccgtat cgtagttatc tacacgacgg ggagtcaggc    2400
aactatggat gaacgaaata gacagatcgc tgagataggt gcctcactga ttaagcattg    2460
gtaactgtca gaccaagttt actcatatat actttagatt gatttaaaac ttcatttta    2520 atttaaaagg atctaggtga agatcctttt tgataatctc atgaccaaaa tcccttaacg    2580
tgagttttcg ttccactgag cgtcagaccc cgtagaaaag atcaaaggat cttcttgaga    2640 tcctttttt ctgcgcgtaa tctgctgctt gcaaacaaaa aaaccaccgc taccagcggt    2700
ggtttgtttg ccggatcaag agctaccaac tctttttccg aaggtaactg gcttcagcag    2760
agcgcagata ccaaatactg tccttctagt gtagccgtag ttaggccacc acttcaagaa    2820
ctctgtagca ccgcctacat acctcgctct gctaatcctg ttaccagtgg ctgctgccag    2880
tggcgataag tcgtgtctta ccgggttgga ctcaagacga tagttaccgg ataaggcgca    2940
gcggtcgggc tgaacggggg gttcgtgcac acagcccagc ttggagcgaa cgacctacac    3000
cgaactgaga tacctacagc gtgagctatg agaaagcgcc acgcttcccg aagggagaaa    3060
ggcggacagg tatccggtaa gcggcagggt cggaacagga gagcgcacga gggagcttcc    3120
agggggaaac gcctggtatc tttatagtcc tgtcgggttt cgccacctct gacttgagcg    3180
tcgatttttg tgatgctcgt caggggggcg gagcctatgg aaaaacgcca gcaacgcggc    3240 cttttacgg ttcctggcct tttgctggcc ttttgctcac atgttctttc ctgcgttatc    3300
ccctgattct gtggataacc gtattaccgc ctttgagtga gctgataccg ctcgccgcag    3360
ccgaacgacc gagcgcagcg agtcagtgag cgaggaagcg gaagagcgcc tgatgcggta    3420
```

```
ttttctcctt acgcatctgt gcggtatttc acaccgcata tatggtgcac tctcagtaca    3480
atctgctctg atgccgcata gttaagccag tatacactcc gctatcgcta cgtgactggg    3540
tcatggctgc gccccgacac ccgccaacac ccgctgacgc gccctgacgg gcttgtctgc    3600
tcccggcatc cgcttacaga caagctgtga ccgtctccgg gagctgcatg tgtcagaggt    3660
tttcaccgtc atcaccgaaa cgcgcgaggc agctgcggta agctcatca gcgtggtcgt    3720 gaagcgattc acagatgtct gcctgttcat ccgcgtccag ctcgttgagt ttctccagaa    3780
gcgttaatgt ctggcttctg ataaagcggg ccatgttaag gcggttttt tcctgtttgg    3840 tcactgatgc ctccgtgtaa gggggatttc tgttcatggg ggtaatgata ccgatgaaac    3900
gagagaggat gctcacgata cgggttactg atgatgaaca tgcccggtta ctggaacgtt    3960
gtgagggtaa acaactggcg gtatggatgc ggcgggacca gagaaaaatc actcagggtc    4020
aatgccagcg cttcgttaat acagatgtag gtgttccaca gggtagccag cagcatcctg    4080
cgatgcagat ccggaacata atggtgcagg cgctgactt ccgcgtttcc agactttacg    4140
aaacacggaa accgaagacc attcatgttg ttgctcaggt cgcagacgtt ttgcagcagc    4200
agtcgcttca cgttcgctcg cgtatcgtg attcattctg ctaaccagta aggcaacccc    4260
gccagcctag ccgggtcctc aacgacagga gcacgatcat gcgcacccgt ggccaggacc    4320
caacgctgcc cgagatgcgc cgcgtgcggc tgctggagat ggcggacgcg atggatatgt    4380
tctgccaagg gttggtttgc gcattcacag ttctccgcaa gaattgattg ctccaattc    4440 ttggagtggt gaatccgtta gcgaggtgcc gccggcttcc attcaggtcg aggtggcccg    4500
gctccatgca ccgcgacgca acgcggggag gcagacaagg tatagggcgg cgcctacaat    4560
ccatgccaac ccgttccatg tgctcgccga ggcggcataa atcgccgtga cgatcagcgg    4620
tccagtgatc gaagttaggc tggtaagagc cgcgagcgat ccttgaagct gtccctgatg    4680
gtcgtcatct acctgcctgg acagcatggc ctgcaacgcg gcatcccga tgccgccgga    4740 agcgagaaga atcataatgg ggaaggccat ccagcctcgc gtcgcgaacg ccagcaagac    4800
gtagcccagc gcgtcggccg ccatgccggc gataatggcc tgcttctcgc cgaaacgttt    4860
ggtggcggga ccagtgacga aggcttgagc gagggcgtgc aagattccga ataccgcaag    4920
cgacaggccg atcatcgtcg cgctccagcg aaagcggtcc tcgccgaaaa tgacccagag    4980
cgctgccggc acctgtccta cgagttgcat gataaagaag acagtcataa gtgcggcgac    5040
gatagtcatg ccccgcgccc accggaagga gctgactggg ttgaaggctc tcaagggcat    5100
cggtcgatcg acgctctccc ttatgcgact cctgcattag gaagcagccc agtagtaggt    5160
tgaggccgtt gagcaccgcc gccgcaagga atggtgcatg caaggagatg cgcccaaca    5220 gtccccggc cacgggcct gccaccatac ccacgccgaa acaagcgctc atgagcccga    5280
agtggcgagc ccgatcttcc ccatcggtga tgtcggcgat ataggcgcca gcaaccgcac    5340
ctgtggcgcc ggtgatgccg gccacgatgc gtccggcgta gaggatcg                5388
```

```
<210> SEQ ID NO 3
<211> LENGTH: 6199
<212> TYPE: DNA
<213> ORGANISM: artificial sequence
<220> FEATURE:
<223> OTHER INFORMATION: plasmid

<400> SEQUENCE: 3
aagaaaccaa ttgtccatat tgcatcagac attgccgtca ctgcgtcttt tactggctct      60
tctcgctaac caaaccggta accccgctta ttaaaagcat tctgtaacaa agcgggacca     120
```

```
aagccatgac aaaaacgcgt aacaaaagtg tctataatca cggcagaaaa gtccacattg    180
attatttgca cggcgtcaca ctttgctatg ccatagcatt tttatccata agattagcgg    240
atcttacctg acgcttttta tcgcaactct ctactgtttc tccatacccg ttttttgggc    300
taacaggagg aattacatat gcatacccca gaacacatca ccgccgtggt acagcgcttt    360
gtggctgcgc tcaatgccgg cgatctggac ggcatcgtcg cgctgtttgc cgatgacgcc    420
acggtggaag agcccgtggg ttccgagccc aggtccggta cggctgcgtg tcgtgagttt    480
tacgccaact cgctcaaact gccttttggcg gtggagctga cgcaggagtg ccgcgcggtc    540
gccaacgaag cggccttcgc tttcaccgtc agcttcgagt atcagggccg caagaccgta    600
gttgcgccct gtgatcactt tcgcttcaat ggcgccggca aggtggtgag catccgcgcc    660
ttgtttggcg agaagaatat tcacgcatgc cagggatccg atccgactcc gccgacgaat    720
gtactgatgc tggcaaccaa aggcggtggt acgcattcca cgcacaacca tggcagcccg    780
cgccacacga atgctgacgc aggcaatccg ggcggcggca ccccaccaac caatgtcctg    840
atgctggcta ctaaaggcgg cggcacgcat tctacccaca accatggtag cccgcgccat    900
actaatgcag atgccggcaa cccgggcggt ggtaccccgc caaccaacgt tctgatgctg    960
gcgacgaaag gtggcggtac ccattccacg cataatcatg gcagccctcg ccacaccaac   1020
gctgatgctg gtaatcctgg tggcggtaag aagaaataat aaggcgcgcc gacccagctt   1080
tcttgtacaa agtggttgat tcgaggctgc taacaaagcc cgaaaggaag ctgagttggc   1140
tgctgccacc gctgagcaat aactagcata accccttggg gcctctaaac gggtcttgag   1200
gggttttttg ctgaaaggag gaactatatc cggatatcca caggacgggt gtggtcgcca   1260
tgatcgcgta gtcgatagtg gctccaagta gcgaagcgag caggactggg cggcggccaa   1320
agcggtcgga cagtgctccg agaacgggtg cgcatagaaa ttgcatcaac gcatatagcg   1380
ctagcagcac gccatagtga ctggcgatgc tgtcggaatg gacgatatcc cgcaagaggc   1440
ccggcagtac cggcataacc aagcctatgc ctacagcatc cagggtgacg gtgccgagga   1500
tgacgatgag cgcattgtta gatttcatac acggtgcctg actgcgttag caatttaact   1560
gtgataaact accgcattaa agcttgcagt ggcggttttc atggcttgtt atgactgttt   1620
ttttggggta cagtctatgc ctcgggcatc caagcagcaa gcgcgttacg ccgtgggtcg   1680
atgtttgatg ttatggagca gcaacgatgt tacgcagcag ggcagtcgcc ctaaaacaaa   1740
gttaaacatc atgagggaag cggtgatcgc cgaagtatcg actcaactat cagaggtagt   1800
tggcgtcatc gagcgccatc tcgaaccgac gttgctggcc gtacatttgt acggctccgc   1860
agtggatggc ggcctgaagc cacacagtga tattgatttg ctggttacgg tgaccgtaag   1920
gcttgatgaa acaacgcggc gagctttgat caacgacctt ttggaaactt cggcttcccc   1980
tggagagagc gagattctcc gcgctgtaga agtcaccatt gttgtgcacg acgacatcat   2040
tccgtggcgt tatccagcta agcgcgaact gcaatttgga gaatggcagc gcaatgacat   2100
tcttgcaggt atcttcgagc cagccacgat cgacattgat ctggctatct tgctgacaaa   2160
agcaagagaa catagcgttg ccttggtagg tccagcggcg gaggaactct ttgatccggt   2220
tcctgaacag gatctatttg aggcgctaaa tgaaacctta acgctatgga actcgccgcc   2280
cgactgggct ggcgatgagc gaaatgtagt gcttacgttg tcccgcattt ggtacagcgc   2340
agtaaccggc aaaatcgcgc cgaaggatgt cgctgccgac tgggcaatgg agcgcctgcc   2400
ggcccagtat cagcccgtca tacttgaagc tagacaggct tatcttggac aagaagaaga   2460
tcgcttggcc tcgcgcgcag atcagttgga agaatttgtc cactacgtga aaggcgagat   2520
```

```
caccaaggta gtcggcaaat aatgtctaac aattcgttca agcttggctg ttttggcgga    2580
tgagagaaga ttttcagcct gatacagatt aaatcagaac gcagaagcgg tctgataaaa    2640
cagaatttgc ctggcggcag tagcgcggtg gtcccacctg accccatgcc gaactcagaa    2700
gtgaaacgcc gtagcgccga tggtagtgtg gggtctcccc atgcgagagt agggaactgc    2760
caggcatcaa ataaaacgaa aggctcagtc gaaagactgg gcctttcgtt ttatctgttg    2820
tttgtcggtg aacgctctcc tgagtaggac aaatccgccg ggagcggatt tgaacgttgc    2880
gaagcaacgg cccggagggt ggcgggcagg acgcccgcca taaactgcca ggcatcaaat    2940
taagcagaag gccatcctga cggatggcct ttttgcgttt ctacaaactc ttttgtttat    3000
ttttctaaat acattcaaat atgtatccgc tcatgagaca ataaccctga taaatgcttc    3060
aataatattg aaaaaggaag agtatgagta ttcaacattt ccgtgtcgcc cttattccct    3120
tttttgcggc attttgcctt cctgtttttg ctcacccaga aacgctggtg aaagtaaaag    3180
atgctgaaga tcagttgggt gcacgagtgg gttacatcga actggatctc aacagcggta    3240
agatccttga gagttttcgc cccgaagaac gttttccaat gatgagcact tttaaagttc    3300
tgctatgtgg cgcggtatta tcccgtgttg acgccgggca agagcaactc ggtcgccgca    3360
tacactattc tcagaatgac ttggttgagt actcaccagt cacagaaaag catcttacgg    3420
atggcatgac agtaagagaa ttatgcagtg ctgccataac catgagtgat aacactgcgg    3480
ccaacttact tctgacaacg atcggaggac cgaaggagct aaccgctttt ttgcacaaca    3540
tgggggatca tgtaactcgc cttgatcgtt gggaaccgga gctgaatgaa gccataccaa    3600
acgacgagcg tgacaccacg atgcctgtag caatggcaac aacgttgcgc aaactattaa    3660
ctggcgaact acttactcta gcttcccggc aacaattaat agactggatg gaggcggata    3720
aagttgcagg accacttctg cgctcggccc ttccggctgg ctggtttatt gctgataaat    3780
ctggagccgg tgagcgtggg tctcgcggta tcattgcagc actggggcca gatggtaagc    3840
cctcccgtat cgtagttatc tacacgacgg ggagtcaggc aactatggat gaacgaaata    3900
gacagatcgc tgagataggt gcctcactga ttaagcattg gtaactgtca gaccaagttt    3960
actcatatat actttagatt gatttaaaac ttcatttta atttaaaagg atctaggtga    4020
agatcctttt tgataatctc atgaccaaaa tcccttaacg tgagttttcg ttccactgag    4080
cgtcagaccc cgtagaaaag atcaaaggat cttcttgaga tcctttttt ctgcgcgtaa    4140 tctgctgctt gcaaacaaaa aaaccaccgc taccagcggt ggtttgtttg ccggatcaag    4200
agctaccaac tctttttccg aaggtaactg gcttcagcag agcgcagata ccaaatactg    4260
tccttctagt gtagccgtag ttaggccacc acttcaagaa ctctgtagca ccgcctacat    4320
acctcgctct gctaatcctg ttaccagtgg ctgctgccag tggcgataag tcgtgtctta    4380
ccgggttgga ctcaagacga tagttaccgg ataaggcgca gcggtcgggc tgaacggggg    4440
gttcgtgcac acagcccagc ttggagcgaa cgacctacac cgaactgaga tacctacagc    4500
gtgagctatg agaaagcgcc acgcttcccg aagggagaaa ggcggacagg tatccggtaa    4560
gcggcagggt cggaacagga gagcgcacga gggagcttcc agggggaaac gcctggtatc    4620
tttatagtcc tgtcgggttt cgccacctct gacttgagcg tcgatttttg tgatgctcgt    4680
caggggggcg gagcctatgg aaaaacgcca gcaacgcggc ctttttacgg ttcctggcct    4740
tttgctggcc ttttgctcac atgttctttc ctgcgttatc ccctgattct gtggataacc    4800
gtattaccgc ctttgagtga gctgataccg ctcgccgcag ccgaacgacc gagcgcagcg    4860
agtcagtgag cgaggaagcg gaagagcgcc tgatgcggta ttttctcctt acgcatctgt    4920
```

```
gcggtatttc acaccgcata tatggtgcac tctcagtaca atctgctctg atgccgcata    4980
gttaagccag tatacactcc gctatcgcta cgtgactggg tcatggctgc gccccgacac    5040
ccgccaacac ccgctgacgc gccctgacgg gcttgtctgc tcccggcatc cgcttacaga    5100
caagctgtga ccgtctccgg gagctgcatg tgtcagaggt tttcaccgtc atcaccgaaa    5160
cgcgcgaggc agcagatcaa ttcgcgcgcg aaggcgaagc ggcatgcata atgtgcctgt    5220
caaatggacg aagcagggat tctgcaaacc ctatgctact ccgtcaagcc gtcaattgtc    5280
tgattcgtta ccaattatga caacttgacg gctacatcat tcactttttc ttcacaaccg    5340
gcacggaact cgctcgggct ggccccggtg catttttttaa atacccgcga gaaatagagt    5400
tgatcgtcaa aaccaacatt gcgaccgacg gtggcgatag gcatccgggt ggtgctcaaa    5460
agcagcttcg cctggctgat acgttggtcc tcgcgccagc ttaagacgct aatccctaac    5520
tgctggcgga aaagatgtga cagacgcgac ggcgacaagc aaacatgctg tgcgacgctg    5580
gcgatatcaa aattgctgtc tgccaggtga tcgctgatgt actgacaagc ctcgcgtacc    5640
cgattatcca tcggtggatg gagcgactcg ttaatcgctt ccatgcgccg cagtaacaat    5700
tgctcaagca gatttatcgc cagcagctcc gaatagcgcc cttcccttg cccggcgtta     5760 atgatttgcc caaacaggtc gctgaaatgc ggctggtgcg cttcatccgg gcgaaagaac    5820
cccgtattgg caaatattga cggccagtta agccattcat gccagtaggc gcgcggacga    5880
aagtaaaccc actggtgata ccattcgcga gcctccggat gacgaccgta gtgatgaatc    5940
tctcctggcg ggaacagcaa atatcaccc ggtcggcaaa caaattctcg tccctgattt     6000
ttcaccaccc cctgaccgcg aatggtgaga ttgagaatat aacctttcat tcccagcggt    6060
cggtcgataa aaaaatcgag ataaccgttg gcctcaatcg gcgttaaacc cgccaccaga    6120
tgggcattaa acgagtatcc cggcagcagg ggatcatttt gcgcttcagc catacttttc    6180
atactcccgc cattcagag                                                 6199

<210> SEQ ID NO 4
<211> LENGTH: 6010
<212> TYPE: DNA
<213> ORGANISM: artificial sequence
<220> FEATURE:
<223> OTHER INFORMATION: plasmid

<400> SEQUENCE: 4
aagaaaccaa ttgtccatat tgcatcagac attgccgtca ctgcgtcttt tactggctct      60
tctcgctaac caaaccggta accccgctta ttaaaagcat tctgtaacaa agcgggacca     120
aagccatgac aaaaacgcgt aacaaaagtg tctataatca cggcagaaaa gtccacattg     180
attatttgca cggcgtcaca ctttgctatg ccatagcatt tttatccata agattagcgg     240
atcttacctg acgcttttta tcgcaactct ctactgtttc tccataccg tttttgggc       300 taacaggagg aattacatat gcagcagcgt ttccagtgg agttcgaaca gcagccgcgt      360
ggtcagcagc gtttccagtg gcagttcgaa cagcagccgc gtggtcagca gcgtttccag    420
tggcagttcg aacagcagcc ggaaggtcag cagcgtttcc agtggcagtt cgaacagcag    480
ggatccgacc ctggcattcc gtggtggaac attcgtgctc ctctgaatgc aggtgcgggc    540
atcccttggt ggaatattcg tgctccgctg aacgccggtg gttccggtcc gggtagcggt    600
ggtaatactt ctcagctgtc cacgggtggc ggtaacacta gccagctgag cacgggcggc    660
cctaaaaagc cggcgaccc gggtattccg tggtggaata tccgtgcccc gctgaacgca     720
ggtgccggca tcccgtggtg gaacattcgt gcacctctga atgctggtgg ttccggtcca    780
```

-continued

```
ggctctggcg gcaacacttc ccagctgtcc accggcggtg gcaacaccag ccagctgtct    840
actggtggtc cgaagaaacc gggtgactaa taaggcgcgc cgacccagct ttcttgtaca    900
aagtggttga ttcgaggctg ctaacaaagc ccgaaaggaa gctgagttgg ctgctgccac    960
cgctgagcaa taactagcat aaccccttgg ggcctctaaa cgggtcttga ggggttttt    1020
gctgaaagga ggaactatat ccggatatcc acaggacggg tgtggtcgcc atgatcgcgt   1080
agtcgatagt ggctccaagt agcgaagcga gcaggactgg gcggcggcca aagcggtcgg   1140
acagtgctcc gagaacgggt gcgcatagaa attgcatcaa cgcatatagc gctagcagca   1200
cgccatagtg actggcgatg ctgtcggaat ggacgatatc ccgcaagagg cccggcagta   1260
ccggcataac caagcctatg cctacagcat ccagggtgac ggtgccgagg atgacgatga   1320
gcgcattgtt agatttcata cacggtgcct gactgcgtta gcaatttaac tgtgataaac   1380
taccgcatta agcttgcag tggcggtttt catggcttgt tatgactgtt ttttggggt    1440
acagtctatg cctcgggcat ccaagcagca agcgcgttac gccgtgggtc gatgtttgat   1500
gttatggagc agcaacgatg ttacgcagca gggcagtcgc cctaaaacaa agttaaacat   1560
catgagggaa gcggtgatcg ccgaagtatc gactcaacta tcagaggtag ttggcgtcat   1620
cgagcgccat ctcgaaccga cgttgctggc cgtacatttg tacggctccg cagtggatgg   1680
cggcctgaag ccacacagtg atattgattt gctggttacg gtgaccgtaa ggcttgatga   1740
aacaacgcgg cgagctttga tcaacgacct tttggaaact tcggcttccc ctggagagag   1800
cgagattctc cgcgctgtag aagtcaccat tgttgtgcac gacgcatca ttccgtggcg    1860
ttatccagct aagcgcgaac tgcaatttgg agaatggcag cgcaatgaca ttcttgcagg   1920
tatcttcgag ccagccacga tcgacattga tctggctatc ttgctgacaa agcaagaga    1980
acatagcgtt gccttggtag gtccagcggc ggaggaactc tttgatccgg ttcctgaaca   2040
ggatctattt gaggcgctaa atgaaacctt aacgctatgg aactcgccgc ccgactgggc   2100
tggcgatgag cgaaatgtag tgcttacgtt gtcccgcatt tggtacagcg cagtaaccgg   2160
caaaatcgcg ccgaaggatg tcgctgccga ctgggcaatg gagcgcctgc cggcccagta   2220
tcagcccgtc atacttgaag ctagacaggc ttatcttgga caagaagaag atcgcttggc   2280
ctcgcgcgca gatcagttgg aagaatttgt ccactacgtg aaaggcgaga tcaccaaggt   2340
agtcggcaaa taatgtctaa caattcgttc aagcttggct gttttggcgg atgagagaag   2400
attttcagcc tgatacagat taaatcgaa cgcagaagcg gtctgataaa acagaatttg    2460
cctggcggca gtagcgcggt ggtcccacct gaccccatgc cgaactcaga agtgaaacgc   2520
cgtagcgccg atggtagtgt ggggtctccc catgcgagag tagggaactg ccaggcatca   2580
aataaaacga aggctcagt cgaaagactg ggcctttcgt tttatctgtt gtttgtcggt    2640
gaacgctctc ctgagtagga caaatccgcc gggagcggat ttgaacgttg cgaagcaacg   2700
gcccggaggg tggcgggcag gacgcccgcc ataaactgcc aggcatcaaa ttaagcagaa   2760
ggccatcctg acggatggcc ttttttgcgtt tctacaaact cttttgttta ttttttctaaa 2820
tacattcaaa tatgtatccg ctcatgagac aataaccctg ataaatgctt caataatatt   2880
gaaaaggaa gagtatgagt attcaacatt tccgtgtcgc ccttattccc ttttttgcgg    2940
cattttgcct tcctgttttt gctcacccag aaacgctggg gaaagtaaaa gatgctgaag   3000
atcagttggg tgcacgagtg ggttacatcg aactggatct caacagcggt aagatccttg   3060
agagttttcg ccccgaagaa cgttttccaa tgatgagcac ttttaaagtt ctgctatgtg   3120
gcgcggtatt atcccgtgtt gacgccgggc aagagcaact cggtcgccgc atacactatt   3180
```

```
ctcagaatga cttggttgag tactcaccag tcacagaaaa gcatcttacg gatggcatga    3240
cagtaagaga attatgcagt gctgccataa ccatgagtga taacactgcg gccaacttac    3300
ttctgacaac gatcggagga ccgaaggagc taaccgcttt tttgcacaac atgggggatc    3360
atgtaactcg ccttgatcgt tgggaaccgg agctgaatga agccatacca aacgacgagc    3420
gtgacaccac gatgcctgta gcaatggcaa caacgttgcg caaactatta actggcgaac    3480
tacttactct agcttcccgg caacaattaa tagactggat ggaggcggat aaagttgcag    3540
gaccacttct gcgctcggcc cttccggctg gctggtttat tgctgataaa tctggagccg    3600
gtgagcgtgg gtctcgcggt atcattgcag cactggggcc agatggtaag ccctcccgta    3660
tcgtagttat ctacacgacg gggagtcagg caactatgga tgaacgaaat agacagatcg    3720
ctgagatagg tgcctcactg attaagcatt ggtaactgtc agaccaagtt tactcatata    3780
tactttagat tgatttaaaa cttcatttt aatttaaaag gatctaggtg aagatccttt    3840
ttgataatct catgaccaaa atcccttaac gtgagttttc gttccactga gcgtcagacc    3900
ccgtagaaaa gatcaaagga tcttcttgag atcctttttt tctgcgcgta atctgctgct    3960
tgcaaacaaa aaaaccaccg ctaccagcgg tggtttgttt gccggatcaa gagctaccaa    4020 ctcttttcc gaaggtaact ggcttcagca gagcgcagat accaaatact gtccttctag    4080
tgtagccgta gttaggccac cacttcaaga actctgtagc accgcctaca tacctcgctc    4140
tgctaatcct gttaccagtg gctgctgcca gtggcgataa gtcgtgtctt accgggttgg    4200
actcaagacg atagttaccg gataaggcgc agcggtcggg ctgaacgggg ggttcgtgca    4260
cacagcccag cttggagcga acgacctaca ccgaactgag atacctacag cgtgagctat    4320
gagaaagcgc cacgcttccc gaagggagaa aggcggacag gtatccggta agcggcaggg    4380
tcggaacagg agagcgcacg agggagcttc caggggggaaa cgcctggtat ctttatagtc    4440
ctgtcgggtt tcgccacctc tgacttgagc gtcgattttt gtgatgctcg tcagggggggc    4500 ggagcctatg gaaaaacgcc agcaacgcgg cctttttacg gttcctggcc ttttgctggc    4560
cttttgctca catgttcttt cctgcgttat ccctgattc tgtggataac cgtattaccg    4620
cctttgagtg agctgatacc gctcgccgca gccgaacgac cgagcgcagc gagtcagtga    4680
gcgaggaagc ggaagagcgc ctgatgcggt attttctcct tacgcatctg tgcggtattt    4740
cacaccgcat atatggtgca ctctcagtac aatctgctct gatgccgcat agttaagcca    4800
gtatacactc cgctatcgct acgtgactgg gtcatggctg cgccccgaca cccgccaaca    4860
cccgctgacg cgccctgacg ggcttgtctg ctcccggcat ccgcttacag acaagctgtg    4920
accgtctccg ggagctgcat gtgtcagagg ttttcaccgt catcaccgaa acgcgcgagg    4980
cagcagatca attcgcgcgc gaaggcgaag cggcatgcat aatgtgcctg tcaaatggac    5040
gaagcaggga ttctgcaaac cctatgctac tccgtcaagc cgtcaattgt ctgattcgtt    5100
accaattatg acaacttgac ggctacatca ttcactttt cttcacaacc ggcacggaac    5160
tcgctcgggc tggccccggt gcatttttta aatacccgcg agaaatagag ttgatcgtca    5220
aaaccaacat tgcgaccgac ggtggcgata ggcatccggg tggtgctcaa aagcagcttc    5280
gcctggctga tacgttggtc ctcgcgccag cttaagacgc taatccctaa ctgctggcgg    5340
aaaagatgtg acagacgcga cggcgacaag caaacatgct gtgcgacgct ggcgatatca    5400
aaattgctgt ctgccaggtg atcgctgatg tactgacaag cctcgcgtac ccgattatcc    5460
atcggtggat ggagcgactc gttaatcgct tccatcgccc gcagtaacaa ttgctcaagc    5520
agatttatcg ccagcagctc cgaatagcgc ccttcccctt gcccggcgtt aatgatttgc    5580
```

-continued

```
ccaaacaggt cgctgaaatg cggctggtgc gcttcatccg ggcgaaagaa ccccgtattg    5640
gcaaatattg acggccagtt aagccattca tgccagtagg cgcgcggacg aaagtaaacc    5700
cactggtgat accattcgcg agcctccgga tgacgaccgt agtgatgaat ctctcctggc    5760
gggaacagca aaatatcacc cggtcggcaa acaaattctc gtccctgatt tttcaccacc    5820
ccctgaccgc gaatggtgag attgagaata taccctttca ttcccagcgg tcggtcgata    5880
aaaaaatcga gataaccgtt ggcctcaatc ggcgttaaac ccgccaccag atgggcatta    5940
aacgagtatc ccggcagcag gggatcattt tgcgcttcag ccatactttt catactcccg    6000
ccattcagag                                                          6010
```

<210> SEQ ID NO 5
<211> LENGTH: 384
<212> TYPE: DNA
<213> ORGANISM: artificial sequence
<220> FEATURE:
<223> OTHER INFORMATION: inclusion body tag

<400> SEQUENCE: 5

```
catatgcata ccccagaaca catcaccgcc gtggtacagc gctttgtggc tgcgctcaat     60
gccggcgatc tggacggcat cgtcgcgctg tttgccgatg acgccacggt ggaagagccc    120
gtgggttccg agcccaggtc cggtacggct cgtgtgtcgtg agttttacgc caactcgctc   180
aaactgcctt tggcggtgga gctgacgcag gagtgccgcg cggtcgccaa cgaagcggcc    240
ttcgctttca ccgtcagctt cgagtatcag ggccgcaaga ccgtagttgc gccctgtgat    300
cactttcgct tcaatggcgc cggcaaggtg gtgagcatcc gcgccttgtt tggcgagaag    360
aatattcacg catgccaggg atcc                                           384
```

<210> SEQ ID NO 6
<211> LENGTH: 128
<212> TYPE: PRT
<213> ORGANISM: artificial sequence
<220> FEATURE:
<223> OTHER INFORMATION: inclusion body tag

<400> SEQUENCE: 6

```
Met His Thr Pro Glu His Ile Thr Ala Val Val Gln Arg Phe Val Ala
1               5                   10                  15

Ala Leu Asn Ala Gly Asp Leu Asp Gly Ile Val Ala Leu Phe Ala Asp
            20                  25                  30

Asp Ala Thr Val Glu Glu Pro Val Gly Ser Glu Pro Arg Ser Gly Thr
        35                  40                  45

Ala Ala Cys Arg Glu Phe Tyr Ala Asn Ser Leu Lys Leu Pro Leu Ala
    50                  55                  60

Val Glu Leu Thr Gln Glu Cys Arg Ala Val Ala Asn Glu Ala Ala Phe
65                  70                  75                  80

Ala Phe Thr Val Ser Phe Glu Tyr Gln Gly Arg Lys Thr Val Val Ala
                85                  90                  95

Pro Cys Asp His Phe Arg Phe Asn Gly Ala Gly Lys Val Val Ser Ile
            100                 105                 110

Arg Ala Leu Phe Gly Glu Lys Asn Ile His Ala Cys Gln Gly Ser Asp
        115                 120                 125
```

<210> SEQ ID NO 7
<211> LENGTH: 599
<212> TYPE: DNA
<213> ORGANISM: artificial sequence

```
<220> FEATURE:
<223> OTHER INFORMATION: fusion peptide

<400> SEQUENCE: 7
atgcataccc cagaacacat caccgccgtg gtacagcgct ttgtggctgc gctcaatgcc    60
ggcgatctgg acggcatcgt cgcgctgttt gccgatgacg ccacggtgga agaccccgtg   120
ggttccgagc ccaggtccgg tacgctgcg attcgtgagt tttacgccaa ctcgctcaaa   180
ctgcctttgg cggtggagct gacgcaggag gtacgcgcgg tcgccaacga agcggccttc   240
gctttcaccg tcagcttcga gtatcagggc cgcaagaccg tagttgcgcc catcgatcac   300
tttcgcttca atggcgccgg caaggtggtg agcatccgcg ccttgtttgg cgagaagaat   360
attcacgcat gccagggatc cgatccgaac accagtcagc tgagtaccgg cggcggccgc   420
accaacgccg cggatcatcc gaaatgtggc ggcggcaaca ccagccagct gagcaccggt   480
ggcggccgta ccaatgcggc ggatcatccg aaatgtggtg gtggcaatac ctctcagctg   540
agcacgggcg gcgccgtac caatgccgcg gatcatccga atgctaata aggcgcgcc    599

<210> SEQ ID NO 8
<211> LENGTH: 195
<212> TYPE: PRT
<213> ORGANISM: artificial sequence
<220> FEATURE:
<223> OTHER INFORMATION: fusion peptide

<400> SEQUENCE: 8

Met His Thr Pro Glu His Ile Thr Ala Val Val Gln Arg Phe Val Ala
1               5                   10                  15

Ala Leu Asn Ala Gly Asp Leu Asp Gly Ile Val Ala Leu Phe Ala Asp
            20                  25                  30

Asp Ala Thr Val Glu Asp Pro Val Gly Ser Glu Pro Arg Ser Gly Thr
        35                  40                  45

Ala Ala Ile Arg Glu Phe Tyr Ala Asn Ser Leu Lys Leu Pro Leu Ala
    50                  55                  60

Val Glu Leu Thr Gln Glu Val Arg Ala Val Ala Asn Glu Ala Ala Phe
65                  70                  75                  80

Ala Phe Thr Val Ser Phe Glu Tyr Gln Gly Arg Lys Thr Val Val Ala
                85                  90                  95

Pro Ile Asp His Phe Arg Phe Asn Gly Ala Gly Lys Val Val Ser Ile
            100                 105                 110

Arg Ala Leu Phe Gly Glu Lys Asn Ile His Ala Cys Gln Gly Ser Asp
        115                 120                 125

Pro Asn Thr Ser Gln Leu Ser Thr Gly Gly Gly Arg Thr Asn Ala Ala
    130                 135                 140

Asp His Pro Lys Cys Gly Gly Gly Asn Thr Ser Gln Leu Ser Thr Gly
145                 150                 155                 160

Gly Gly Arg Thr Asn Ala Ala Asp His Pro Lys Cys Gly Gly Gly Asn
                165                 170                 175

Thr Ser Gln Leu Ser Thr Gly Gly Gly Arg Thr Asn Ala Ala Asp His
            180                 185                 190

Pro Lys Cys
        195

<210> SEQ ID NO 9
<211> LENGTH: 7
<212> TYPE: PRT
<213> ORGANISM: artificial sequence
<220> FEATURE:
```

<223> OTHER INFORMATION: hair binding peptide

<400> SEQUENCE: 9

Asn Thr Ser Gln Leu Ser Thr
1               5

<210> SEQ ID NO 10
<211> LENGTH: 8
<212> TYPE: PRT
<213> ORGANISM: artificial sequence
<220> FEATURE:
<223> OTHER INFORMATION: hair binding peptide

<400> SEQUENCE: 10

Arg Thr Asn Ala Ala Asp His Pro
1               5

<210> SEQ ID NO 11
<211> LENGTH: 215
<212> TYPE: DNA
<213> ORGANISM: artificial sequence
<220> FEATURE:
<223> OTHER INFORMATION: hair binding peptide

<400> SEQUENCE: 11
ccgaacacca gtcagctgag taccggcggc ggccgcacca acgccgcgga tcatccgaaa      60
tgtggcggcg gcaacaccag ccagctgagc accggtggcg gccgtaccaa tgcggcggat     120
catccgaaat gtggtggtgg caatacctct cagctgagca cgggcggcgg ccgtaccaat     180
gccgcggatc atccgaaatg ctaataaggc gcgcc                                215

<210> SEQ ID NO 12
<211> LENGTH: 69
<212> TYPE: PRT
<213> ORGANISM: artificial sequence
<220> FEATURE:
<223> OTHER INFORMATION: hair binding peptide

<400> SEQUENCE: 12

Gly Ser Pro Asn Thr Ser Gln Leu Ser Thr Gly Gly Gly Arg Thr Asn
1               5                   10                  15

Ala Ala Asp His Pro Lys Cys Gly Gly Gly Asn Thr Ser Gln Leu Ser
            20                  25                  30

Thr Gly Gly Gly Arg Thr Asn Ala Ala Asp His Pro Lys Cys Gly Gly
        35                  40                  45

Gly Asn Thr Ser Gln Leu Ser Thr Gly Gly Gly Arg Thr Asn Ala Ala
    50                  55                  60

Asp His Pro Lys Cys
65

<210> SEQ ID NO 13
<211> LENGTH: 570
<212> TYPE: DNA
<213> ORGANISM: artificial sequence
<220> FEATURE:
<223> OTHER INFORMATION: fusion peptide

<400> SEQUENCE: 13
atgcataccc cagaacacat caccgccgtg gtacagcgct tgtggctgc gctcaatgcc       60 ggcgatctgg acggcatcgt cgcgctgttt gccgatgacg ccacggtgga agagcccgtg     120
ggttccgagc caggtccgg tacgctgcg tgtcgtgagt tttacgccaa ctcgctcaaa       180 ctgccttttgg cggtggagct gacgcaggag tgccgcgcgg tcgccaacga agcggccttc    240

```
gctttcaccg tcagcttcga gtatcagggc cgcaagaccg tagttgcgcc ctgtgatcac    300
tttcgcttca atggcgccgg caaggtggtg agcatccgcg ccttgtttgg cgagaagaat    360
attcacgcat gccagggatc cgaccctggt atcccgtggt ggaacattcg cgcacctctg    420
aatgctggtg ctggtattcc gtggtggaac atccgtgctc ctctgaacgc gggtggctcc    480
ggtccgggct ccggtggcaa cacgagccaa ctgagcaccg gtggtggcaa cacttcccag    540
ctgtccaccg gcggtccgaa aaagtaataa                                     570
```

```
<210> SEQ ID NO 14
<211> LENGTH: 188
<212> TYPE: PRT
<213> ORGANISM: artificial sequence
<220> FEATURE:
<223> OTHER INFORMATION: fusion peptide

<400> SEQUENCE: 14

Met His Thr Pro Glu His Ile Thr Ala Val Val Gln Arg Phe Val Ala
1               5                   10                  15

Ala Leu Asn Ala Gly Asp Leu Asp Gly Ile Val Ala Leu Phe Ala Asp
            20                  25                  30

Asp Ala Thr Val Glu Glu Pro Val Gly Ser Glu Pro Arg Ser Gly Thr
        35                  40                  45

Ala Ala Cys Arg Glu Phe Tyr Ala Asn Ser Leu Lys Leu Pro Leu Ala
    50                  55                  60

Val Glu Leu Thr Gln Glu Cys Arg Ala Val Ala Asn Glu Ala Ala Phe
65                  70                  75                  80

Ala Phe Thr Val Ser Phe Glu Tyr Gln Gly Arg Lys Thr Val Val Ala
                85                  90                  95

Pro Cys Asp His Phe Arg Phe Asn Gly Ala Gly Lys Val Val Ser Ile
            100                 105                 110

Arg Ala Leu Phe Gly Glu Lys Asn Ile His Ala Cys Gln Gly Ser Asp
        115                 120                 125

Pro Gly Ile Pro Trp Trp Asn Ile Arg Ala Pro Leu Asn Ala Gly Ala
    130                 135                 140

Gly Ile Pro Trp Trp Asn Ile Arg Ala Pro Leu Asn Ala Gly Gly Ser
145                 150                 155                 160

Gly Pro Gly Ser Gly Gly Asn Thr Ser Gln Leu Ser Thr Gly Gly Gly
                165                 170                 175

Asn Thr Ser Gln Leu Ser Thr Gly Gly Pro Lys Lys
            180                 185
```

```
<210> SEQ ID NO 15
<211> LENGTH: 12
<212> TYPE: PRT
<213> ORGANISM: artificial sequence
<220> FEATURE:
<223> OTHER INFORMATION: hair binding peptide

<400> SEQUENCE: 15

Ile Pro Trp Trp Asn Ile Arg Ala Pro Leu Asn Ala
1               5                   10
```

```
<210> SEQ ID NO 16
<211> LENGTH: 189
<212> TYPE: DNA
<213> ORGANISM: artificial sequence
<220> FEATURE:
<223> OTHER INFORMATION: hair binding peptide
```

```
<400> SEQUENCE: 16
gaccctggta tcccgtggtg gaacattcgc gcacctctga atgctggtgc tggtattccg    60
tggtggaaca tccgtgctcc tctgaacgcg ggtggctccg gtccgggctc cggtggcaac   120
acgagccaac tgagcaccgg tggtggcaac acttcccagc tgtccaccgg cggtccgaaa   180
aagtaataa                                                            189

<210> SEQ ID NO 17
<211> LENGTH: 61
<212> TYPE: PRT
<213> ORGANISM: artificial sequence
<220> FEATURE:
<223> OTHER INFORMATION: hair binding peptide

<400> SEQUENCE: 17

Asp Pro Gly Ile Pro Trp Trp Asn Ile Arg Ala Pro Leu Asn Ala Gly
1               5                   10                  15

Ala Gly Ile Pro Trp Trp Asn Ile Arg Ala Pro Leu Asn Ala Gly Gly
            20                  25                  30

Ser Gly Pro Gly Ser Gly Gly Asn Thr Ser Gln Leu Ser Thr Gly Gly
        35                  40                  45

Gly Asn Thr Ser Gln Leu Ser Thr Gly Gly Pro Lys Lys
    50                  55                  60

<210> SEQ ID NO 18
<211> LENGTH: 56
<212> TYPE: PRT
<213> ORGANISM: artificial sequence
<220> FEATURE:
<223> OTHER INFORMATION: inclusion body tag

<400> SEQUENCE: 18

Met Gln Gln Arg Phe Gln Trp Gln Phe Glu Gln Gln Pro Arg Gly Gln
1               5                   10                  15

Gln Arg Phe Gln Trp Gln Phe Glu Gln Gln Pro Arg Gly Gln Gln Arg
            20                  25                  30

Phe Gln Trp Gln Phe Glu Gln Gln Pro Glu Gly Gln Gln Arg Phe Gln
        35                  40                  45

Trp Gln Phe Glu Gln Gln Gly Ser
    50                  55

<210> SEQ ID NO 19
<211> LENGTH: 558
<212> TYPE: DNA
<213> ORGANISM: artificial sequence
<220> FEATURE:
<223> OTHER INFORMATION: fusion peptide

<400> SEQUENCE: 19
catatgcagc agcgtttcca gtggcagttc gaacagcagc cgcgtggtca gcagcgtttc    60
cagtggcagt tcgaacagca gccgcgtggt cagcagcgtt ccagtggca gttcgaacag   120 cagccggaag tcagcagcg tttccagtgg cagttcgaac agcagggatc cgaccctggc   180
attccgtggt ggaacattcg tgctcctctg aatgcaggtg cgggcatccc ttggtggaat   240
attcgtgctc cgctgaacgc cggtggttcc ggtccgggta cggtggtaa tacttctcag   300 ctgtccacgg gtgcggtaa cactagccag ctgagcacgg gcggccctaa aaagccgggc   360
gacccgggta ttccgtggtg gaatatccgt gcccgctga acgcaggtgc cggcatcccg   420
tggtggaaca ttcgtgcacc tctgaatgct ggtggttccg gtccaggctc tggcggcaac   480
```

```
acttcccagc tgtccaccgg cggtggcaac accagccagc tgtctactgg tggtccgaag    540
aaaccgggtg actaataa                                                  558
```

<210> SEQ ID NO 20
<211> LENGTH: 183
<212> TYPE: PRT
<213> ORGANISM: artificial sequence
<220> FEATURE:
<223> OTHER INFORMATION: fusion peptide

<400> SEQUENCE: 20

```
Met Gln Gln Arg Phe Gln Trp Gln Phe Glu Gln Gln Pro Arg Gly Gln
1               5                   10                  15

Gln Arg Phe Gln Trp Gln Phe Glu Gln Gln Pro Arg Gly Gln Gln Arg
            20                  25                  30

Phe Gln Trp Gln Phe Glu Gln Gln Pro Glu Gly Gln Gln Arg Phe Gln
        35                  40                  45

Trp Gln Phe Glu Gln Gln Gly Ser Asp Pro Gly Ile Pro Trp Trp Asn
    50                  55                  60

Ile Arg Ala Pro Leu Asn Ala Gly Ala Gly Ile Pro Trp Trp Asn Ile
65                  70                  75                  80

Arg Ala Pro Leu Asn Ala Gly Gly Ser Gly Pro Gly Ser Gly Gly Asn
                85                  90                  95

Thr Ser Gln Leu Ser Thr Gly Gly Asn Thr Ser Gln Leu Ser Thr
            100                 105                 110

Gly Gly Pro Lys Lys Pro Gly Asp Pro Gly Ile Pro Trp Trp Asn Ile
        115                 120                 125

Arg Ala Pro Leu Asn Ala Gly Ala Gly Ile Pro Trp Trp Asn Ile Arg
    130                 135                 140

Ala Pro Leu Asn Ala Gly Gly Ser Gly Pro Gly Ser Gly Gly Asn Thr
145                 150                 155                 160

Ser Gln Leu Ser Thr Gly Gly Gly Asn Thr Ser Gln Leu Ser Thr Gly
                165                 170                 175

Gly Pro Lys Lys Pro Gly Asp
            180
```

<210> SEQ ID NO 21
<211> LENGTH: 387
<212> TYPE: DNA
<213> ORGANISM: artificial sequence
<220> FEATURE:
<223> OTHER INFORMATION: hair binding peptide

<400> SEQUENCE: 21

```
gaccctggca ttccgtggtg gaacattcgt gctcctctga atgcaggtgc gggcatccct    60
tggtggaata ttcgtgctcc gctgaacgcc ggtggttccg gtccgggtag cggtggtaat    120
acttctcagc tgtccacggg tggcggtaac actagccagc tgagcacggg cggccctaaa    180
aagccgggcg acccgggtat tccgtggtgg aatatccgtg ccccgctgaa cgcaggtgcc    240
ggcatcccgt ggtggaacat tcgtgcacct ctgaatgctg gtggttccgg tccaggctct    300
ggcggcaaca cttcccagct gtccaccggc ggtggcaaca ccagccagct gtctactggt    360
ggtccgaaga aaccgggtga ctaataa                                        387
```

<210> SEQ ID NO 22
<211> LENGTH: 127
<212> TYPE: PRT
<213> ORGANISM: artificial sequence
<220> FEATURE:

<223> OTHER INFORMATION: hair binding peptide

<400> SEQUENCE: 22

Asp Pro Gly Ile Pro Trp Trp Asn Ile Arg Ala Pro Leu Asn Ala Gly
1               5                   10                  15

Ala Gly Ile Pro Trp Trp Asn Ile Arg Ala Pro Leu Asn Ala Gly Gly
            20                  25                  30

Ser Gly Pro Gly Ser Gly Gly Asn Thr Ser Gln Leu Ser Thr Gly Gly
        35                  40                  45

Gly Asn Thr Ser Gln Leu Ser Thr Gly Gly Pro Lys Lys Pro Gly Asp
    50                  55                  60

Pro Gly Ile Pro Trp Trp Asn Ile Arg Ala Pro Leu Asn Ala Gly Ala
65                  70                  75                  80

Gly Ile Pro Trp Trp Asn Ile Arg Ala Pro Leu Asn Ala Gly Gly Ser
                85                  90                  95

Gly Pro Gly Ser Gly Gly Asn Thr Ser Gln Leu Ser Thr Gly Gly Gly
            100                 105                 110

Asn Thr Ser Gln Leu Ser Thr Gly Gly Pro Lys Lys Pro Gly Asp
        115                 120                 125

<210> SEQ ID NO 23
<211> LENGTH: 150
<212> TYPE: DNA
<213> ORGANISM: artificial sequence
<220> FEATURE:
<223> OTHER INFORMATION: inclusion body tag

<400> SEQUENCE: 23
atggctagct gtggtcagca acgtttccaa tggcaatttg aacagcagcc tcgctgcggt      60
caacagcgct tccagtggca gtttgaacag cagccagaat gcggtcagca acgctttcag     120
tggcaatttg aacaacaacc gtgcggatcc                                      150

<210> SEQ ID NO 24
<211> LENGTH: 50
<212> TYPE: PRT
<213> ORGANISM: artificial sequence
<220> FEATURE:
<223> OTHER INFORMATION: inclusion body tag

<400> SEQUENCE: 24

Met Ala Ser Cys Gly Gln Gln Arg Phe Gln Trp Gln Phe Glu Gln Gln
1               5                   10                  15

Pro Arg Cys Gly Gln Gln Arg Phe Gln Trp Gln Phe Glu Gln Gln Pro
            20                  25                  30

Glu Cys Gly Gln Gln Arg Phe Gln Trp Gln Phe Glu Gln Gln Pro Cys
        35                  40                  45

Gly Ser
    50

<210> SEQ ID NO 25
<211> LENGTH: 534
<212> TYPE: DNA
<213> ORGANISM: artificial sequence
<220> FEATURE:
<223> OTHER INFORMATION: fusion peptide

<400> SEQUENCE: 25
atggctagct gtggtcagca acgtttccaa tggcaatttg aacagcagcc tcgctgcggt      60
caacagcgct tccagtggca gtttgaacag cagccagaat gcggtcagca acgctttcag     120

```
tggcaatttg aacaacaacc gtgcggatcc gaccctggca ttccgtggtg aacattcgt    180 gctcctctga atgcaggtgc gggcatccct tggtggaata ttcgtgctcc gctgaacgcc    240
ggtggttccg gtccgggtag cggtggtaat acttctcagc tgtccacggg tggcggtaac    300
actagccagc tgagcacggg cggccctaaa aagccgggcg accgggtat tccgtggtgg     360 aatatccgtg ccccgctgaa cgcaggtgcc ggcatcccgt ggtggaacat tcgtgcacct    420
ctgaatgctg gtggttccgg tccaggctct ggcggcaaca cttcccagct gtccaccggc    480
ggtggcaaca ccagccagct gtctactggt ggtccgaaga aaccgggtga ctaa           534
```

<210> SEQ ID NO 26
<211> LENGTH: 177
<212> TYPE: PRT
<213> ORGANISM: artificial sequence
<220> FEATURE:
<223> OTHER INFORMATION: fusion peptide

<400> SEQUENCE: 26

```
Met Ala Ser Cys Gly Gln Gln Arg Phe Gln Trp Gln Phe Glu Gln Gln
1               5                   10                  15

Pro Arg Cys Gly Gln Gln Arg Phe Gln Trp Gln Phe Glu Gln Gln Pro
            20                  25                  30

Glu Cys Gly Gln Gln Arg Phe Gln Trp Gln Phe Glu Gln Gln Pro Cys
        35                  40                  45

Gly Ser Asp Pro Gly Ile Pro Trp Trp Asn Ile Arg Ala Pro Leu Asn
    50                  55                  60

Ala Gly Ala Gly Ile Pro Trp Trp Asn Ile Arg Ala Pro Leu Asn Ala
65                  70                  75                  80

Gly Gly Ser Gly Pro Gly Ser Gly Gly Asn Thr Ser Gln Leu Ser Thr
                85                  90                  95

Gly Gly Gly Asn Thr Ser Gln Leu Ser Thr Gly Gly Pro Lys Lys Pro
            100                 105                 110

Gly Asp Pro Gly Ile Pro Trp Trp Asn Ile Arg Ala Pro Leu Asn Ala
        115                 120                 125

Gly Ala Gly Ile Pro Trp Trp Asn Ile Arg Ala Pro Leu Asn Ala Gly
    130                 135                 140

Gly Ser Gly Pro Gly Ser Gly Gly Asn Thr Ser Gln Leu Ser Thr Gly
145                 150                 155                 160

Gly Gly Asn Thr Ser Gln Leu Ser Thr Gly Gly Pro Lys Lys Pro Gly
                165                 170                 175

Asp
```

<210> SEQ ID NO 27
<211> LENGTH: 64
<212> TYPE: PRT
<213> ORGANISM: artificial sequence
<220> FEATURE:
<223> OTHER INFORMATION: inclusion body tag

<400> SEQUENCE: 27

```
Met Gln Gln Arg Phe Gln Trp Gln Phe Glu Gln Gln Pro Arg Gly Gln
1               5                   10                  15

Gln Arg Phe Gln Trp Gln Phe Glu Gln Gln Pro Arg Gly Gln Gln Arg
            20                  25                  30

Phe Gln Trp Gln Phe Glu Gln Gln Pro Glu Gly Gln Gln Arg Phe Gln
        35                  40                  45

Trp Gln Phe Glu Gln Gln Gly Ser Cys Cys Pro Gly Cys Cys Gly Ser
    50                  55                  60
```

<210> SEQ ID NO 28
<211> LENGTH: 579
<212> TYPE: DNA
<213> ORGANISM: artificial sequence
<220> FEATURE:
<223> OTHER INFORMATION: fusion peptide

<400> SEQUENCE: 28

```
atgcagcagc gtttccagtg gcagttcgaa cagcagccgc gtggtcagca gcgtttccag      60
tggcagttcg aacagcagcc gcgtggtcag cagcgtttcc agtggcagtt cgaacagcag     120
ccggaaggtc agcagcgttt ccagtggcag ttcgaacagc agggatcttg ctgtccgggc     180
tgttgcggat ccgaccctgg cattccgtgg tggaacattc gtgctcctct gaatgcaggt     240
gcgggcatcc cttggtggaa tattcgtgct ccgctgaacg ccgtggttc cggtccgggt     300
agcggtggta atacttctca gctgtccacg ggtggcggta acactagcca gctgagcacg     360
ggcggcccta aaaagccggg cgacccgggt attccgtggt ggaatatccg tgccccgctg     420
aacgcaggtg ccggcatccc gtggtggaac attcgtgcac tctgaatgc tggtggttcc     480
ggtccaggct ctggcggcaa cacttcccag ctgtccaccg gcggtggcaa caccagccag     540
ctgtctactg gtggtccgaa gaaaccgggt gactaataa                           579
```

<210> SEQ ID NO 29
<211> LENGTH: 191
<212> TYPE: PRT
<213> ORGANISM: artificial sequence
<220> FEATURE:
<223> OTHER INFORMATION: fusion peptide

<400> SEQUENCE: 29

Met Gln Gln Arg Phe Gln Trp Gln Phe Glu Gln Gln Pro Arg Gly Gln
1               5                   10                  15

Gln Arg Phe Gln Trp Gln Phe Glu Gln Gln Pro Arg Gly Gln Gln Arg
            20                  25                  30

Phe Gln Trp Gln Phe Glu Gln Gln Pro Glu Gly Gln Gln Arg Phe Gln
        35                  40                  45

Trp Gln Phe Glu Gln Gln Gly Ser Cys Cys Pro Gly Cys Cys Gly Ser
    50                  55                  60

Asp Pro Gly Ile Pro Trp Trp Asn Ile Arg Ala Pro Leu Asn Ala Gly
65                  70                  75                  80

Ala Gly Ile Pro Trp Trp Asn Ile Arg Ala Pro Leu Asn Ala Gly Gly
                85                  90                  95

Ser Gly Pro Gly Ser Gly Gly Asn Thr Ser Gln Leu Ser Thr Gly Gly
            100                 105                 110

Gly Asn Thr Ser Gln Leu Ser Thr Gly Gly Pro Lys Lys Pro Gly Asp
        115                 120                 125

Pro Gly Ile Pro Trp Trp Asn Ile Arg Ala Pro Leu Asn Ala Gly Ala
    130                 135                 140

Gly Ile Pro Trp Trp Asn Ile Arg Ala Pro Leu Asn Ala Gly Gly Ser
145                 150                 155                 160

Gly Pro Gly Ser Gly Gly Asn Thr Ser Gln Leu Ser Thr Gly Gly Gly
                165                 170                 175

Asn Thr Ser Gln Leu Ser Thr Gly Gly Pro Lys Lys Pro Gly Asp
            180                 185                 190

<210> SEQ ID NO 30
<211> LENGTH: 6

```
<212> TYPE: PRT
<213> ORGANISM: artificial sequence
<220> FEATURE:
<223> OTHER INFORMATION: synthetic cysteine motif
<220> FEATURE:
<221> NAME/KEY: misc_feature
<222> LOCATION: (3)..(4)
<223> OTHER INFORMATION: Xaa can be any naturally occurring amino acid

<400> SEQUENCE: 30

Cys Cys Xaa Xaa Cys Cys
1               5

<210> SEQ ID NO 31
<211> LENGTH: 18
<212> TYPE: DNA
<213> ORGANISM: artificial sequence
<220> FEATURE:
<223> OTHER INFORMATION: Synthetic sequence encoding CCPGCC cysteine
      motif

<400> SEQUENCE: 31
tgctgtccgg gctgttgc                                                 18

<210> SEQ ID NO 32
<211> LENGTH: 6
<212> TYPE: PRT
<213> ORGANISM: artificial sequence
<220> FEATURE:
<223> OTHER INFORMATION: synthetic cysteine motif

<400> SEQUENCE: 32

Cys Cys Pro Gly Cys Cys
1               5

<210> SEQ ID NO 33
<211> LENGTH: 24
<212> TYPE: DNA
<213> ORGANISM: artificial sequence
<220> FEATURE:
<223> OTHER INFORMATION: primer

<400> SEQUENCE: 33
gatcttgctg tccgggctgt tgcg                                          24

<210> SEQ ID NO 34
<211> LENGTH: 24
<212> TYPE: DNA
<213> ORGANISM: artificial sequence
<220> FEATURE:
<223> OTHER INFORMATION: primer

<400> SEQUENCE: 34
gatccgcaac agcccggaca gcaa                                          24

<210> SEQ ID NO 35
<211> LENGTH: 12
<212> TYPE: PRT
<213> ORGANISM: artificial sequence
<220> FEATURE:
<223> OTHER INFORMATION: hair binding peptide

<400> SEQUENCE: 35

Thr Pro Pro Glu Leu Leu His Gly Asp Pro Arg Ser
1               5                   10

<210> SEQ ID NO 36
<211> LENGTH: 12
```

```
<212> TYPE: PRT
<213> ORGANISM: artificial sequence
<220> FEATURE:
<223> OTHER INFORMATION: hair binding peptide

<400> SEQUENCE: 36

Arg Thr Asn Ala Ala Asp His Pro Ala Ala Val Thr
1               5                   10

<210> SEQ ID NO 37
<211> LENGTH: 7
<212> TYPE: PRT
<213> ORGANISM: artificial sequence
<220> FEATURE:
<223> OTHER INFORMATION: hair binding peptide

<400> SEQUENCE: 37

Asp Leu Thr Leu Pro Phe His
1               5

<210> SEQ ID NO 38
<211> LENGTH: 12
<212> TYPE: PRT
<213> ORGANISM: artificial sequence
<220> FEATURE:
<223> OTHER INFORMATION: hair and skin binding peptide

<400> SEQUENCE: 38

Lys Arg Gly Arg His Lys Arg Pro Lys Arg His Lys
1               5                   10

<210> SEQ ID NO 39
<211> LENGTH: 7
<212> TYPE: PRT
<213> ORGANISM: artificial sequence
<220> FEATURE:
<223> OTHER INFORMATION: hair and skin binding peptide

<400> SEQUENCE: 39

Arg Leu Leu Arg Leu Leu Arg
1               5

<210> SEQ ID NO 40
<211> LENGTH: 12
<212> TYPE: PRT
<213> ORGANISM: artificial sequence
<220> FEATURE:
<223> OTHER INFORMATION: hair and skin binding peptide

<400> SEQUENCE: 40

His Lys Pro Arg Gly Gly Arg Lys Lys Ala Leu His
1               5                   10

<210> SEQ ID NO 41
<211> LENGTH: 18
<212> TYPE: PRT
<213> ORGANISM: artificial sequence
<220> FEATURE:
<223> OTHER INFORMATION: hair and skin binding peptide

<400> SEQUENCE: 41

Lys Pro Arg Pro Pro His Gly Lys Lys His Arg Pro Lys His Arg Pro
1               5                   10                  15

Lys Lys

<210> SEQ ID NO 42
<211> LENGTH: 18
```

```
<212> TYPE: PRT
<213> ORGANISM: artificial sequence
<220> FEATURE:
<223> OTHER INFORMATION: hair and skin binding peptide

<400> SEQUENCE: 42

Arg Gly Arg Pro Lys Lys Gly His Gly Lys Arg Pro Gly His Arg Ala
1               5                   10                  15

Arg Lys

<210> SEQ ID NO 43
<211> LENGTH: 55
<212> TYPE: PRT
<213> ORGANISM: artificial sequence
<220> FEATURE:
<223> OTHER INFORMATION: hair binding peptide

<400> SEQUENCE: 43

Pro Arg Thr Asn Ala Ala Asp His Pro Ala Ala Val Thr Gly Gly Gly
1               5                   10                  15

Cys Gly Gly Gly Arg Thr Asn Ala Ala Asp His Pro Ala Ala Val Thr
            20                  25                  30

Gly Gly Gly Cys Gly Gly Gly Arg Thr Asn Ala Ala Asp His Pro Ala
        35                  40                  45

Ala Val Thr Gly Gly Gly Cys
    50                  55

<210> SEQ ID NO 44
<211> LENGTH: 50
<212> TYPE: PRT
<213> ORGANISM: artificial sequence
<220> FEATURE:
<223> OTHER INFORMATION: hair binding peptide

<400> SEQUENCE: 44

Pro Arg Thr Asn Ala Ala Asp His Pro Ala Ala Val Thr Gly Gly Gly
1               5                   10                  15

Cys Gly Gly Gly Ile Pro Trp Trp Asn Ile Arg Ala Pro Leu Asn Ala
            20                  25                  30

Gly Gly Gly Cys Gly Gly Gly Asp Leu Thr Leu Pro Phe His Gly Gly
        35                  40                  45

Gly Cys
    50

<210> SEQ ID NO 45
<211> LENGTH: 82
<212> TYPE: PRT
<213> ORGANISM: artificial sequence
<220> FEATURE:
<223> OTHER INFORMATION: hair binding peptide

<400> SEQUENCE: 45

Pro Arg Thr Asn Ala Ala Asp His Pro Gly Gly Gly Thr Pro Pro Glu
1               5                   10                  15

Leu Leu His Gly Asp Pro Arg Ser Lys Cys Gly Gly Gly Arg Thr Asn
            20                  25                  30

Ala Ala Asp His Pro Gly Gly Gly Thr Pro Pro Glu Leu Leu His Gly
        35                  40                  45

Asp Pro Arg Ser Lys Cys Gly Gly Gly Arg Thr Asn Ala Ala Asp His
    50                  55                  60

Pro Gly Gly Gly Thr Pro Pro Glu Leu Leu His Gly Asp Pro Arg Ser
65                  70                  75                  80
```

```
<210> SEQ ID NO 46
<211> LENGTH: 82
<212> TYPE: PRT
<213> ORGANISM: artificial sequence
<220> FEATURE:
<223> OTHER INFORMATION: hair binding peptide

<400> SEQUENCE: 46

Pro Thr Pro Pro Thr Asn Val Leu Met Leu Ala Thr Lys Gly Gly Gly
1               5                   10                  15

Arg Thr Asn Ala Ala Asp His Pro Lys Cys Gly Gly Thr Pro Pro
            20                  25                  30

Thr Asn Val Leu Met Leu Ala Thr Lys Gly Gly Gly Arg Thr Asn Ala
                35                  40                  45

Ala Asp His Pro Lys Cys Gly Gly Thr Pro Pro Thr Asn Val Leu
        50                  55                  60

Met Leu Ala Thr Lys Gly Gly Gly Arg Thr Asn Ala Ala Asp His Pro
65                  70                  75                  80

Lys Cys

<210> SEQ ID NO 47
<211> LENGTH: 82
<212> TYPE: PRT
<213> ORGANISM: artificial sequence
<220> FEATURE:
<223> OTHER INFORMATION: hair binding peptide

<400> SEQUENCE: 47

Pro Arg Thr Asn Ala Ala Asp His Pro Gly Gly Gly Thr Pro Pro Thr
1               5                   10                  15

Asn Val Leu Met Leu Ala Thr Lys Lys Cys Gly Gly Gly Arg Thr Asn
                20                  25                  30

Ala Ala Asp His Pro Gly Gly Gly Thr Pro Pro Thr Asn Val Leu Met
            35                  40                  45

Leu Ala Thr Lys Lys Cys Gly Gly Gly Arg Thr Asn Ala Ala Asp His
        50                  55                  60

Pro Gly Gly Gly Thr Pro Pro Thr Asn Val Leu Met Leu Ala Thr Lys
65                  70                  75                  80

Lys Cys

<210> SEQ ID NO 48
<211> LENGTH: 13
<212> TYPE: PRT
<213> ORGANISM: artificial sequence
<220> FEATURE:
<223> OTHER INFORMATION: hair binding peptide

<400> SEQUENCE: 48

Thr Pro Pro Glu Leu Leu His Gly Asp Pro Arg Ser Cys
1               5                   10

<210> SEQ ID NO 49
<211> LENGTH: 12
<212> TYPE: PRT
<213> ORGANISM: artificial sequence
<220> FEATURE:
<223> OTHER INFORMATION: hair binding peptide

<400> SEQUENCE: 49
```

-continued

```
Glu Gln Ile Ser Gly Ser Leu Val Ala Ala Pro Trp
1               5                   10

<210> SEQ ID NO 50
<211> LENGTH: 12
<212> TYPE: PRT
<213> ORGANISM: artificial sequence
<220> FEATURE:
<223> OTHER INFORMATION: hair binding peptide

<400> SEQUENCE: 50

Thr Asp Met Gln Ala Pro Thr Lys Ser Tyr Ser Asn
1               5                   10

<210> SEQ ID NO 51
<211> LENGTH: 12
<212> TYPE: PRT
<213> ORGANISM: artificial sequence
<220> FEATURE:
<223> OTHER INFORMATION: hair binding peptide

<400> SEQUENCE: 51

Ala Leu Pro Arg Ile Ala Asn Thr Trp Ser Pro Ser
1               5                   10

<210> SEQ ID NO 52
<211> LENGTH: 12
<212> TYPE: PRT
<213> ORGANISM: artificial sequence
<220> FEATURE:
<223> OTHER INFORMATION: hair binding peptide

<400> SEQUENCE: 52

Leu Asp Thr Ser Phe Pro Pro Val Pro Phe His Ala
1               5                   10

<210> SEQ ID NO 53
<211> LENGTH: 12
<212> TYPE: PRT
<213> ORGANISM: artificial sequence
<220> FEATURE:
<223> OTHER INFORMATION: hair binding peptide

<400> SEQUENCE: 53

Thr Pro Pro Thr Asn Val Leu Met Leu Ala Thr Lys
1               5                   10

<210> SEQ ID NO 54
<211> LENGTH: 15
<212> TYPE: PRT
<213> ORGANISM: artificial sequence
<220> FEATURE:
<223> OTHER INFORMATION: hair binding peptide

<400> SEQUENCE: 54

Ser Thr Leu His Lys Tyr Lys Ser Gln Asp Pro Thr Pro His His
1               5                   10                  15

<210> SEQ ID NO 55
<211> LENGTH: 12
<212> TYPE: PRT
<213> ORGANISM: artificial sequence
<220> FEATURE:
<223> OTHER INFORMATION: hair binding peptide

<400> SEQUENCE: 55

Gly Met Pro Ala Met His Trp Ile His Pro Phe Ala
1               5                   10
```

```
<210> SEQ ID NO 56
<211> LENGTH: 15
<212> TYPE: PRT
<213> ORGANISM: artificial sequence
<220> FEATURE:
<223> OTHER INFORMATION: hair binding peptide

<400> SEQUENCE: 56

His Asp His Lys Asn Gln Lys Glu Thr His Gln Arg His Ala Ala
1               5                   10                  15

<210> SEQ ID NO 57
<211> LENGTH: 20
<212> TYPE: PRT
<213> ORGANISM: artificial sequence
<220> FEATURE:
<223> OTHER INFORMATION: hair binding peptide

<400> SEQUENCE: 57

His Asn His Met Gln Glu Arg Tyr Thr Asp Pro Gln His Ser Pro Ser
1               5                   10                  15

Val Asn Gly Leu
            20

<210> SEQ ID NO 58
<211> LENGTH: 20
<212> TYPE: PRT
<213> ORGANISM: artificial sequence
<220> FEATURE:
<223> OTHER INFORMATION: hair binding peptide

<400> SEQUENCE: 58

Thr Ala Glu Ile Gln Ser Ser Lys Asn Pro Asn Pro His Pro Gln Arg
1               5                   10                  15

Ser Trp Thr Asn
            20

<210> SEQ ID NO 59
<211> LENGTH: 12
<212> TYPE: PRT
<213> ORGANISM: artificial sequence
<220> FEATURE:
<223> OTHER INFORMATION: skin binding peptide

<400> SEQUENCE: 59

Thr Pro Phe His Ser Pro Glu Asn Ala Pro Gly Ser
1               5                   10

<210> SEQ ID NO 60
<211> LENGTH: 12
<212> TYPE: PRT
<213> ORGANISM: artificial sequence
<220> FEATURE:
<223> OTHER INFORMATION: skin binding peptide

<400> SEQUENCE: 60

Thr Met Gly Phe Thr Ala Pro Arg Phe Pro His Tyr
1               5                   10

<210> SEQ ID NO 61
<211> LENGTH: 12
<212> TYPE: PRT
<213> ORGANISM: artificial sequence
<220> FEATURE:
<223> OTHER INFORMATION: skin binding peptide
```

-continued

```
<400> SEQUENCE: 61

Ser Val Ser Val Gly Met Lys Pro Ser Pro Arg Pro
1               5                   10

<210> SEQ ID NO 62
<211> LENGTH: 12
<212> TYPE: PRT
<213> ORGANISM: artificial sequence
<220> FEATURE:
<223> OTHER INFORMATION: skin binding peptide

<400> SEQUENCE: 62

Asn Leu Gln His Ser Val Gly Thr Ser Pro Val Trp
1               5                   10

<210> SEQ ID NO 63
<211> LENGTH: 15
<212> TYPE: PRT
<213> ORGANISM: artificial sequence
<220> FEATURE:
<223> OTHER INFORMATION: skin binding peptide

<400> SEQUENCE: 63

Gln Leu Ser Tyr His Ala Tyr Pro Gln Ala Asn His His Ala Pro
1               5                   10                  15

<210> SEQ ID NO 64
<211> LENGTH: 14
<212> TYPE: PRT
<213> ORGANISM: artificial sequence
<220> FEATURE:
<223> OTHER INFORMATION: skin binding peptide

<400> SEQUENCE: 64

Ser Gly Cys His Leu Val Tyr Asp Asn Gly Phe Cys Asp His
1               5                   10

<210> SEQ ID NO 65
<211> LENGTH: 14
<212> TYPE: PRT
<213> ORGANISM: artificial sequence
<220> FEATURE:
<223> OTHER INFORMATION: skin binding peptide

<400> SEQUENCE: 65

Ala Ser Cys Pro Ser Ala Ser His Ala Asp Pro Cys Ala His
1               5                   10

<210> SEQ ID NO 66
<211> LENGTH: 14
<212> TYPE: PRT
<213> ORGANISM: artificial sequence
<220> FEATURE:
<223> OTHER INFORMATION: skin binding peptide

<400> SEQUENCE: 66

Asn Leu Cys Asp Ser Ala Arg Asp Ser Pro Arg Cys Lys Val
1               5                   10

<210> SEQ ID NO 67
<211> LENGTH: 12
<212> TYPE: PRT
<213> ORGANISM: artificial sequence
<220> FEATURE:
<223> OTHER INFORMATION: skin binding peptide

<400> SEQUENCE: 67
```

Asn His Ser Asn Trp Lys Thr Ala Ala Asp Phe Leu
1               5                   10

<210> SEQ ID NO 68
<211> LENGTH: 12
<212> TYPE: PRT
<213> ORGANISM: artificial sequence
<220> FEATURE:
<223> OTHER INFORMATION: skin binding peptide

<400> SEQUENCE: 68

Ser Asp Thr Ile Ser Arg Leu His Val Ser Met Thr
1               5                   10

<210> SEQ ID NO 69
<211> LENGTH: 12
<212> TYPE: PRT
<213> ORGANISM: artificial sequence
<220> FEATURE:
<223> OTHER INFORMATION: skin binding peptide

<400> SEQUENCE: 69

Ser Pro Tyr Pro Ser Trp Ser Thr Pro Ala Gly Arg
1               5                   10

<210> SEQ ID NO 70
<211> LENGTH: 14
<212> TYPE: PRT
<213> ORGANISM: artificial sequence
<220> FEATURE:
<223> OTHER INFORMATION: skin binding peptide

<400> SEQUENCE: 70

Asp Ala Cys Ser Gly Asn Gly His Pro Asn Asn Cys Asp Arg
1               5                   10

<210> SEQ ID NO 71
<211> LENGTH: 14
<212> TYPE: PRT
<213> ORGANISM: artificial sequence
<220> FEATURE:
<223> OTHER INFORMATION: skin binding peptide

<400> SEQUENCE: 71

Asp Trp Cys Asp Thr Ile Ile Pro Gly Arg Thr Cys His Gly
1               5                   10

<210> SEQ ID NO 72
<211> LENGTH: 12
<212> TYPE: PRT
<213> ORGANISM: artificial sequence
<220> FEATURE:
<223> OTHER INFORMATION: Nail binding peptide

<400> SEQUENCE: 72

Ala Leu Pro Arg Ile Ala Asn Thr Trp Ser Pro Ser
1               5                   10

<210> SEQ ID NO 73
<211> LENGTH: 12
<212> TYPE: PRT
<213> ORGANISM: artificial sequence
<220> FEATURE:
<223> OTHER INFORMATION: Nail binding peptide

<400> SEQUENCE: 73

Tyr Pro Ser Phe Ser Pro Thr Tyr Arg Pro Ala Phe
1               5                   10

```
<210> SEQ ID NO 74
<211> LENGTH: 17
<212> TYPE: PRT
<213> ORGANISM: artificial sequence
<220> FEATURE:
<223> OTHER INFORMATION: Antimicrobial peptide

<400> SEQUENCE: 74

Pro Lys Gly Leu Lys Lys Leu Leu Lys Gly Leu Lys Lys Leu Leu Lys
1               5                   10                  15

Leu

<210> SEQ ID NO 75
<211> LENGTH: 16
<212> TYPE: PRT
<213> ORGANISM: artificial sequence
<220> FEATURE:
<223> OTHER INFORMATION: Antimicrobial peptide

<400> SEQUENCE: 75

Lys Gly Leu Lys Lys Leu Leu Lys Gly Leu Lys Lys Leu Leu Lys Leu
1               5                   10                  15

<210> SEQ ID NO 76
<211> LENGTH: 16
<212> TYPE: PRT
<213> ORGANISM: artificial sequence
<220> FEATURE:
<223> OTHER INFORMATION: Antimicrobial peptide

<400> SEQUENCE: 76

Lys Gly Leu Lys Lys Leu Leu Lys Leu Leu Lys Lys Leu Leu Lys Leu
1               5                   10                  15

<210> SEQ ID NO 77
<211> LENGTH: 14
<212> TYPE: PRT
<213> ORGANISM: artificial sequence
<220> FEATURE:
<223> OTHER INFORMATION: Antimicrobial peptide

<400> SEQUENCE: 77

Leu Lys Lys Leu Leu Lys Leu Leu Lys Lys Leu Leu Lys Leu
1               5                   10

<210> SEQ ID NO 78
<211> LENGTH: 12
<212> TYPE: PRT
<213> ORGANISM: artificial sequence
<220> FEATURE:
<223> OTHER INFORMATION: Antimicrobial peptide

<400> SEQUENCE: 78

Leu Lys Lys Leu Leu Lys Leu Leu Lys Lys Leu Leu
1               5                   10

<210> SEQ ID NO 79
<211> LENGTH: 17
<212> TYPE: PRT
<213> ORGANISM: artificial sequence
<220> FEATURE:
<223> OTHER INFORMATION: Antimicrobial peptide

<400> SEQUENCE: 79

Val Ala Lys Lys Leu Ala Lys Leu Ala Lys Lys Leu Ala Lys Leu Ala
1               5                   10                  15
```

Leu

<210> SEQ ID NO 80
<211> LENGTH: 13
<212> TYPE: PRT
<213> ORGANISM: artificial sequence
<220> FEATURE:
<223> OTHER INFORMATION: Antimicrobial peptide

<400> SEQUENCE: 80

Phe Ala Lys Leu Leu Ala Lys Ala Leu Lys Lys Leu Leu
1               5                   10

<210> SEQ ID NO 81
<211> LENGTH: 16
<212> TYPE: PRT
<213> ORGANISM: artificial sequence
<220> FEATURE:
<223> OTHER INFORMATION: Antimicrobial peptide

<400> SEQUENCE: 81

Lys Gly Leu Lys Lys Gly Leu Lys Leu Leu Lys Lys Leu Leu Lys Leu
1               5                   10                  15

<210> SEQ ID NO 82
<211> LENGTH: 16
<212> TYPE: PRT
<213> ORGANISM: artificial sequence
<220> FEATURE:
<223> OTHER INFORMATION: Antimicrobial peptide

<400> SEQUENCE: 82

Lys Gly Leu Lys Lys Leu Leu Lys Leu Gly Lys Lys Leu Leu Lys Leu
1               5                   10                  15

<210> SEQ ID NO 83
<211> LENGTH: 16
<212> TYPE: PRT
<213> ORGANISM: artificial sequence
<220> FEATURE:
<223> OTHER INFORMATION: Antimicrobial peptide

<400> SEQUENCE: 83

Lys Gly Leu Lys Lys Leu Gly Lys Leu Leu Lys Lys Leu Leu Lys Leu
1               5                   10                  15

<210> SEQ ID NO 84
<211> LENGTH: 16
<212> TYPE: PRT
<213> ORGANISM: artificial sequence
<220> FEATURE:
<223> OTHER INFORMATION: Antimicrobial peptide

<400> SEQUENCE: 84

Lys Gly Leu Lys Lys Leu Leu Lys Leu Leu Lys Lys Gly Leu Lys Leu
1               5                   10                  15

<210> SEQ ID NO 85
<211> LENGTH: 16
<212> TYPE: PRT
<213> ORGANISM: artificial sequence
<220> FEATURE:
<223> OTHER INFORMATION: Antimicrobial peptide

<400> SEQUENCE: 85

Lys Gly Leu Lys Lys Leu Leu Lys Leu Leu Lys Lys Leu Gly Lys Leu
1               5                   10                  15

```
<210> SEQ ID NO 86
<211> LENGTH: 19
<212> TYPE: PRT
<213> ORGANISM: artificial sequence
<220> FEATURE:
<223> OTHER INFORMATION: Antimicrobial peptide

<400> SEQUENCE: 86

Phe Ala Leu Ala Leu Lys Ala Leu Lys Lys Leu Lys Lys Ala Leu Lys
1               5                   10                  15

Lys Ala Leu

<210> SEQ ID NO 87
<211> LENGTH: 17
<212> TYPE: PRT
<213> ORGANISM: artificial sequence
<220> FEATURE:
<223> OTHER INFORMATION: Antimicrobial peptide

<400> SEQUENCE: 87

Phe Ala Lys Lys Leu Ala Lys Leu Ala Lys Lys Leu Ala Lys Leu Ala
1               5                   10                  15

Leu

<210> SEQ ID NO 88
<211> LENGTH: 13
<212> TYPE: PRT
<213> ORGANISM: artificial sequence
<220> FEATURE:
<223> OTHER INFORMATION: Antimicrobial peptide

<400> SEQUENCE: 88

Phe Ala Lys Leu Leu Ala Lys Leu Ala Lys Lys Leu Leu
1               5                   10

<210> SEQ ID NO 89
<211> LENGTH: 15
<212> TYPE: PRT
<213> ORGANISM: artificial sequence
<220> FEATURE:
<223> OTHER INFORMATION: Antimicrobial peptide

<400> SEQUENCE: 89

Phe Ala Lys Lys Leu Ala Lys Leu Ala Leu Lys Leu Ala Lys Leu
1               5                   10                  15

<210> SEQ ID NO 90
<211> LENGTH: 10
<212> TYPE: PRT
<213> ORGANISM: artificial sequence
<220> FEATURE:
<223> OTHER INFORMATION: Antimicrobial peptide

<400> SEQUENCE: 90

Phe Ala Lys Lys Leu Ala Lys Lys Leu Leu
1               5                   10

<210> SEQ ID NO 91
<211> LENGTH: 13
<212> TYPE: PRT
<213> ORGANISM: artificial sequence
<220> FEATURE:
<223> OTHER INFORMATION: Antimicrobial peptide

<400> SEQUENCE: 91
```

```
Phe Ala Lys Leu Leu Ala Lys Leu Ala Lys Lys Val Leu
1               5                   10

<210> SEQ ID NO 92
<211> LENGTH: 13
<212> TYPE: PRT
<213> ORGANISM: artificial sequence
<220> FEATURE:
<223> OTHER INFORMATION: Antimicrobial peptide

<400> SEQUENCE: 92

Lys Tyr Lys Lys Ala Leu Lys Lys Leu Ala Lys Leu Leu
1               5                   10

<210> SEQ ID NO 93
<211> LENGTH: 12
<212> TYPE: PRT
<213> ORGANISM: artificial sequence
<220> FEATURE:
<223> OTHER INFORMATION: Antimicrobial peptide

<400> SEQUENCE: 93

Phe Ala Leu Leu Lys Ala Leu Leu Lys Lys Ala Leu
1               5                   10

<210> SEQ ID NO 94
<211> LENGTH: 14
<212> TYPE: PRT
<213> ORGANISM: artificial sequence
<220> FEATURE:
<223> OTHER INFORMATION: Antimicrobial peptide

<400> SEQUENCE: 94

Lys Arg Leu Phe Lys Lys Leu Lys Phe Ser Leu Arg Lys Tyr
1               5                   10

<210> SEQ ID NO 95
<211> LENGTH: 14
<212> TYPE: PRT
<213> ORGANISM: artificial sequence
<220> FEATURE:
<223> OTHER INFORMATION: Antimicrobial peptide

<400> SEQUENCE: 95

Lys Arg Leu Phe Lys Lys Leu Leu Phe Ser Leu Arg Lys Tyr
1               5                   10

<210> SEQ ID NO 96
<211> LENGTH: 14
<212> TYPE: PRT
<213> ORGANISM: artificial sequence
<220> FEATURE:
<223> OTHER INFORMATION: Antimicrobial peptide

<400> SEQUENCE: 96

Leu Leu Leu Phe Leu Leu Lys Lys Arg Lys Lys Arg Lys Tyr
1               5                   10

<210> SEQ ID NO 97
<211> LENGTH: 36
<212> TYPE: PRT
<213> ORGANISM: Hyalophora cecropia

<400> SEQUENCE: 97

Lys Trp Lys Leu Phe Lys Lys Ile Glu Lys Val Gly Gln Asn Ile Arg
1               5                   10                  15

Asp Gly Ile Ile Lys Ala Gly Pro Ala Val Ala Trp Gly Gln Ala Thr
```

```
                    20                  25                  30

Gln Ile Ala Lys
        35

<210> SEQ ID NO 98
<211> LENGTH: 23
<212> TYPE: PRT
<213> ORGANISM: Xenopus sp.

<400> SEQUENCE: 98

Gly Ile Gly Lys Phe Leu His Ser Ala Lys Lys Phe Gly Lys Ala Phe
1               5                   10                  15

Val Gly Glu Ile Met Asn Ser
            20

<210> SEQ ID NO 99
<211> LENGTH: 22
<212> TYPE: PRT
<213> ORGANISM: Xenopus sp.

<400> SEQUENCE: 99

Gly Ile Gly Lys Phe Leu Lys Lys Ala Lys Lys Phe Gly Lys Ala Phe
1               5                   10                  15

Val Lys Ile Leu Lys Lys
            20

<210> SEQ ID NO 100
<211> LENGTH: 12
<212> TYPE: PRT
<213> ORGANISM: Bos Taurus

<400> SEQUENCE: 100

Arg Leu Cys Arg Ile Val Val Ile Arg Val Cys Arg
1               5                   10

<210> SEQ ID NO 101
<211> LENGTH: 13
<212> TYPE: PRT
<213> ORGANISM: Bos sp.

<400> SEQUENCE: 101

Ile Leu Pro Trp Lys Trp Pro Trp Trp Pro Trp Arg Arg
1               5                   10

<210> SEQ ID NO 102
<211> LENGTH: 24
<212> TYPE: PRT
<213> ORGANISM: Homo sapiens

<400> SEQUENCE: 102

Asp Ser His Ala Lys Arg His His Gly Tyr Lys Arg Lys Phe His Glu
1               5                   10                  15

Lys His His Ser His Arg Gly Tyr
            20

<210> SEQ ID NO 103
<211> LENGTH: 7
<212> TYPE: PRT
<213> ORGANISM: artificial sequence
<220> FEATURE:
<223> OTHER INFORMATION: Carbon black binding peptide

<400> SEQUENCE: 103

Met Pro Pro Pro Leu Met Gln
```

```
<210> SEQ ID NO 104
<211> LENGTH: 7
<212> TYPE: PRT
<213> ORGANISM: artificial sequence
<220> FEATURE:
<223> OTHER INFORMATION: Carbon black binding peptide

<400> SEQUENCE: 104

Phe His Glu Asn Trp Pro Ser
1               5

<210> SEQ ID NO 105
<211> LENGTH: 12
<212> TYPE: PRT
<213> ORGANISM: artificial sequence
<220> FEATURE:
<223> OTHER INFORMATION: Carbon black binding peptide

<400> SEQUENCE: 105

Arg Thr Ala Pro Thr Thr Pro Leu Leu Leu Ser Leu
1               5                   10

<210> SEQ ID NO 106
<211> LENGTH: 12
<212> TYPE: PRT
<213> ORGANISM: artificial sequence
<220> FEATURE:
<223> OTHER INFORMATION: Carbon black binding peptide

<400> SEQUENCE: 106

Trp His Leu Ser Trp Ser Pro Val Pro Leu Pro Thr
1               5                   10

<210> SEQ ID NO 107
<211> LENGTH: 7
<212> TYPE: PRT
<213> ORGANISM: artificial sequence
<220> FEATURE:
<223> OTHER INFORMATION: Cromophtal Yellow binding peptide

<400> SEQUENCE: 107

Pro His Ala Arg Leu Val Gly
1               5

<210> SEQ ID NO 108
<211> LENGTH: 7
<212> TYPE: PRT
<213> ORGANISM: artificial sequence
<220> FEATURE:
<223> OTHER INFORMATION: Cromophtal Yellow binding peptide

<400> SEQUENCE: 108

Asn Ile Pro Tyr His His Pro
1               5

<210> SEQ ID NO 109
<211> LENGTH: 7
<212> TYPE: PRT
<213> ORGANISM: artificial sequence
<220> FEATURE:
<223> OTHER INFORMATION: Cromophtal Yellow binding peptide

<400> SEQUENCE: 109

Thr Thr Met Pro Ala Ile Pro
1               5
```

```
<210> SEQ ID NO 110
<211> LENGTH: 7
<212> TYPE: PRT
<213> ORGANISM: artificial sequence
<220> FEATURE:
<223> OTHER INFORMATION: Cromophtal Yellow binding peptide

<400> SEQUENCE: 110

His Asn Leu Pro Pro Arg Ser
1               5

<210> SEQ ID NO 111
<211> LENGTH: 12
<212> TYPE: PRT
<213> ORGANISM: artificial sequence
<220> FEATURE:
<223> OTHER INFORMATION: Cromophtal Yellow binding peptide

<400> SEQUENCE: 111

Ala His Lys Thr Gln Met Gly Val Arg Gln Pro Ala
1               5                   10

<210> SEQ ID NO 112
<211> LENGTH: 12
<212> TYPE: PRT
<213> ORGANISM: artificial sequence
<220> FEATURE:
<223> OTHER INFORMATION: Cromophtal Yellow binding peptide

<400> SEQUENCE: 112

Ala Asp Asn Val Gln Met Gly Val Ser His Thr Pro
1               5                   10

<210> SEQ ID NO 113
<211> LENGTH: 12
<212> TYPE: PRT
<213> ORGANISM: artificial sequence
<220> FEATURE:
<223> OTHER INFORMATION: Cromophtal Yellow binding peptide

<400> SEQUENCE: 113

Ala His Asn Ala Gln Met Gly Val Ser His Pro Pro
1               5                   10

<210> SEQ ID NO 114
<211> LENGTH: 12
<212> TYPE: PRT
<213> ORGANISM: artificial sequence
<220> FEATURE:
<223> OTHER INFORMATION: Cromophtal Yellow binding peptide

<400> SEQUENCE: 114

Ala Asp Tyr Val Gly Met Gly Val Ser His Arg Pro
1               5                   10

<210> SEQ ID NO 115
<211> LENGTH: 12
<212> TYPE: PRT
<213> ORGANISM: artificial sequence
<220> FEATURE:
<223> OTHER INFORMATION: Cromophtal Yellow binding peptide

<400> SEQUENCE: 115

Ser Val Ser Val Gly Met Lys Pro Ser Pro Arg Pro
1               5                   10

<210> SEQ ID NO 116
```

```
<211> LENGTH: 7
<212> TYPE: PRT
<213> ORGANISM: artificial sequence
<220> FEATURE:
<223> OTHER INFORMATION: Sunfast Magenta binding peptide

<400> SEQUENCE: 116

Tyr Pro Asn Thr Ala Leu Val
1               5

<210> SEQ ID NO 117
<211> LENGTH: 7
<212> TYPE: PRT
<213> ORGANISM: artificial sequence
<220> FEATURE:
<223> OTHER INFORMATION: Sunfast Magenta binding peptide

<400> SEQUENCE: 117

Val Ala Thr Arg Ile Val Ser
1               5

<210> SEQ ID NO 118
<211> LENGTH: 12
<212> TYPE: PRT
<213> ORGANISM: artificial sequence
<220> FEATURE:
<223> OTHER INFORMATION: Sunfast Magenta binding peptide

<400> SEQUENCE: 118

His Ser Leu Lys Asn Ser Met Leu Thr Val Met Ala
1               5                   10

<210> SEQ ID NO 119
<211> LENGTH: 7
<212> TYPE: PRT
<213> ORGANISM: artificial sequence
<220> FEATURE:
<223> OTHER INFORMATION: Sunfast Blue binding peptide

<400> SEQUENCE: 119

Asn Tyr Pro Thr Gln Ala Pro
1               5

<210> SEQ ID NO 120
<211> LENGTH: 7
<212> TYPE: PRT
<213> ORGANISM: artificial sequence
<220> FEATURE:
<223> OTHER INFORMATION: Sunfast Blue binding peptide

<400> SEQUENCE: 120

Lys Cys Cys Tyr Ser Val Gly
1               5

<210> SEQ ID NO 121
<211> LENGTH: 12
<212> TYPE: PRT
<213> ORGANISM: artificial sequence
<220> FEATURE:
<223> OTHER INFORMATION: Sunfast Blue binding peptide

<400> SEQUENCE: 121

Arg His Asp Leu Asn Thr Trp Leu Pro Pro Val Lys
1               5                   10

<210> SEQ ID NO 122
<211> LENGTH: 12
<212> TYPE: PRT
```

<213> ORGANISM: artificial sequence
<220> FEATURE:
<223> OTHER INFORMATION: Sunfast Blue binding peptide

<400> SEQUENCE: 122

Glu Ile Ser Leu Pro Ala Lys Leu Pro Ser Ala Ser
1               5                   10

<210> SEQ ID NO 123
<211> LENGTH: 12
<212> TYPE: PRT
<213> ORGANISM: artificial sequence
<220> FEATURE:
<223> OTHER INFORMATION: Sunfast Blue binding peptide

<400> SEQUENCE: 123

Ser Val Ser Val Gly Met Lys Pro Ser Pro Arg Pro
1               5                   10

<210> SEQ ID NO 124
<211> LENGTH: 12
<212> TYPE: PRT
<213> ORGANISM: artificial sequence
<220> FEATURE:
<223> OTHER INFORMATION: Sunfast Blue binding peptide

<400> SEQUENCE: 124

Ser Asp Tyr Val Gly Met Arg Pro Ser Pro Arg His
1               5                   10

<210> SEQ ID NO 125
<211> LENGTH: 12
<212> TYPE: PRT
<213> ORGANISM: artificial sequence
<220> FEATURE:
<223> OTHER INFORMATION: Sunfast Blue binding peptide

<400> SEQUENCE: 125

Ser Asp Tyr Val Gly Met Arg Leu Ser Pro Ser Gln
1               5                   10

<210> SEQ ID NO 126
<211> LENGTH: 12
<212> TYPE: PRT
<213> ORGANISM: artificial sequence
<220> FEATURE:
<223> OTHER INFORMATION: Sunfast Blue binding peptide

<400> SEQUENCE: 126

Ser Val Ser Val Gly Ile Gln Pro Ser Pro Arg Pro
1               5                   10

<210> SEQ ID NO 127
<211> LENGTH: 12
<212> TYPE: PRT
<213> ORGANISM: artificial sequence
<220> FEATURE:
<223> OTHER INFORMATION: Sunfast Blue binding peptide

<400> SEQUENCE: 127

Tyr Val Ser Val Gly Ile Lys Pro Ser Pro Arg Pro
1               5                   10

<210> SEQ ID NO 128
<211> LENGTH: 12
<212> TYPE: PRT
<213> ORGANISM: artificial sequence
<220> FEATURE:

<223> OTHER INFORMATION: Sunfast Blue binding peptide

<400> SEQUENCE: 128

Tyr Val Cys Glu Gly Ile His Pro Cys Pro Arg Pro
1               5                   10

<210> SEQ ID NO 129
<211> LENGTH: 7
<212> TYPE: PRT
<213> ORGANISM: artificial sequence
<220> FEATURE:
<223> OTHER INFORMATION: Cellulose binding peptide

<400> SEQUENCE: 129

Val Pro Arg Val Thr Ser Ile
1               5

<210> SEQ ID NO 130
<211> LENGTH: 7
<212> TYPE: PRT
<213> ORGANISM: artificial sequence
<220> FEATURE:
<223> OTHER INFORMATION: Cellulose binding peptide

<400> SEQUENCE: 130

Met Ala Asn His Asn Leu Ser
1               5

<210> SEQ ID NO 131
<211> LENGTH: 7
<212> TYPE: PRT
<213> ORGANISM: artificial sequence
<220> FEATURE:
<223> OTHER INFORMATION: Cellulose binding peptide

<400> SEQUENCE: 131

Phe His Glu Asn Trp Pro Ser
1               5

<210> SEQ ID NO 132
<211> LENGTH: 12
<212> TYPE: PRT
<213> ORGANISM: artificial sequence
<220> FEATURE:
<223> OTHER INFORMATION: Cellulose binding peptide

<400> SEQUENCE: 132

Thr His Lys Thr Ser Thr Gln Arg Leu Leu Ala Ala
1               5                   10

<210> SEQ ID NO 133
<211> LENGTH: 12
<212> TYPE: PRT
<213> ORGANISM: artificial sequence
<220> FEATURE:
<223> OTHER INFORMATION: Cellulose binding peptide

<400> SEQUENCE: 133

Lys Cys Cys Tyr Val Asn Val Gly Ser Val Phe Ser
1               5                   10

<210> SEQ ID NO 134
<211> LENGTH: 12
<212> TYPE: PRT
<213> ORGANISM: artificial sequence
<220> FEATURE:
<223> OTHER INFORMATION: Cellulose binding peptide

```
<400> SEQUENCE: 134

Ala His Met Gln Phe Arg Thr Ser Leu Thr Pro His
1               5                   10

<210> SEQ ID NO 135
<211> LENGTH: 12
<212> TYPE: PRT
<213> ORGANISM: artificial sequence
<220> FEATURE:
<223> OTHER INFORMATION: Poly(ethylene terephthalate) binding peptide

<400> SEQUENCE: 135

Gly Thr Ser Asp His Met Ile Met Pro Phe Phe Asn
1               5                   10

<210> SEQ ID NO 136
<211> LENGTH: 12
<212> TYPE: PRT
<213> ORGANISM: artificial sequence
<220> FEATURE:
<223> OTHER INFORMATION: Poly(methyl methacrylate) binding peptide

<400> SEQUENCE: 136

Ile Pro Trp Trp Asn Ile Arg Ala Pro Leu Asn Ala
1               5                   10

<210> SEQ ID NO 137
<211> LENGTH: 12
<212> TYPE: PRT
<213> ORGANISM: artificial sequence
<220> FEATURE:
<223> OTHER INFORMATION: Poly(methyl methacrylate) binding peptide

<400> SEQUENCE: 137

Thr Ala Val Met Asn Val Val Asn Asn Gln Leu Ser
1               5                   10

<210> SEQ ID NO 138
<211> LENGTH: 12
<212> TYPE: PRT
<213> ORGANISM: artificial sequence
<220> FEATURE:
<223> OTHER INFORMATION: Poly(methyl methacrylate) binding peptide

<400> SEQUENCE: 138

Val Pro Trp Trp Ala Pro Ser Lys Leu Ser Met Gln
1               5                   10

<210> SEQ ID NO 139
<211> LENGTH: 12
<212> TYPE: PRT
<213> ORGANISM: artificial sequence
<220> FEATURE:
<223> OTHER INFORMATION: Poly(methyl methacrylate) binding peptide

<400> SEQUENCE: 139

Met Val Met Ala Pro His Thr Pro Arg Ala Arg Ser
1               5                   10

<210> SEQ ID NO 140
<211> LENGTH: 12
<212> TYPE: PRT
<213> ORGANISM: artificial sequence
<220> FEATURE:
<223> OTHER INFORMATION: Poly(methyl methacrylate) binding peptide

<400> SEQUENCE: 140
```

```
Thr Tyr Pro Asn Trp Ala His Leu Leu Ser His Tyr
1               5                   10
```

<210> SEQ ID NO 141
<211> LENGTH: 7
<212> TYPE: PRT
<213> ORGANISM: artificial sequence
<220> FEATURE:
<223> OTHER INFORMATION: Poly(methyl methacrylate) binding peptide

<400> SEQUENCE: 141

```
Thr Pro Trp Trp Arg Ile Thr
1               5
```

<210> SEQ ID NO 142
<211> LENGTH: 7
<212> TYPE: PRT
<213> ORGANISM: artificial sequence
<220> FEATURE:
<223> OTHER INFORMATION: Poly(methyl methacrylate) binding peptide

<400> SEQUENCE: 142

```
Asp Leu Thr Leu Pro Phe His
1               5
```

<210> SEQ ID NO 143
<211> LENGTH: 7
<212> TYPE: PRT
<213> ORGANISM: artificial sequence
<220> FEATURE:
<223> OTHER INFORMATION: Poly(methyl methacrylate) binding peptide

<400> SEQUENCE: 143

```
Gly Thr Ser Ile Pro Ala Met
1               5
```

<210> SEQ ID NO 144
<211> LENGTH: 7
<212> TYPE: PRT
<213> ORGANISM: artificial sequence
<220> FEATURE:
<223> OTHER INFORMATION: Poly(methyl methacrylate) binding peptide

<400> SEQUENCE: 144

```
His His Lys His Val Val Ala
1               5
```

<210> SEQ ID NO 145
<211> LENGTH: 7
<212> TYPE: PRT
<213> ORGANISM: artificial sequence
<220> FEATURE:
<223> OTHER INFORMATION: Poly(methyl methacrylate) binding peptide

<400> SEQUENCE: 145

```
His His His Lys His Phe Met
1               5
```

<210> SEQ ID NO 146
<211> LENGTH: 7
<212> TYPE: PRT
<213> ORGANISM: artificial sequence
<220> FEATURE:
<223> OTHER INFORMATION: Poly(methyl methacrylate) binding peptide

<400> SEQUENCE: 146

```
His His His Arg His Gln Gly
1               5
```

```
<210> SEQ ID NO 147
<211> LENGTH: 7
<212> TYPE: PRT
<213> ORGANISM: artificial sequence
<220> FEATURE:
<223> OTHER INFORMATION: Poly(methyl methacrylate) binding peptide

<400> SEQUENCE: 147

His His Trp His Ala Pro Arg
1               5

<210> SEQ ID NO 148
<211> LENGTH: 7
<212> TYPE: PRT
<213> ORGANISM: artificial sequence
<220> FEATURE:
<223> OTHER INFORMATION: Nylon binding peptide

<400> SEQUENCE: 148

Lys Thr Pro Pro Thr Arg Pro
1               5

<210> SEQ ID NO 149
<211> LENGTH: 7
<212> TYPE: PRT
<213> ORGANISM: artificial sequence
<220> FEATURE:
<223> OTHER INFORMATION: Nylon binding peptide

<400> SEQUENCE: 149

Val Ile Asn Pro Asn Leu Asp
1               5

<210> SEQ ID NO 150
<211> LENGTH: 7
<212> TYPE: PRT
<213> ORGANISM: artificial sequence
<220> FEATURE:
<223> OTHER INFORMATION: Nylon binding peptide

<400> SEQUENCE: 150

Lys Val Trp Ile Val Ser Thr
1               5

<210> SEQ ID NO 151
<211> LENGTH: 7
<212> TYPE: PRT
<213> ORGANISM: artificial sequence
<220> FEATURE:
<223> OTHER INFORMATION: Nylon binding peptide

<400> SEQUENCE: 151

Ala Glu Pro Val Ala Met Leu
1               5

<210> SEQ ID NO 152
<211> LENGTH: 7
<212> TYPE: PRT
<213> ORGANISM: artificial sequence
<220> FEATURE:
<223> OTHER INFORMATION: Nylon binding peptide

<400> SEQUENCE: 152

Ala Glu Leu Val Ala Met Leu
1               5
```

```
<210> SEQ ID NO 153
<211> LENGTH: 7
<212> TYPE: PRT
<213> ORGANISM: artificial sequence
<220> FEATURE:
<223> OTHER INFORMATION: Nylon binding peptide

<400> SEQUENCE: 153

His Ser Leu Arg Leu Asp Trp
1               5

<210> SEQ ID NO 154
<211> LENGTH: 12
<212> TYPE: PRT
<213> ORGANISM: artificial sequence
<220> FEATURE:
<223> OTHER INFORMATION: Poly(tetrafluoroethylene) binding peptide

<400> SEQUENCE: 154

Glu Ser Ser Tyr Ser Trp Ser Pro Ala Arg Leu Ser
1               5                   10

<210> SEQ ID NO 155
<211> LENGTH: 12
<212> TYPE: PRT
<213> ORGANISM: artificial sequence
<220> FEATURE:
<223> OTHER INFORMATION: Poly(tetrafluoroethylene) binding peptide

<400> SEQUENCE: 155

Gly Pro Leu Lys Leu Leu His Ala Trp Trp Gln Pro
1               5                   10

<210> SEQ ID NO 156
<211> LENGTH: 7
<212> TYPE: PRT
<213> ORGANISM: artificial sequence
<220> FEATURE:
<223> OTHER INFORMATION: Poly(tetrafluoroethylene) binding peptide

<400> SEQUENCE: 156

Asn Ala Leu Thr Arg Pro Val
1               5

<210> SEQ ID NO 157
<211> LENGTH: 7
<212> TYPE: PRT
<213> ORGANISM: artificial sequence
<220> FEATURE:
<223> OTHER INFORMATION: Poly(tetrafluoroethylene) binding peptide

<400> SEQUENCE: 157

Ser Ala Pro Ser Ser Lys Asn
1               5

<210> SEQ ID NO 158
<211> LENGTH: 12
<212> TYPE: PRT
<213> ORGANISM: artificial sequence
<220> FEATURE:
<223> OTHER INFORMATION: Poly(tetrafluoroethylene) binding peptide

<400> SEQUENCE: 158

Ser Val Ser Val Gly Met Lys Pro Ser Pro Arg Pro
1               5                   10

<210> SEQ ID NO 159
<211> LENGTH: 12
```

```
<212> TYPE: PRT
<213> ORGANISM: artificial sequence
<220> FEATURE:
<223> OTHER INFORMATION: Poly(tetrafluoroethylene) binding peptide

<400> SEQUENCE: 159

Ser Tyr Tyr Ser Leu Pro Pro Ile Phe His Ile Pro
1               5                   10

<210> SEQ ID NO 160
<211> LENGTH: 12
<212> TYPE: PRT
<213> ORGANISM: artificial sequence
<220> FEATURE:
<223> OTHER INFORMATION: Poly(tetrafluoroethylene) binding peptide

<400> SEQUENCE: 160

Thr Phe Thr Pro Tyr Ser Ile Thr His Ala Leu Leu
1               5                   10

<210> SEQ ID NO 161
<211> LENGTH: 12
<212> TYPE: PRT
<213> ORGANISM: artificial sequence
<220> FEATURE:
<223> OTHER INFORMATION: Poly(tetrafluoroethylene) binding peptide

<400> SEQUENCE: 161

Thr Met Gly Phe Thr Ala Pro Arg Phe Pro His Tyr
1               5                   10

<210> SEQ ID NO 162
<211> LENGTH: 12
<212> TYPE: PRT
<213> ORGANISM: artificial sequence
<220> FEATURE:
<223> OTHER INFORMATION: Poly(tetrafluoroethylene) binding peptide

<400> SEQUENCE: 162

Thr Asn Pro Phe Pro Pro Pro Ser Ser Pro Ala
1               5                   10

<210> SEQ ID NO 163
<211> LENGTH: 27
<212> TYPE: PRT
<213> ORGANISM: artificial sequence
<220> FEATURE:
<223> OTHER INFORMATION: clay binding peptide

<400> SEQUENCE: 163

Gly His Gly Ser Pro Ser Asn Ser His His Gly Ser Lys Lys Cys Asp
1               5                   10                  15

Met Gly Asn Ser Arg Ala Lys Cys Lys Arg Leu
            20                  25

<210> SEQ ID NO 164
<211> LENGTH: 27
<212> TYPE: PRT
<213> ORGANISM: artificial sequence
<220> FEATURE:
<223> OTHER INFORMATION: clay binding peptide

<400> SEQUENCE: 164

Ser Asp Arg His Asn Leu Arg Asn Ser Trp Ser Ile Ser Arg His Cys
1               5                   10                  15

Arg Arg Lys Gln Gly Arg Cys Leu Pro Ala His
            20                  25
```

```
<210> SEQ ID NO 165
<211> LENGTH: 27
<212> TYPE: PRT
<213> ORGANISM: artificial sequence
<220> FEATURE:
<223> OTHER INFORMATION: clay binding peptide

<400> SEQUENCE: 165

Lys Lys Ser Asn Lys Gly His His Pro Ser Ser Lys Gly Lys Gly Pro
1               5                   10                  15

Pro Trp Ser Glu Trp Asp Lys Lys Asn Gly Pro
            20                  25

<210> SEQ ID NO 166
<211> LENGTH: 27
<212> TYPE: PRT
<213> ORGANISM: artificial sequence
<220> FEATURE:
<223> OTHER INFORMATION: clay binding peptide

<400> SEQUENCE: 166

Lys Lys Ser Asn Lys Gly Pro His Pro Ser Ser Lys Gly Lys Gly Pro
1               5                   10                  15

Pro Trp Ser Glu Trp Asp Lys Lys Asn Gly Pro
            20                  25

<210> SEQ ID NO 167
<211> LENGTH: 22
<212> TYPE: PRT
<213> ORGANISM: artificial sequence
<220> FEATURE:
<223> OTHER INFORMATION: clay binding peptide

<400> SEQUENCE: 167

Val Gly Arg His His Ser Lys Ala Lys Gln Lys Arg Pro His Gly Gly
1               5                   10                  15

Lys Gly Gln Asn Lys Asn
            20

<210> SEQ ID NO 168
<211> LENGTH: 22
<212> TYPE: PRT
<213> ORGANISM: artificial sequence
<220> FEATURE:
<223> OTHER INFORMATION: clay binding peptide

<400> SEQUENCE: 168

Val Gly Arg His His Pro Lys Ala Lys Gln Lys Arg Pro His Gly Gly
1               5                   10                  15

Lys Gly Gln Asn Lys Asn
            20

<210> SEQ ID NO 169
<211> LENGTH: 17
<212> TYPE: PRT
<213> ORGANISM: artificial sequence
<220> FEATURE:
<223> OTHER INFORMATION: clay binding peptide

<400> SEQUENCE: 169

Gly Arg Arg Pro Arg Ala Arg Gly Arg Ser Arg Arg Gly Ser Thr Lys
1               5                   10                  15

Thr
```

```
<210> SEQ ID NO 170
<211> LENGTH: 19
<212> TYPE: PRT
<213> ORGANISM: artificial sequence
<220> FEATURE:
<223> OTHER INFORMATION: clay binding peptide

<400> SEQUENCE: 170

Leu Gly Val Ile Arg Asn His Val Val Arg Gly Arg Arg His His Gln
1               5                   10                  15

His Val Arg

<210> SEQ ID NO 171
<211> LENGTH: 27
<212> TYPE: PRT
<213> ORGANISM: artificial sequence
<220> FEATURE:
<223> OTHER INFORMATION: clay binding peptide

<400> SEQUENCE: 171

Gln Pro Gly Arg Pro Thr Glu Val His Pro Glu Leu Val Arg Lys Ser
1               5                   10                  15

Ala Tyr Leu Val Asn Pro Ser Glu Asp Ile Arg
            20                  25

<210> SEQ ID NO 172
<211> LENGTH: 27
<212> TYPE: PRT
<213> ORGANISM: artificial sequence
<220> FEATURE:
<223> OTHER INFORMATION: clay binding peptide

<400> SEQUENCE: 172

His Arg Ser Glu Lys Pro Lys Asn Val Lys Tyr Lys Arg Gly Tyr Trp
1               5                   10                  15

Glu Arg Gly Asn Gln Lys Lys His Gly Pro Gly
            20                  25

<210> SEQ ID NO 173
<211> LENGTH: 27
<212> TYPE: PRT
<213> ORGANISM: artificial sequence
<220> FEATURE:
<223> OTHER INFORMATION: clay binding peptide

<400> SEQUENCE: 173

Gly Ser His Lys Arg Arg Gly Ser Tyr Ala Leu Leu Arg Thr Arg Gly
1               5                   10                  15

Val Gly Arg Gln Ala Glu Leu Glu His Leu Leu
            20                  25

<210> SEQ ID NO 174
<211> LENGTH: 27
<212> TYPE: PRT
<213> ORGANISM: artificial sequence
<220> FEATURE:
<223> OTHER INFORMATION: clay binding peptide

<400> SEQUENCE: 174

Val Gly Glu Lys Pro Arg Arg Lys Ser Lys Gly Ala Lys Ala Lys Lys
1               5                   10                  15

Ala Arg Thr Lys Glu Glu Lys Leu Pro Lys Asn
            20                  25
```

```
<210> SEQ ID NO 175
<211> LENGTH: 27
<212> TYPE: PRT
<213> ORGANISM: artificial sequence
<220> FEATURE:
<223> OTHER INFORMATION: clay binding peptide

<400> SEQUENCE: 175

Asn Lys Gly His Lys Gln Ser Gly Ser Pro Arg His Ser Asn Lys Lys
1               5                   10                  15

Glu Lys Lys Thr Gln Gln Lys Arg Gly Gln Pro
            20                  25

<210> SEQ ID NO 176
<211> LENGTH: 27
<212> TYPE: PRT
<213> ORGANISM: artificial sequence
<220> FEATURE:
<223> OTHER INFORMATION: clay binding peptide

<400> SEQUENCE: 176

His Trp Gly Ser Gln His Lys Thr Gly Leu Arg Asn His Lys Arg Ser
1               5                   10                  15

Arg Arg Asp Ser Leu Gly Lys Arg Gly Thr Asp
            20                  25

<210> SEQ ID NO 177
<211> LENGTH: 27
<212> TYPE: PRT
<213> ORGANISM: artificial sequence
<220> FEATURE:
<223> OTHER INFORMATION: clay binding peptide

<400> SEQUENCE: 177

Lys Gly Trp Gly Ser Ser Ser Gly Pro Pro Gly Leu Thr Gly Lys Ala
1               5                   10                  15

Leu Gly Lys Gly Arg Leu Lys Pro Lys Lys Lys
            20                  25

<210> SEQ ID NO 178
<211> LENGTH: 24
<212> TYPE: PRT
<213> ORGANISM: artificial sequence
<220> FEATURE:
<223> OTHER INFORMATION: clay binding peptide

<400> SEQUENCE: 178

Ser Ser Lys Ser Gly Ala Pro Phe Arg Val Pro Ile Cys Phe Thr Ala
1               5                   10                  15

Pro Arg Pro Gln Lys Thr Leu Gly
            20

<210> SEQ ID NO 179
<211> LENGTH: 5
<212> TYPE: PRT
<213> ORGANISM: artificial sequence
<220> FEATURE:
<223> OTHER INFORMATION: Caspase-3 cleavage sequence
<220> FEATURE:
<221> NAME/KEY: MISC_FEATURE
<222> LOCATION: (5)..(5)
<223> OTHER INFORMATION: Xaa = any amino acid but Pro, Glu, Asp, Gln,
      Lys, and Arg

<400> SEQUENCE: 179

Asp Met Gln Asp Xaa
1               5
```

<210> SEQ ID NO 180
<211> LENGTH: 6037
<212> TYPE: DNA
<213> ORGANISM: artificial sequence
<220> FEATURE:
<223> OTHER INFORMATION: plasmid

<400> SEQUENCE: 180

| | | | | | |
|---|---|---|---|---|---|
| aagaaaccaa | ttgtccatat | tgcatcagac | attgccgtca | ctgcgtcttt | tactggctct | 60 |
| tctcgctaac | caaaccggta | accccgctta | ttaaaagcat | tctgtaacaa | agcgggacca | 120 |
| aagccatgac | aaaaacgcgt | aacaaaagtg | tctataatca | cggcagaaaa | gtccacattg | 180 |
| attatttgca | cggcgtcaca | ctttgctatg | ccatagcatt | tttatccata | agattagcgg | 240 |
| atcttacctg | acgcttttta | tcgcaactct | ctactgtttc | tccatacccg | ttttttgggc | 300 |
| taacaggagg | aattacatat | ggctagctgc | ggtcaacaac | gttttcaatg | caattcgaa | 360 |
| caacagccgc | gttgcggcca | gcaacgcttc | caatggcagt | tgaacagca | accgcgttgc | 420 |
| ggtcagcaac | gtttccagtg | gcaatttgaa | caacagccag | agtgcggcca | gcagcgcttt | 480 |
| cagtggcagt | tcgagcagca | gccgtgcgga | tccgaccctg | gcattccgtg | gtggaacatt | 540 |
| cgtgctcctc | tgaatgcagg | tgcgggcatc | ccttggtgga | atattcgtgc | tccgctgaac | 600 |
| gccggtggtt | ccgtccgggt | agcggtggt | aatacttctc | agctgtccac | gggtggcggt | 660 |
| aacactagcc | agctgagcac | gggcggccct | aaaaagccgg | gcgacccggg | tattccgtgg | 720 |
| tggaatatcc | gtgccccgct | gaacgcaggt | gccggcatcc | cgtggtggaa | cattcgtgca | 780 |
| cctctgaatg | ctggtggttc | cggtccaggc | tctggcggca | cacttccca | gctgtccacc | 840 |
| ggcggtggca | acaccagcca | gctgtctact | ggtggtccga | gaaaccggg | tgactaataa | 900 |
| ggcgcgccga | cccagctttc | ttgtacaaag | tggttgattc | gaggctgcta | caaagcccg | 960 |
| aaaggaagct | gagttggctg | ctgccaccgc | tgagcaataa | ctagcataac | cccttggggc | 1020 |
| ctctaaacgg | gtcttgaggg | gtttttgct | gaaaggagga | actatatccg | gatatccaca | 1080 |
| ggacgggtgt | ggtcgccatg | atcgcgtagt | cgatagtggc | tccaagtagc | gaagcgagca | 1140 |
| ggactgggcg | gcggccaaag | cggtcggaca | gtgctccgag | aacgggtgcg | catagaaatt | 1200 |
| gcatcaacgc | atatagcgct | agcagcacgc | catagtgact | ggcgatgctg | tcggaatgga | 1260 |
| cgatatcccg | caagaggccc | ggcagtaccg | gcataaccaa | gcctatgcct | acagcatcca | 1320 |
| gggtgacggt | gccgaggatg | acgatgagcg | cattgttaga | tttcatacac | ggtgcctgac | 1380 |
| tgcgttagca | atttaactgt | gataaactac | cgcattaaag | cttgcagtgg | cggttttcat | 1440 |
| ggcttgttat | gactgttttt | ttggggtaca | gtctatgcct | cgggcatcca | agcagcaagc | 1500 |
| gcgttacgcc | gtgggtcgat | gtttgatgtt | atggagcagc | aacgatgtta | cgcagcaggg | 1560 |
| cagtcgccct | aaaacaaagt | taaacatcat | gagggaagcg | gtgatcgccg | aagtatcgac | 1620 |
| tcaactatca | gaggtagttg | gcgtcatcga | gcgccatctc | gaaccgacgt | tgctggccgt | 1680 |
| acatttgtac | ggctccgcag | tggatggcgg | cctgaagcca | cacagtgata | ttgatttgct | 1740 |
| ggttacggtg | accgtaaggc | ttgatgaaac | aacgcggcga | gctttgatca | cgacctttt | 1800 |
| ggaaacttcg | gcttcccctg | gagagagcga | gattctccgc | gctgtagaag | tcaccattgt | 1860 |
| tgtgcacgac | gacatcattc | cgtggcgtta | tccagctaag | cgcgaactgc | aatttggaga | 1920 |
| atggcagcgc | aatgacattc | ttgcaggtat | cttcgagcca | gccacgatcg | acattgatct | 1980 |
| ggctatcttg | ctgacaaaag | caagagaaca | tagcgttgcc | ttggtaggtc | cagcggcgga | 2040 |
| ggaactcttt | gatccggttc | ctgaacagga | tctatttgag | gcgctaaatg | aaaccttaac | 2100 |

```
gctatggaac tcgccgcccg actgggctgg cgatgagcga aatgtagtgc ttacgttgtc   2160
ccgcatttgg tacagcgcag taaccggcaa aatcgcgccg aaggatgtcg ctgccgactg   2220
ggcaatggag cgcctgccgg cccagtatca gcccgtcata cttgaagcta gacaggctta   2280
tcttggacaa gaagaagatc gcttggcctc gcgcgcagat cagttggaag aatttgtcca   2340
ctacgtgaaa ggcgagatca ccaaggtagt cggcaaataa tgtctaacaa ttcgttcaag   2400
cttggctgtt ttggcggatg agagaagatt ttcagcctga tacagattaa atcagaacgc   2460
agaagcggtc tgataaaaca gaatttgcct ggcggcagta gcgcggtggt cccacctgac   2520
cccatgccga actcagaagt gaaacgccgt agcgccgatg gtagtgtggg gtctccccat   2580
gcgagagtag ggaactgcca ggcatcaaat aaaacgaaag gctcagtcga aagactgggc   2640
cttccgtttt atctgttgtt tgtcggtgaa cgctctcctg agtaggacaa atccgccggg   2700
agcggatttg aacgttgcga agcaacggcc cggagggtgg cgggcaggac gcccgccata   2760
aactgccagg catcaaatta agcagaaggc catcctgacg gatggccttt ttgcgtttct   2820
acaaactctt ttgtttattt ttctaaatac attcaaatat gtatccgctc atgagacaat   2880
aaccctgata aatgcttcaa taatattgaa aaaggaagag tatgagtatt caacatttcc   2940
gtgtcgccct tattcccttt tttgcggcat tttgccttcc tgttttgct cacccagaaa   3000 cgctggtgaa agtaaaagat gctgaagatc agttgggtgc acgagtgggt tacatcgaac   3060
tggatctcaa cagcggtaag atccttgaga gttttcgccc cgaagaacgt tttccaatga   3120
tgagcacttt taaagttctg ctatgtggcg cggtattatc ccgtgttgac gccgggcaag   3180
agcaactcgg tcgccgcata cactattctc agaatgactt ggttgagtac tcaccagtca   3240
cagaaaagca tcttacggat ggcatgacag taagagaatt atgcagtgct gccataacca   3300
tgagtgataa cactgcggcc aacttacttc tgacaacgat cggaggaccg aaggagctaa   3360 ccgcttttt gcacaacatg ggggatcatg taactcgcct tgatcgttgg gaaccggagc   3420
tgaatgaagc cataccaaac gacgagcgtg acaccacgat gcctgtagca atggcaacaa   3480
cgttgcgcaa actattaact ggcgaactac ttactctagc ttcccggcaa caattaatag   3540
actggatgga ggcggataaa gttgcaggac cacttctgcg ctcggccctt ccggctggct   3600
ggtttattgc tgataaatct ggagccggtg agcgtgggtc tcgcggtatc attgcagcac   3660
tggggccaga tggtaagccc tcccgtatcg tagttatcta cacgacgggg agtcaggcaa   3720
ctatggatga acgaaataga cagatcgctg agataggtgc ctcactgatt aagcattggt   3780
aactgtcaga ccaagtttac tcatatatac tttagattga tttaaaactt catttttaat   3840
ttaaaaggat ctaggtgaag atccttttg ataatctcat gaccaaaatc ccttaacgtg   3900
agttttcgtt ccactgagcg tcagaccccg tagaaaagat caaaggatct tcttgagatc   3960
ctttttttct gcgcgtaatc tgctgcttgc aaacaaaaaa accaccgcta ccagcggtgg   4020
tttgtttgcc ggatcaagag ctaccaactc tttttccgaa ggtaactggc ttcagcagag   4080
cgcagatacc aaatactgtc cttctagtgt agccgtagtt aggccaccac ttcaagaact   4140
ctgtagcacc gcctacatac ctcgctctgc taatcctgtt accagtggct gctgccagtg   4200
gcgataagtc gtgtcttacc gggttggact caagacgata gttaccggat aaggcgcagc   4260
ggtcgggctg aacggggggt tcgtgcacac agcccagctt ggagcgaacg acctacaccg   4320
aactgagata cctacagcgt gagctatgag aaagcgccac gcttcccgaa gggagaaagg   4380
cggacaggta tccggtaagc ggcagggtcg gaacaggaga gcgcacgagg gagcttccag   4440
ggggaaacgc ctggtatctt tatagtcctg tcgggtttcg ccacctctga cttgagcgtc   4500
```

```
gattttttgtg atgctcgtca gggggggcgga gcctatggaa aaacgccagc aacgcggcct    4560
ttttacggtt cctggccttt tgctggcctt ttgctcacat gttctttcct gcgttatccc    4620
ctgattctgt ggataaccgt attaccgcct ttgagtgagc tgataccgct cgccgcagcc    4680
gaacgaccga gcgcagcgag tcagtgagcg aggaagcgga agagcgcctg atgcggtatt    4740
ttctccttac gcatctgtgc ggtatttcac accgcatata tggtgcactc tcagtacaat    4800
ctgctctgat gccgcatagt taagccagta tacactccgc tatcgctacg tgactgggtc    4860
atggctgcgc cccgacaccc gccaacaccc gctgacgcgc cctgacgggc ttgtctgctc    4920
ccggcatccg cttacagaca agctgtgacc gtctccggga gctgcatgtg tcagaggttt    4980
tcaccgtcat caccgaaacg cgcgaggcag cagatcaatt cgcgcgcgaa ggcgaagcgg    5040
catgcataat gtgcctgtca aatggacgaa gcagggattc tgcaaaccct atgctactcc    5100
gtcaagccgt caattgtctg attcgttacc aattatgaca acttgacggc tacatcattc    5160 acttttctt cacaaccggc acggaactcg ctcgggctgg ccccggtgca ttttttaaat    5220
acccgcgaga aatagagttg atcgtcaaaa ccaacattgc gaccgacggt ggcgataggc    5280
atccgggtgg tgctcaaaag cagcttcgcc tggctgatac gttggtcctc gcgccagctt    5340
aagacgctaa tccctaactg ctggcggaaa agatgtgaca acgcgacgg cgacaagcaa    5400 acatgctgtg cgacgctggc gatatcaaaa ttgctgtctg ccaggtgatc gctgatgtac    5460
tgacaagcct cgcgtacccg attatccatc ggtggatgga gcgactcgtt aatcgcttcc    5520
atgcgccgca gtaacaattg ctcaagcaga tttatcgcca gcagctccga atagcgccct    5580
tccccttgcc cggcgttaat gatttgccca acaggtcgc tgaaatgcgg ctggtgcgct    5640
tcatccgggc gaaagaaccc cgtattggca atatattgacg gccagttaag ccattcatgc    5700
cagtaggcgc gcggacgaaa gtaaacccac tggtgatacc attcgcgagc ctccggatga    5760
cgaccgtagt gatgaatctc tcctggcggg aacagcaaaa tatcacccgg tcggcaaaca    5820
aattctcgtc cctgattttt caccacccc tgaccgcgaa tggtgagatt gagaatataa    5880
cctttcattc ccagcggtcg gtcgataaaa aaatcgagat aaccgttggc ctcaatcggc    5940
gttaaacccg ccaccagatg ggcattaaac gagtatcccg gcagcagggg atcattttgc    6000
gcttcagcca tacttttcat actcccgcca ttcagag                            6037
```

<210> SEQ ID NO 181
<211> LENGTH: 189
<212> TYPE: DNA
<213> ORGANISM: artificial sequence
<220> FEATURE:
<223> OTHER INFORMATION: inclusion body tag IBT139(5C)

<400> SEQUENCE: 181

```
atggctagct gcggtcaaca acgttttcaa tggcaattcg aacaacagcc gcgttgcggc     60
cagcaacgct tccaatggca gtttgaacag caaccgcgtt gcggtcagca acgttttccag   120 tggcaatttg aacaacagcc agagtgcggc cagcagcgct ttcagtggca gttcgagcag   180
cagccgtgc                                                            189
```

<210> SEQ ID NO 182
<211> LENGTH: 63
<212> TYPE: PRT
<213> ORGANISM: artificial sequence
<220> FEATURE:
<223> OTHER INFORMATION: Inclusion body tag IBT139(5C)

<400> SEQUENCE: 182

```
Met Ala Ser Cys Gly Gln Gln Arg Phe Gln Trp Gln Phe Glu Gln Gln
1               5                   10                  15

Pro Arg Cys Gly Gln Gln Arg Phe Gln Trp Gln Phe Glu Gln Gln Pro
                20                  25                  30

Arg Cys Gly Gln Gln Arg Phe Gln Trp Gln Phe Glu Gln Gln Pro Glu
            35                  40                  45

Cys Gly Gln Gln Arg Phe Gln Trp Gln Phe Glu Gln Gln Pro Cys
        50                  55                  60
```

<210> SEQ ID NO 183
<211> LENGTH: 576
<212> TYPE: DNA
<213> ORGANISM: artificial sequence
<220> FEATURE:
<223> OTHER INFORMATION: synthetic fusion construct IBT139(5C).HC776124

<400> SEQUENCE: 183

```
atggctagct gcggtcaaca acgttttcaa tggcaattcg aacaacagcc gcgttgcggc    60
cagcaacgct ccaatggca gtttgaacag caaccgcgtt gcggtcagca cgtttccag    120
tggcaatttg aacaacagcc agagtgcggc cagcagcgct tcagtggca gttcgagcag    180
cagccgtgcg accctggcat tccgtggtgg aacattcgtg ctcctctgaa tgcaggtgcg    240
ggcatccctt ggtggaatat tcgtgctccg ctgaacgccg gtggtccgg tccgggtagc    300
ggtggtaata cttctcagct gtccacgggt ggcggtaaca ctagccagct gagcacgggc    360
ggccctaaaa agccgggcga cccgggtatt ccgtggtgga atatccgtgc ccgctgaac    420
gcaggtgccg gcatcccgtg gtggaacatt cgtgcacctc tgaatgctgg tggttccggt    480
ccaggctctg gcggcaacac ttcccagctg tccaccggcg gtggcaacac cagccagctg    540
tctactggtg gtccgaagaa accgggtgac taataa                              576
```

<210> SEQ ID NO 184
<211> LENGTH: 190
<212> TYPE: PRT
<213> ORGANISM: artificial sequence
<220> FEATURE:
<223> OTHER INFORMATION: synthetic fusion construct IBT139(5C).HC776124

<400> SEQUENCE: 184

```
Met Ala Ser Cys Gly Gln Gln Arg Phe Gln Trp Gln Phe Glu Gln Gln
1               5                   10                  15

Pro Arg Cys Gly Gln Gln Arg Phe Gln Trp Gln Phe Glu Gln Gln Pro
                20                  25                  30

Arg Cys Gly Gln Gln Arg Phe Gln Trp Gln Phe Glu Gln Gln Pro Glu
            35                  40                  45

Cys Gly Gln Gln Arg Phe Gln Trp Gln Phe Glu Gln Gln Pro Cys Asp
        50                  55                  60

Pro Gly Ile Pro Trp Trp Asn Ile Arg Ala Pro Leu Asn Ala Gly Ala
65                  70                  75                  80

Gly Ile Pro Trp Trp Asn Ile Arg Ala Pro Leu Asn Ala Gly Gly Ser
                85                  90                  95

Gly Pro Gly Ser Gly Gly Asn Thr Ser Gln Leu Ser Thr Gly Gly Gly
                100                 105                 110

Asn Thr Ser Gln Leu Ser Thr Gly Gly Pro Lys Lys Pro Gly Asp Pro
            115                 120                 125

Gly Ile Pro Trp Trp Asn Ile Arg Ala Pro Leu Asn Ala Gly Ala Gly
        130                 135                 140
```

```
Ile Pro Trp Trp Asn Ile Arg Ala Pro Leu Asn Ala Gly Gly Ser Gly
145                 150                 155                 160

Pro Gly Ser Gly Gly Asn Thr Ser Gln Leu Ser Thr Gly Gly Asn
            165                 170                 175

Thr Ser Gln Leu Ser Thr Gly Gly Pro Lys Lys Pro Gly Asp
        180                 185                 190

<210> SEQ ID NO 185
<211> LENGTH: 20
<212> TYPE: PRT
<213> ORGANISM: artificial sequence
<220> FEATURE:
<223> OTHER INFORMATION: Tooth-binding peptide

<400> SEQUENCE: 185

Ala His Pro Glu Ser Leu Gly Ile Lys Tyr Ala Leu Asp Gly Asn Ser
1               5                   10                  15

Asp Pro His Ala
        20

<210> SEQ ID NO 186
<211> LENGTH: 20
<212> TYPE: PRT
<213> ORGANISM: artificial sequence
<220> FEATURE:
<223> OTHER INFORMATION: Tooth-binding peptide

<400> SEQUENCE: 186

Ala Ser Val Ser Asn Tyr Pro Pro Ile His His Leu Ala Thr Ser Asn
1               5                   10                  15

Thr Thr Val Asn
        20

<210> SEQ ID NO 187
<211> LENGTH: 14
<212> TYPE: PRT
<213> ORGANISM: artificial sequence
<220> FEATURE:
<223> OTHER INFORMATION: Tooth-binding peptide

<400> SEQUENCE: 187

Asp Glu Cys Met Glu Pro Leu Asn Ala Ala His Cys Trp Arg
1               5                   10

<210> SEQ ID NO 188
<211> LENGTH: 14
<212> TYPE: PRT
<213> ORGANISM: artificial sequence
<220> FEATURE:
<223> OTHER INFORMATION: Tooth-binding peptide

<400> SEQUENCE: 188

Asp Glu Cys Met His Gly Ser Asp Val Glu Phe Cys Thr Ser
1               5                   10

<210> SEQ ID NO 189
<211> LENGTH: 14
<212> TYPE: PRT
<213> ORGANISM: artificial sequence
<220> FEATURE:
<223> OTHER INFORMATION: Tooth-binding peptide

<400> SEQUENCE: 189

Asp Leu Cys Ser Met Gln Met Met Asn Thr Gly Cys His Tyr
1               5                   10
```

```
<210> SEQ ID NO 190
<211> LENGTH: 14
<212> TYPE: PRT
<213> ORGANISM: artificial sequence
<220> FEATURE:
<223> OTHER INFORMATION: Tooth-binding peptide

<400> SEQUENCE: 190

Asp Leu Cys Ser Ser Pro Ser Thr Trp Gly Ser Cys Ile Arg
1               5                   10

<210> SEQ ID NO 191
<211> LENGTH: 20
<212> TYPE: PRT
<213> ORGANISM: artificial sequence
<220> FEATURE:
<223> OTHER INFORMATION: Tooth-binding peptide

<400> SEQUENCE: 191

Asp Pro Asn Glu Ser Asn Tyr Glu Asn Ala Thr Thr Val Ser Gln Pro
1               5                   10                  15

Thr Arg His Leu
            20

<210> SEQ ID NO 192
<211> LENGTH: 20
<212> TYPE: PRT
<213> ORGANISM: artificial sequence
<220> FEATURE:
<223> OTHER INFORMATION: Tooth-binding peptide

<400> SEQUENCE: 192

Glu Pro Thr His Pro Thr Met Arg Ala Gln Met His Gln Ser Leu Arg
1               5                   10                  15

Ser Ser Ser Pro
            20

<210> SEQ ID NO 193
<211> LENGTH: 20
<212> TYPE: PRT
<213> ORGANISM: artificial sequence
<220> FEATURE:
<223> OTHER INFORMATION: Tooth-binding peptide

<400> SEQUENCE: 193

Gly Asn Thr Asp Thr Thr Pro Pro Asn Ala Val Met Glu Pro Thr Val
1               5                   10                  15

Gln His Lys Trp
            20

<210> SEQ ID NO 194
<211> LENGTH: 15
<212> TYPE: PRT
<213> ORGANISM: artificial sequence
<220> FEATURE:
<223> OTHER INFORMATION: Tooth-binding peptide

<400> SEQUENCE: 194

Asn Gly Pro Asp Met Val Gln Ser Val Gly Lys His Lys Asn Ser
1               5                   10                  15

<210> SEQ ID NO 195
<211> LENGTH: 15
<212> TYPE: PRT
<213> ORGANISM: artificial sequence
<220> FEATURE:
```

<223> OTHER INFORMATION: Tooth-binding peptide

<400> SEQUENCE: 195

Asn Gly Pro Glu Val Arg Gln Ile Pro Ala Asn Phe Glu Lys Leu
1               5                   10                  15

<210> SEQ ID NO 196
<211> LENGTH: 20
<212> TYPE: PRT
<213> ORGANISM: artificial sequence
<220> FEATURE:
<223> OTHER INFORMATION: Tooth-binding peptide

<400> SEQUENCE: 196

Asn Asn Thr Ser Ala Asp Asn Pro Pro Glu Thr Asp Ser Lys His His
1               5                   10                  15

Leu Ser Met Ser
            20

<210> SEQ ID NO 197
<211> LENGTH: 20
<212> TYPE: PRT
<213> ORGANISM: artificial sequence
<220> FEATURE:
<223> OTHER INFORMATION: Tooth-binding peptide

<400> SEQUENCE: 197

Asn Asn Thr Trp Pro Glu Gly Ala Gly His Thr Met Pro Ser Thr Asn
1               5                   10                  15

Ile Arg Gln Ala
            20

<210> SEQ ID NO 198
<211> LENGTH: 20
<212> TYPE: PRT
<213> ORGANISM: artificial sequence
<220> FEATURE:
<223> OTHER INFORMATION: Tooth-binding peptide

<400> SEQUENCE: 198

Asn Pro Thr Ala Thr Pro His Met Lys Asp Pro Met His Ser Asn Ala
1               5                   10                  15

His Ser Ser Ala
            20

<210> SEQ ID NO 199
<211> LENGTH: 20
<212> TYPE: PRT
<213> ORGANISM: artificial sequence
<220> FEATURE:
<223> OTHER INFORMATION: Tooth-binding peptide

<400> SEQUENCE: 199

Asn Pro Thr Asp His Ile Pro Ala Asn Ser Thr Asn Ser Arg Val Ser
1               5                   10                  15

Lys Gly Asn Thr
            20

<210> SEQ ID NO 200
<211> LENGTH: 15
<212> TYPE: PRT
<213> ORGANISM: artificial sequence
<220> FEATURE:
<223> OTHER INFORMATION: Tooth-binding peptide

<400> SEQUENCE: 200

```
Asn Pro Thr Asp Ser Thr His Met Met His Ala Arg Asn His Glu
 1               5                  10                  15
```

<210> SEQ ID NO 201
<211> LENGTH: 14
<212> TYPE: PRT
<213> ORGANISM: artificial sequence
<220> FEATURE:
<223> OTHER INFORMATION: Tooth-binding peptide

<400> SEQUENCE: 201

```
Gln His Cys Ile Thr Glu Arg Leu His Pro Pro Cys Thr Lys
 1               5                  10
```

<210> SEQ ID NO 202
<211> LENGTH: 14
<212> TYPE: PRT
<213> ORGANISM: artificial sequence
<220> FEATURE:
<223> OTHER INFORMATION: Tooth-binding peptide

<400> SEQUENCE: 202

```
Thr Pro Cys Ala Pro Ala Ser Phe Asn Pro His Cys Ser Arg
 1               5                  10
```

<210> SEQ ID NO 203
<211> LENGTH: 14
<212> TYPE: PRT
<213> ORGANISM: artificial sequence
<220> FEATURE:
<223> OTHER INFORMATION: Tooth-binding peptide

<400> SEQUENCE: 203

```
Thr Pro Cys Ala Thr Tyr Pro His Phe Ser Gly Cys Arg Ala
 1               5                  10
```

<210> SEQ ID NO 204
<211> LENGTH: 20
<212> TYPE: PRT
<213> ORGANISM: artificial sequence
<220> FEATURE:
<223> OTHER INFORMATION: Tooth-binding peptide

<400> SEQUENCE: 204

```
Trp Cys Thr Asp Phe Cys Thr Arg Ser Thr Pro Thr Ser Thr Ser Arg
 1               5                  10                  15

Ser Thr Thr Ser
            20
```

<210> SEQ ID NO 205
<211> LENGTH: 20
<212> TYPE: PRT
<213> ORGANISM: artificial sequence
<220> FEATURE:
<223> OTHER INFORMATION: Tooth-binding peptide

<400> SEQUENCE: 205

```
Ala Pro Pro Leu Lys Thr Tyr Met Gln Glu Arg Glu Leu Thr Met Ser
 1               5                  10                  15

Gln Asn Lys Asp
            20
```

<210> SEQ ID NO 206
<211> LENGTH: 20
<212> TYPE: PRT
<213> ORGANISM: artificial sequence

```
<220> FEATURE:
<223> OTHER INFORMATION: Tooth-binding peptide

<400> SEQUENCE: 206

Glu Pro Pro Thr Arg Thr Arg Val Asn Asn His Thr Val Thr Val Gln
1               5                   10                  15

Ala Gln Gln His
            20

<210> SEQ ID NO 207
<211> LENGTH: 14
<212> TYPE: PRT
<213> ORGANISM: artificial sequence
<220> FEATURE:
<223> OTHER INFORMATION: Tooth-binding peptide

<400> SEQUENCE: 207

Gly Tyr Cys Leu Arg Gly Asp Glu Pro Ala Val Cys Ser Gly
1               5                   10

<210> SEQ ID NO 208
<211> LENGTH: 20
<212> TYPE: PRT
<213> ORGANISM: artificial sequence
<220> FEATURE:
<223> OTHER INFORMATION: Tooth-binding peptide

<400> SEQUENCE: 208

Leu Ser Ser Lys Asp Phe Gly Val Thr Asn Thr Asp Gln Arg Thr Tyr
1               5                   10                  15

Asp Tyr Thr Thr
            20

<210> SEQ ID NO 209
<211> LENGTH: 14
<212> TYPE: PRT
<213> ORGANISM: artificial sequence
<220> FEATURE:
<223> OTHER INFORMATION: Tooth-binding peptide

<400> SEQUENCE: 209

Asn Phe Cys Glu Thr Gln Leu Asp Leu Ser Val Cys Thr Val
1               5                   10

<210> SEQ ID NO 210
<211> LENGTH: 14
<212> TYPE: PRT
<213> ORGANISM: artificial sequence
<220> FEATURE:
<223> OTHER INFORMATION: Tooth-binding peptide

<400> SEQUENCE: 210

Asn Thr Cys Gln Pro Thr Lys Asn Ala Thr Pro Cys Ser Ala
1               5                   10

<210> SEQ ID NO 211
<211> LENGTH: 20
<212> TYPE: PRT
<213> ORGANISM: artificial sequence
<220> FEATURE:
<223> OTHER INFORMATION: Tooth-binding peptide

<400> SEQUENCE: 211

Pro Ser Glu Pro Glu Arg Arg Asp Arg Asn Ile Ala Ala Asn Ala Gly
1               5                   10                  15

Arg Phe Asn Thr
```

20

<210> SEQ ID NO 212
<211> LENGTH: 18
<212> TYPE: PRT
<213> ORGANISM: artificial sequence
<220> FEATURE:
<223> OTHER INFORMATION: Tooth-binding peptide

<400> SEQUENCE: 212

Thr His Asn Met Ser His Phe Pro Pro Ser Gly His Pro Lys Arg Thr
1               5                   10                  15

Ala Thr

<210> SEQ ID NO 213
<211> LENGTH: 14
<212> TYPE: PRT
<213> ORGANISM: artificial sequence
<220> FEATURE:
<223> OTHER INFORMATION: Tooth-binding peptide

<400> SEQUENCE: 213

Thr Thr Cys Pro Thr Met Gly Thr Tyr His Val Cys Trp Leu
1               5                   10

<210> SEQ ID NO 214
<211> LENGTH: 20
<212> TYPE: PRT
<213> ORGANISM: artificial sequence
<220> FEATURE:
<223> OTHER INFORMATION: Tooth-binding peptide

<400> SEQUENCE: 214

Tyr Cys Ala Asp His Thr Pro Asp Pro Ala Asn Pro Asn Lys Ile Cys
1               5                   10                  15

Gly Tyr Ser His
            20

<210> SEQ ID NO 215
<211> LENGTH: 20
<212> TYPE: PRT
<213> ORGANISM: artificial sequence
<220> FEATURE:
<223> OTHER INFORMATION: Tooth-binding peptide

<400> SEQUENCE: 215

Ala Ala Asn Pro His Thr Glu Trp Asp Arg Asp Ala Phe Gln Leu Ala
1               5                   10                  15

Met Pro Pro Lys
            20

<210> SEQ ID NO 216
<211> LENGTH: 20
<212> TYPE: PRT
<213> ORGANISM: artificial sequence
<220> FEATURE:
<223> OTHER INFORMATION: Tooth-binding peptide

<400> SEQUENCE: 216

Asp Leu His Pro Met Asp Pro Ser Asn Lys Arg Pro Asp Asn Pro Ser
1               5                   10                  15

Asp Leu His Thr
            20

<210> SEQ ID NO 217

```
<211> LENGTH: 14
<212> TYPE: PRT
<213> ORGANISM: artificial sequence
<220> FEATURE:
<223> OTHER INFORMATION: Tooth-binding peptide

<400> SEQUENCE: 217

Glu Ser Cys Val Ser Asn Ala Leu Met Asn Gln Cys Ile Tyr
1               5                   10

<210> SEQ ID NO 218
<211> LENGTH: 20
<212> TYPE: PRT
<213> ORGANISM: artificial sequence
<220> FEATURE:
<223> OTHER INFORMATION: Tooth-binding peptide

<400> SEQUENCE: 218

His Asn Lys Ala Asp Ser Trp Asp Pro Asp Leu Pro Pro His Ala Gly
1               5                   10                  15

Met Ser Leu Gly
            20

<210> SEQ ID NO 219
<211> LENGTH: 20
<212> TYPE: PRT
<213> ORGANISM: artificial sequence
<220> FEATURE:
<223> OTHER INFORMATION: Tooth-binding peptide

<400> SEQUENCE: 219

Leu Asn Asp Gln Arg Lys Pro Gly Pro Pro Thr Met Pro Thr His Ser
1               5                   10                  15

Pro Ala Val Gly
            20

<210> SEQ ID NO 220
<211> LENGTH: 14
<212> TYPE: PRT
<213> ORGANISM: artificial sequence
<220> FEATURE:
<223> OTHER INFORMATION: Tooth-binding peptide

<400> SEQUENCE: 220

Asn Thr Cys Ala Thr Ser Pro Asn Ser Tyr Thr Cys Ser Asn
1               5                   10

<210> SEQ ID NO 221
<211> LENGTH: 14
<212> TYPE: PRT
<213> ORGANISM: artificial sequence
<220> FEATURE:
<223> OTHER INFORMATION: Tooth-binding peptide

<400> SEQUENCE: 221

Ser Asp Cys Thr Ala Gly Leu Val Pro Pro Leu Cys Ala Thr
1               5                   10

<210> SEQ ID NO 222
<211> LENGTH: 20
<212> TYPE: PRT
<213> ORGANISM: artificial sequence
<220> FEATURE:
<223> OTHER INFORMATION: Tooth-binding peptide

<400> SEQUENCE: 222

Thr Ile Glu Ser Ser Gln His Ser Arg Thr His Gln Gln Asn Tyr Gly
```

-continued

```
1               5                   10                  15
Ser Thr Lys Thr
            20

<210> SEQ ID NO 223
<211> LENGTH: 20
<212> TYPE: PRT
<213> ORGANISM: artificial sequence
<220> FEATURE:
<223> OTHER INFORMATION: Tooth-binding peptide

<400> SEQUENCE: 223

Val Gly Thr Met Lys Gln His Pro Thr Thr Thr Gln Pro Pro Arg Val
1               5                   10                  15

Ser Ala Thr Asn
            20

<210> SEQ ID NO 224
<211> LENGTH: 20
<212> TYPE: PRT
<213> ORGANISM: artificial sequence
<220> FEATURE:
<223> OTHER INFORMATION: Tooth-binding peptide

<400> SEQUENCE: 224

Tyr Ser Glu Thr Pro Asn Asp Gln Lys Pro Asn Pro His Tyr Lys Val
1               5                   10                  15

Ser Gly Thr Lys
            20
```

RECOMBINANT PEPTIDE PRODUCTION USING A CROSS-LINKABLE SOLUBILITY TAG

CROSS-REFERENCE TO RELATED APPLICATION

This application is a divisional of U.S. patent application Ser. No. 12/172,395 filed Jul. 14, 2008, now pending, which claims the benefit of U.S. Provisional Application No. 60/951,754 filed Jul. 25, 2007.

FIELD OF THE INVENTION

The invention relates to the field of molecular biology, microbiology, and recombinant production of fusion peptides. More specifically, a process to obtain a peptide of interest from a mixture of peptide fragments produced by the cleavage of a fusion peptide is provided.

BACKGROUND OF THE INVENTION

Proteins and peptides are polymers of amino acids that have a wide variety of uses. Peptides are characteristically distinguished from proteins by their smaller size and their lack of tertiary structure needed for complex functionality, such as enzymatic activity. Synthetic peptides that can be designed to exhibit desirable and valuable characteristics have been developed for a variety of purposes.

The efficient production of bioactive proteins and peptides has become a hallmark of the biomedical and industrial biochemical industry. Bioactive peptides and proteins are used as curative agents in a variety of diseases such as diabetes (insulin), viral infections and leukemia (interferon), diseases of the immune system (interleukins), and red blood cell deficiencies (erythropoietin) to name a few. Additionally, large quantities of proteins and peptides are needed for various industrial applications including, for example, the pulp and paper and pulp industries, textiles, food industries, sugar refining, wastewater treatment, production of alcoholic beverages and as catalysts for the generation of new pharmaceuticals.

With the advent of the discovery and implementation of combinatorial peptide screening technologies such as bacterial display (Kemp, D. J.; Proc. Natl. Acad. Sci. USA 78(7): 4520-4524 (1981); yeast display (Chien et al., Proc Natl Acad Sci USA 88(21): 9578-82 (1991)), combinatorial solid phase peptide synthesis (U.S. Pat. Nos. 5,449,754; 5,480,971; 5,585,275 and 5,639,603), phage display technology (U.S. Pat. Nos. 5,223,409; 5,403,484; 5,571,698; and 5,837,500), ribosome display (U.S. Pat. Nos. 5,643,768; 5,658,754; and 7,074,557), and mRNA display technology (PROFUSION™; U.S. Pat. Nos. 6,258,558; 6,518,018; 6,281,344; 6,214,553; 6,261,804; 6,207,446; 6,846,655; 6,312,927; 6,602,685; 6,416,950; 6,429,300; 7,078,197; and 6,436,665) new applications for peptides having specific binding affinities have been developed. In particular, peptides are being looked to as linkers in biomedical fields for the attachment of diagnostic and pharmaceutical agents to surfaces (see Grinstaff et al, U.S. Patent Application Publication No. 2003/0185870 and Linter in U.S. Pat. No. 6,620,419), as well as in the personal care industry for the attachment of benefit agents to body surfaces such as hair and skin (see commonly owned U.S. patent application Ser. No. 10/935,642, and Janssen et al. U.S. Patent Application Publication No. 2003/0152976), and in the printing industry for the attachment of pigments to print media (see commonly owned U.S. patent application Ser. No. 10/935,254).

In some cases commercially useful proteins and peptides may be synthetically generated or isolated from natural sources. However, these methods are often expensive, time consuming and characterized by limited production capacity. The preferred method of protein and peptide production is through the fermentation of recombinantly constructed organisms, engineered to over-express the protein or peptide of interest. Although preferable to synthesis or isolation, recombinant expression of peptides has a number of obstacles to be overcome in order to be a cost-effective means of production. For example, peptides (and in particular short peptides) produced in a cellular environment are often soluble and susceptible to degradation from the action of native cellular proteases. Purification can be difficult, resulting in poor yields depending on the nature of the protein or peptide of interest.

One means to mitigate the above difficulties is the use the genetic chimera for protein and peptide expression. A chimeric protein or "fusion protein" is a polypeptide comprising at least one portion of the desired protein product fused to at least one portion comprising a peptide tag. The peptide tag may be used to assist protein folding, assist post expression purification, protect the protein from the action of degradative enzymes, and/or assist the protein in passing through the cell membrane.

In many cases it is useful to express a protein or peptide in insoluble form, particularly when the peptide of interest is rather short, substantially soluble, and subject to proteolytic degradation within the host cell. Production of the peptide in insoluble form both facilitates simple recovery and protects the peptide from the undesirable proteolytic degradation. One means to produce the peptide in insoluble form is to recombinantly produce the peptide of interest in the form of an insoluble fusion protein by including within the fusion construct at least one solubility tag (i.e., an inclusion body tag) that promotes inclusion body formation. Typically, the fusion protein is also designed to include at least one cleavable peptide linker so that the peptide of interest can be subsequently recovered from the fusion protein. The fusion protein may be designed to include a plurality of inclusion body tags, cleavable peptide linkers, and regions encoding the peptide of interest.

Fusion proteins comprising a peptide tag that facilitate the expression of insoluble proteins are well known in the art. Typically, the tag portion of the chimeric or fusion protein is large, increasing the likelihood that the fusion protein will be insoluble. Example of large peptide tags typically used include, but are not limited to chloramphenicol acetyltransferase (Dykes et al., Eur. J. Biochem., 174:411 (1988), β-galactosidase (Schellenberger et al., Int. J. Peptide Protein Res., 41:326 (1993); Shen et al., Proc. Nat. Acad. Sci. USA 281: 4627 (1984); and Kempe et al., Gene, 39:239 (1985)), glutathione-S-transferase (Ray et al., Bio/Technology, 11:64 (1993) and Hancock et al. (WO94/04688)), the N-terminus of L-ribulokinase (U.S. Pat. No. 5,206,154 and Lai et al., Antimicrob. Agents & Chemo., 37:1614 (1993), bacteriophage T4 gp55 protein (Gramm et al., Bio/Technology, 12:1017 (1994), bacterial ketosteroid isomerase protein (Kuliopulos et al., J. Am. Chem. Soc. 116:4599 (1994) and co-owned U.S. Patent Publication No. 2006/0222609), ubiquitin (Pilon et al., Biotechnol. Prog., 13:374-79 (1997), bovine prochymosin (Naught et al., Biotechnol. Bioengineer. 57:55-61 (1998), and bactericidal/permeability-increasing protein ("BPI"; Better, M. D. and Gavit, P D., U.S. Pat. No. 6,242,219). The art is replete with specific examples of this technology, see for example U.S. Pat. No. 6,613,548, describing fusion protein of proteinaceous tag and a soluble protein and subsequent purification from cell lysate; U.S. Pat. No. 6,037,145, teaching a tag that protects the expressed chimeric protein from a specific protease; U.S. Pat. No. 5,648,244, teaching the synthesis of a fusion protein having a tag and a cleavable linker for facile purification of the desired protein; and U.S. Pat. Nos. 5,215,896; 5,302,526; 5,330,902; and U.S. Patent Publication No. 2005/221444, describing fusion tags containing amino acid compositions specifically designed to increase insolubility of the chimeric protein or peptide.

Although the above methods are useful for the expression of fusion proteins, they often incorporate large inclusion body tags that decrease the potential yield of desired peptide of interest. This is particularly problematic in situations where the desired protein or peptide is small. In such situations it is advantageous to use a small inclusion body tag to maximize yield.

Shorter inclusion tags have recently been developed from the *Zea mays* zein protein (co-pending U.S. patent application Ser. No. 11/641,936), the *Daucus carota* cystatin (co-pending U.S. patent application Ser. No. 11/641,273), an amyloid-like hypothetical protein from *Caenorhabditis elegans* (co-owned U.S. patent application Ser. No. 11/516,362), and tags comprising a n-sheet tape architecture (Aggeli et al., *J. Amer. Chem. Soc.*, 125:9619-9628 (2003); Aggeli et al., *PNAS*, 98(21):11857-11862 (2001); Aggeli et al., *Nature*, 386:259-262 (1997); Aggeli et al., *J. Mater Chem*, 7(7):1135-1145 (1997); and co-pending U.S. patent application Ser. No. 11/782,836. The use of short inclusion body tags increases the yield of the target peptide produced within the recombinant host cell.

Recovering the recombinantly produced peptide of interest from the fusion protein typically involves at least on cleavage step used to separate the peptide of interest from the inclusion body tag. Once cleaved, the peptide of interest is recovered from the mixture of peptide fragments. However, recovery of the peptide of interest is often difficult, especially when the inclusion body tag and the peptide of interest are similar in size and/or exhibit similar solubility characteristics.

The problem to be solved is to provide a cost effective process to separate the inclusion body tag from the peptide of interest.

SUMMARY OF THE INVENTION

The stated problem has been solved by providing a process to obtain a peptide of interest from a mixture of peptide fragments obtained after cleaving the fusion peptide. Specifically, an effective number of cross-linkable cysteine residues are engineered into only one of the two components of the fusion peptide (i.e. the portion comprising the inclusion body tag or the portion comprising the peptide of interest). Cleavage of the fusion peptide forms a mixture of peptide fragments that is subsequently subjected to oxidative conditions whereby intermolecular and intramolecular disulfide bonds are formed between the cysteine residues engineered into only one of the two portions of the fusion peptide. The selectively cross-linked peptide fragments are of higher molecular weight and are insoluble within the process matrix. Suitable process conditions are used to ensure that the portion of the fusion peptide designed to be devoid of cysteine residues remains substantially soluble (after cleavage). The insoluble component is easily separated from the soluble component using any number of well known separation techniques such as centrifugation and/or filtration.

In one embodiment, the inclusion body tag comprises an effective number of cross-linkable cysteine residues while no cysteine residues are present in the peptide of interest. As such, a process to obtain a peptide of interest from a fusion protein is provided comprising:

a) providing a population of fusion peptides comprising the general structure:

IBT-CS-POI or

POI-CS-IBT wherein;
i) IBT is an inclusion body tag comprising an effective number of cysteine residues;
ii) CS is a cleavage site; and
iii) POI is a peptide of interest that does not include a cysteine residue;

b) cleaving the population of fusion peptides at said cleavage site whereby the inclusion body tag is no longer linked to the peptide of interest and whereby a mixture of peptide molecules is produced comprising a plurality of inclusion body tags and a plurality of peptides of interest;

c) subjecting the mixture of peptide molecules of step (b) to oxidizing conditions whereby the inclusion body tags are cross-linked; and d) recovering the peptide of interest.

In another embodiment, a method to obtain a peptide of interest is also provided comprising:

a) providing a recombinant host cell comprising a nucleic acid molecule encoding a fusion peptide comprising the general structure:

IBT-CS-POI or

POI-CS-IBT wherein;
i) IBT is an inclusion body tag comprising an effective number of cysteine residues;
ii) CS is a cleavage site; and
iii) POI is a peptide of interest that does not include a cysteine residue;

b) growing the host cell of step (a) under conditions whereby a population of fusion peptides is produced;

c) cleaving the population of fusion peptides at said cleavage site whereby the inclusion body tag is no longer linked to the peptide of interest and whereby a mixture of peptide molecules is produced comprising a plurality of inclusion body tags and a plurality of peptides of interest;

d) subjecting the mixture of peptide molecules of step (c) to oxidizing conditions whereby the inclusion body tags are cross-linked; and e) recovering the peptide of interest.

The peptide of interest is isolated and/or recovered from the mixture of peptide molecules based on the difference in molecular weight and/or solubility of the peptide of interest relative to the cross-linked inclusion body tags. Recovery of the peptide of interest can use any number of well known separation techniques including, but not limited to centrifugation and/or filtration (including microfiltration).

In an alternative embodiment, the peptide of interest comprises an effective number of cross-linkable cysteine residues while the inclusion body tag is devoid of cysteine residues. As such, a process to obtain a peptide of interest is provided comprising:

a) providing a population of fusion peptides comprising the general structure:

IBT-CS-POI or

POI-CS-IBT wherein;
i) IBT is an inclusion body tag that does not include a cysteine residue;
ii) CS is a cleavage site; and
iii) POI is a peptide of interest comprising an effective number of cysteine residues;
b) cleaving the population of fusion peptides at said cleavage site whereby the inclusion body tag is no longer linked to the peptide of interest and whereby a mixture of peptide molecules is produced comprising a plurality of inclusion body tags and a plurality of peptides of interest;
c) subjecting the mixture of peptide molecules of step (b) to oxidizing conditions whereby the peptides of interest are cross-linked; and
d) recovering the peptide of interest.

In yet another embodiment, a method to obtain a peptide of interest is also provided comprising:

a) providing a recombinant host cell comprising a nucleic acid molecule encoding a fusion peptide comprising the general structure:

IBT-CS-POI or

POI-CS-IBT wherein;
i) IBT is an inclusion body tag that does not include a cysteine residue;
ii) CS is a cleavage site; and
iii) POI is a peptide of interest comprising an effective number of cysteine residues;
b) growing the host cell of step (a) under conditions whereby a population of fusion peptides is produced;
c) cleaving the population fusion peptides at said cleavage site whereby a mixture of peptide molecules is produce comprising a plurality of inclusion body tags and a plurality of peptides of interest;
d) subjecting the mixture of peptide molecules of step (c) to oxidizing conditions whereby the peptide of interest is cross-linked; and
e) recovering the peptide of interest.

BRIEF DESCRIPTION OF THE BIOLOGICAL SEQUENCES

Figure 1:
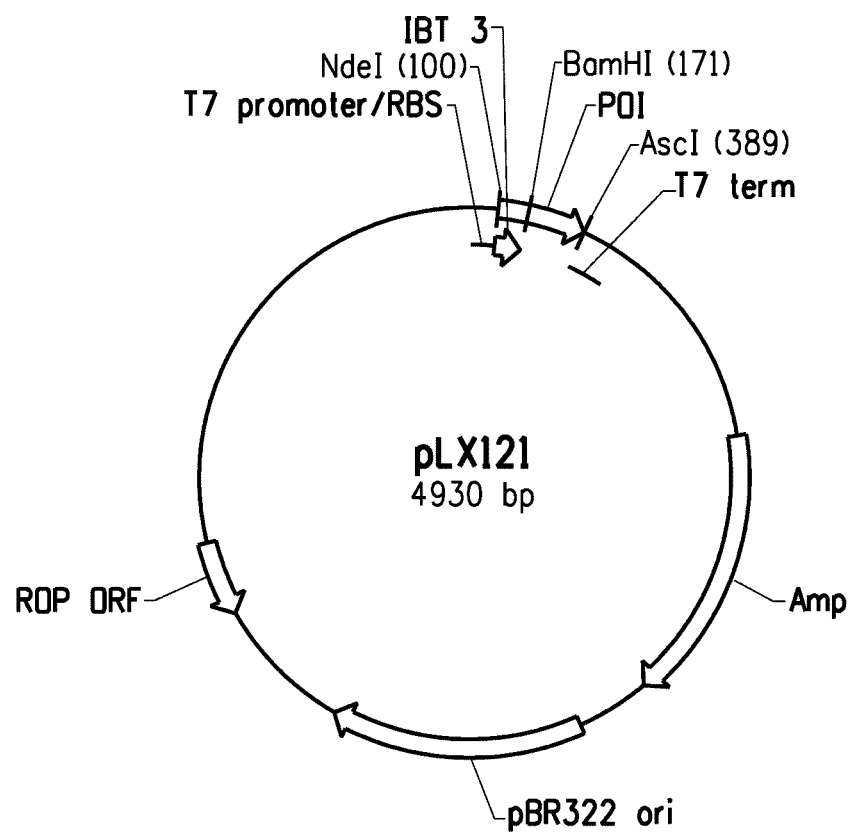
FIG. 1 is a diagram of expression plasmid pLX121.

The following sequences comply with 37 C.F.R. 1.821-1.825 ("Requirements for Patent Applications Containing Nucleotide Sequences and/or Amino Acid Sequence Disclosures—the Sequence Rules") and are consistent with World Intellectual Property Organization (WIPO) Standard ST.25 (1998) and the sequence listing requirements of the EPC and PCT (Rules 5.2 and 49.5(a-bis), and Section 208 and Annex C of the Administrative Instructions). The symbols and format used for nucleotide and amino acid sequence data comply with the rules set forth in 37 C.F.R. §1.822.

SEQ ID NO: 1 is the nucleic acid sequence of plasmid pLX121.
SEQ ID NO: 2 is the nucleic acid sequence of plasmid pKSIC4-HC77623.
SEQ ID NO: 3 is the nucleic acid sequence of plasmid pLR042.
SEQ ID NO: 4 is the nucleic acid sequence of plasmid pLR186.
SEQ ID NO: 5 is the nucleic acid sequence encoding the KSI(4C) inclusion body tag.
SEQ ID NO: 6 is the amino acid sequence of inclusion body tag KSI(4C).
SEQ ID NO: 7 is the nucleic acid sequence encoding the KSI.HC77607 fusion peptide.
SEQ ID NO: 8 is the amino acid sequence of the KSI.HC77607 fusion peptide.
SEQ ID NO: 9 is the amino acid sequence of hair binding domain KF11.
SEQ ID NO: 10 is the amino acid sequence of hair binding domain D21.
SEQ ID NO: 11 is the nucleic acid sequence encoding the peptide of interest HC77607 (multi-block hair-binding peptide).
SEQ ID NO: 12 is the amino acid sequence of HC77607 (multi-block hair-binding peptide).
SEQ ID NO: 13 is the nucleic acid sequence encoding the KSI(C4).HC77643 fusion peptide.
SEQ ID NO: 14 is the amino acid sequence of fusion peptide KSI(C4).HC77643.
SEQ ID NO: 15 is the amino acid sequence of hair binding peptide AO9.
SEQ ID NO: 16 is the nucleic acid sequence encoding the peptide of interest HC77643 (multi-block hair binding peptide).
SEQ ID NO: 17 is the amino acid sequence of the multi-block hair-binding peptide HC77643.
SEQ ID NO: 18 is the amino acid sequence of inclusion body tag IBT139.
SEQ ID NO: 19 is the nucleic acid sequence encoding fusion peptide IBT139.HC776124.
SEQ ID NO: 20 is the amino acid sequence of fusion peptide IBT139.HC776124.
SEQ ID NIO: 21 is the nucleic acid sequence encoding the peptide of interest HC776124 (multi-block hair-binding peptide).
SEQ ID NO: 22 is the amino acid sequence of multi-block hair-binding peptide HC776124.
SEQ ID NO: 23 is the nucleic acid sequence encoding inclusion body tag IBT186.
SEQ ID NO: 24 is the amino acid sequence of inclusion body tag IBT186.
SEQ ID NO: 25 is the nucleic acid sequence encoding the fusion peptide IBT186.HC776124.
SEQ ID NO: 26 is the amino acid sequence of fusion peptide IBT186.HC776124.
SEQ ID NO: 27 is the amino acid sequence of inclusion body tag IBT139.CCPGCC.
SEQ ID NO: 28 is the nucleic acid sequence encoding the fusion peptide IBT139.CCPGCC.HC776124.
SEQ ID NO: 29 is the amino acid sequence of fusion peptide IBT139.CCPGCC.HC776124.

SEQ ID NO: 30 is the amino acid sequence of a tetracysteine motif useful as a cross-linkable tag.

SEQ ID NO: 31 is the nucleic acid sequence encoding the CCPGCC cross-linkable cysteine motif.

SEQ ID NO: 32 is the amino acid sequence of the CCPGCC cysteine motif.

SEQ ID NOs: 33-34 are the nucleic acid sequences of primers.

SEQ ID NOs: 35-37 and 43-58 are the amino acid sequences of hair binding peptides.

SEQ ID NOs: 38-42 are the amino acid sequences of peptides that bind to both hair and skin.

SEQ ID NOs: 59-71 are the amino acid sequences of skin binding peptides.

SEQ ID NOs: 72-73 are the amino acid sequences of nail-binding peptides.

SEQ ID NOs: 74-102 are the amino acid sequences of antimicrobial peptides.

SEQ ID NOs: 103-128 are the amino acid sequences of pigment binding peptides. Specifically, SEQ ID NOs: 103-106 bind to carbon black, SEQ ID NOs: 107-115 bind to CROMOPHTAL® yellow (Ciba Specialty Chemicals, Basel, Switzerland), SEQ ID NOs: 116-118 bind to SUNFAST® magenta (Sun Chemical Corp., Parsippany, N.J.), and SEQ ID NOs: 119-128 bind to SUNFAST® blue.

SEQ ID NOs: 129-134 are cellulose-binding peptides.

SEQ ID NOs: 135-162 are the amino acid sequences of polymer binding peptides. Specifically, SEQ ID NO: 135 binds to poly(ethylene terephthalate), SEQ ID NOs: 136-147 bind to poly(methyl methacrylate), SEQ ID NOs: 148-153 bind to Nylon, and SEQ ID NOs: 154-162 bind to poly(tetrafluoroethylene).

SEQ ID NOs: 163-178 are the amino acid sequences of clay binding peptides.

SEQ ID NO: 179 is the amino acid sequence of the Caspase-3 cleavage sequence.

SEQ ID NO: 180 is the nucleic acid sequence of plasmid pLR435.

SEQ ID NO: 181 is the nucleic acid sequence encoding inclusion body tag IBT139(5C).

SEQ ID NO: 182 is the amino acid sequence of inclusion body tag IBT139(5C).

SEQ ID NO: 183 is the nucleic acid sequence encoding fusion peptide IBT139(5C).HC776124.

SEQ ID NO: 184 is the amino acid sequence of fusion peptide IBT139(5C).HC776124.

SEQ ID NOs: 185-224 are the amino acid sequences of teeth-binding peptides (U.S. patent application Ser. No. 11/877,692).

DETAILED DESCRIPTION OF THE INVENTION

A process to obtain a peptide of interest from a fusion peptide is provided. The peptide of interest is produced in the form of a fusion protein engineered to have at least two functional portions separated by at least one cleavable peptide linker. One functional portion is a solubility tag ("inclusion body tag") designed to promote production of the fusion protein in an insoluble form (i.e. in the form of inclusion bodies). Another portion of the fusion protein comprises the peptide targeted for production (the "peptide of interest"). In a preferred embodiment, the fusion peptide is recombinantly produced in a microbial host cell.

One of the two functional portions of the fusion protein is designed to have an effective number of cross-linkable cysteine residues while the other functional portion is designed to be devoid of cysteine residues. The fusion protein is subjected to conditions whereby the peptide linker is cleaved, forming a mixture of peptide fragments comprising the inclusion body tags and the peptides of interest. The mixture of peptide fragments is then subjected to oxidizing conditions whereby the portion of the fusion peptide designed having a plurality of cross-linkable cysteine residues is cross-linked by the formation of intermolecular disulfide bonds. The cross-linked peptide molecules (higher in molecular weight and less soluble/insoluble) are separated from the non-cross-linked soluble peptide molecules (i.e. the portion of the fusion peptide designed to be devoid of cross-linkable cysteine residues). The cross-linked portion may be separated from the non-cross-linked portion on the basis of molecular weight and/or solubility. Methods to separate the two materials based on differences in molecular weight and/or solubility are well known in the art and may include, but are not limited to techniques such as centrifugation and/or filtration.

The following definitions are used herein and should be referred to for interpretation of the claims and the specification.

As used herein, the term "comprising" means the presence of the stated features, integers, steps, or components as referred to in the claims, but that it does not preclude the presence or addition of one or more other features, integers, steps, components or groups thereof.

As used herein, the term "about" refers to modifying the quantity of an ingredient or reactant of the invention or employed refers to variation in the numerical quantity that can occur, for example, through typical measuring and liquid handling procedures used for making concentrates or use solutions in the real world; through inadvertent error in these procedures; through differences in the manufacture, source, or purity of the ingredients employed to make the compositions or carry out the methods; and the like. The term "about" also encompasses amounts that differ due to different equilibrium conditions for a composition resulting from a particular initial mixture. Whether or not modified by the term "about", the claims include equivalents to the quantities.

The term "invention" or "present invention" as used herein is a non-limiting term and is not intended to refer to any single embodiment of the particular invention but encompasses all possible embodiments as described in the specification and the claims.

As used herein, the terms "fusion protein", "fusion peptide", "chimeric protein", and "chimeric peptide" will be used interchangeably and will refer to a polymer of amino acids (peptide, oligopeptide, polypeptide, or protein) comprising at least two portions, each portion comprising a distinct function. One portion of the fusion peptide comprises at least one inclusion body tag (IBT). The second portion comprises at least one peptide of interest (POI). The fusion protein additionally includes at least one cleavable peptide linker (CL) that facilitates cleavage (chemical and/or enzymatic) and separation of the inclusion body tag(s) and the peptide(s) of interest. The fusion protein is designed such that either the inclusion body tag or the peptide of interest comprises a plurality (e.g., 3 or more) cross-linkable cysteine residues (cross-linkable cysteine residues). Once the fusion protein is cleaved (using acid cleavage and/or enzymatic cleavage), the portion comprising the inclusion body tag is separated from the portion comprising the peptide of interest by selectively cross-linking the portion comprising the cross-linkable cysteine residues. Oxidative cross-linking can be carried out using any number of techniques (i.e. bubbling oxygen through the mixture and/or by the use of chemical oxidants). The cross-linked portion is separated from portion devoid of cysteine residues using any number of simple separation techniques including, but not limited to centrifugation, filtration, and combinations thereof.

As used herein, the term "effective number of cysteine residues" is used to describe the number of cysteine residues required to obtain the desired effect (i.e. the ability to use oxidative cross-linking to selectively cross-link at least one portion of the cleaved fusion peptide). It is well within the skill of one in the art to vary the number and/or location of the cysteine residues within the fusion peptide to practice the present process. In one embodiment, the effective number of cysteine residues is at least 3, preferably at least 4. In another embodiment, the effective number of cysteine residues is 3 to about 20, preferably 3 to about 10, more preferably 3 to about 6, more preferably 3 to about 5, and most preferably 4 to 5 cross-linkable cysteine residues.

As used herein, the terms "inclusion body tag" and "solubility tag" are used interchangeably and will be abbreviated "IBT" and will refer a polypeptide that facilitates/promotes formation of inclusion bodies when fused to a peptide of interest. The peptide of interest is typically soluble within the host cell and/or host cell lysate when not fused to an inclusion body tag. Fusion of the peptide of interest to the inclusion body tag produces an insoluble fusion protein that typically agglomerates into intracellular bodies (inclusion bodies) within the host cell. In one embodiment, the fusion protein comprises at least one portion comprising an inclusion body tag and at least one portion comprising the polypeptide of interest. In one embodiment, the protein/peptide of interest is separated from the inclusion body tag using at least one cleavable peptide linker elements ("cleavage sites", abbreviated herein as "CS").

As used herein, "cleavable linker elements", "peptide linkers", and "cleavable peptide linkers" will be used interchangeably and refer to cleavable peptide segments separating the inclusion body tag(s) and the peptide(s) of interest. The cleavable peptide linker provides a site within the fusion peptide for selective cleavage of the fusion peptide (i.e. the "cleavage site" or "cleavage sequence"). In one embodiment, the fusion peptide is designed to have at least one cleavable peptide linker comprising a cleavage site separating the IBT from the POI. In a preferred embodiment, the arrangement of the cleavage site within the fusion protein comprises an arrangement of IBT-CS-POI wherein the cleavage site is at least one acid labile DP moiety. In one embodiment, the fusion peptide comprises a plurality of POIs and/or a plurality of IBTs separated by one or more cleavage sites so long as a first functional portion (e.g. IBTs) can be selectively separated from a second functional portion (e.g. POIs) using the present process of oxidatively cross-linking an effective number of cysteine residues incorporated into only one of the two functional portions of the fusion peptide.

After the inclusion bodies are separated and/or partially-purified or purified from the cell lysate, the cleavable linker elements can be cleaved chemically and/or enzymatically to separate the inclusion body tag from the peptide of interest. The cleavable peptide linker may be from 1 to about 50 amino acids, preferably from 1 to about 20 amino acids in length. An example of a cleavable peptide linker is provided by SEQ ID NO: 179 (Caspase-3 cleavage sequence). Any cleavable peptide linker can be used so long as the amino acid composition of the cleavage site does not adversely impact the present process. The cleavable peptide linkers may be incorporated into the fusion protein using any number of techniques well known in the art.

As used herein, an "inclusion body" is an intracellular amorphous deposit comprising aggregated protein found in the cytoplasm of a cell. Peptides of interest that are soluble with the host cell and/or cell lysates can be fused to one or more inclusion body tags to facilitate formation of an insoluble fusion protein. In an alternative embodiment, the peptide of interest may be partially insoluble in the host cell, but produced at relatively lows levels where significant inclusion body formation does not occur. As such, the formation of inclusion bodies will increase protein yield and/or protect the peptide from proteolytic degradation. Formation of the inclusion body facilitates purification of the fusion peptide from the cell lysate using techniques well known in the art such as centrifugation and filtration. The fusion peptide ("chimeric peptide") is designed to include one or more cleavable peptide linkers (encoding a cleavage site) separating the portion(s) comprising the peptide(s) of interest from the portion(s) comprising the inclusion body tag(s). The cleavable peptide linker is designed so that the portion comprising the inclusion body tag and the portion comprising the peptide of interest can be separated by cleaving fusion peptide at the desired cleavage site (CS). The cleavage site can be cleaved chemically (e.g., acid hydrolysis) or enzymatically (i.e., use of a protease/peptidase that preferentially recognizes an amino acid cleavage site and/or sequence within the cleavable peptide linker). Once the fusion peptide is cleaved, the inclusion body tag(s) can be separated from the peptide of interest using the present process of selective cross-linking.

As used herein, the terms "cross-linking", "oxidative cross-linking", and "cysteine cross-linking" refer the present process of cross-linking the thiol groups of cysteine residues (i.e. forming intermolecular and intramolecular disulfide bonds) under oxidizing conditions. By definition, the formation of intermolecular disulfide bonds occurs between two or more molecules (i.e. a "plurality") comprising an effective number cross-linkable cysteine residues. As used herein, a "plurality" of molecules will alternatively be referred to herein as a "population" of molecules. In order to promote intermolecular cross-linking, an effective number (i.e. a plurality of at least 3) cross-linkable cysteine residues are incorporated into either the portion comprising the inclusion body tag or the portion comprising the peptide of interest. In one embodiment, at least 3 cysteine residues are incorporated into the portion of the fusion protein targeted for cross-linking, preferably 3 to about 20 cysteine residues, more preferably 3 to about 10 cysteine residues, yet even more preferably 3 to about 6 cysteine residues, more preferably 3 to about 5 cysteine residues, and most preferably about 4 or 5 cysteine residues are used. In a preferred embodiment, the cross-linkable cysteine residues are engineered into the inclusion body tag so that the peptide of interest (which is this case would not contain a cross-linkable cysteine residue) is isolated as a soluble peptide from the insoluble, cross-linked, inclusion body tags. In another embodiment, the cross-linkable cysteine residues are incorporated into the peptide of interest while the portion comprising the inclusion body tag does not include any cross-linkable cysteine residues. When the peptide of interest is separated from the inclusion body tag as a cross-linked peptide agglomerate (typically insoluble), the cross-linked peptide of interest may subsequently be subjected to reducing conditions prior to preparing commercial formulations using the peptide of interest.

As used herein, the term "oxidizing conditions" refers to reaction conditions which favor and promote the formation of disulfide bonds between cysteine residues. Disulfide bond formation can be induced by any number of means well known in the art including, but not limited to contacting the cross-linkable cysteine residues with a gas comprised of oxygen (i.e. diatomic $[O_2]$ and/or triatomic oxygen $[O_3]$) and/or the addition of chemical oxidants. The use of gas comprising molecular oxygen is preferred. In a further embodiment, a gas comprising diatomic and/or triatomic oxygen is bubbled and/or sparged through the aqueous reaction solution for a period of time to achieve effective oxidative cross-linking. The oxidative cross-linking step may optionally include the act of mixing and/or stirring of the aqueous reaction mixture for optimal results. Examples of chemical oxidants are well-known in the art and may include, but are not limited to peroxide compounds, hypochlorite, halogens, and permanganate salts; to name a few.

As used herein, the term "reducing conditions" refers to reaction conditions which favor and promote the reduction of disulfide bonds between cysteine residues (i.e. breaks disulfide bond used for cross-linking). Disulfide bonds can be reduced by any number of means well known such as the use of nitrogen purge and/or a chemical reducing agent such as $Na_2SO_3$, DTT (dithiothreitol), TCEP (tris(2-carboxyethyl) phosphine), 2-mercaptoethanol, 2-mercaptoethylamine, and mixtures thereof. Generally reducing agents include those that contain thiol groups, those that are phosphines and their derivatives as well as sulfites and thiosulfites.

As used herein, the term "solubility" refers to the amount of a substance that can be dissolved in a unit volume of a liquid under specified conditions. As used herein, the term is used to describe the ability of a peptide (inclusion body tag, peptide of interest, or fusion peptide) to be suspended in a volume of solvent, such as a biological buffer. In one embodiment, the peptides targeted for production ("peptides of interest") are normally soluble in the cell and/or cell lysate under normal physiological conditions. Fusion of one or more inclusion body tags (IBTs) to the target peptide results in the formation of a fusion peptide that is insoluble under normal physiological conditions, resulting in the formation of inclusion bodies. In the present process, the insoluble fusion peptides are recovered from the cell and cleaved at the cleavage site into a mixture of peptides fragments comprising a plurality of inclusion body tags and a plurality of peptide of interests. In one embodiment, the isolated fusion peptide is solubilized prior to the introducing conditions that promote cleavage of the cleavable peptide linker. The mixture of peptide obtained after cleavage is then subjected to oxidizing conditions whereby the peptide fragments comprising an effective number of cross-linkable cysteine residues are selectively cross-linked into higher molecular weight molecules that are typically insoluble under the chosen conditions while the non-cross-linked fragments remain substantially soluble.

As used herein, the term "pigment" refers to an insoluble, organic or inorganic colorant.

As used herein, the term "hair" as used herein refers to mammalian or human hair, eyebrows, and eyelashes.

As used herein, "HBP" means hair-binding peptide. As used herein, the term "hair-binding peptide" refers to peptide sequences that bind with high affinity to hair. Examples of hair binding peptides have been reported (U.S. patent application Ser. No. 11/074,473 to Huang et al.; WO 0179479; U.S. Patent Application Publication No. 2002/0098524 to Murray et al.; Janssen et al., U.S. Patent Application Publication No. 2003/0152976 to Janssen et al.; WO 2004048399; U.S. application Ser. No. 11/512,910, and U.S. patent application Ser. No. 11/696,380). Hair-binding peptides may include one or more hair-binding domains. As used herein, hair-binding peptides comprising of a plurality of hair-binding domains are referred to herein as "multi-block" or "multi-copy" hair-binding peptides. Examples of hair-binding peptides are provided as SEQ ID NOs: 9-10, 12, 15, 17, 22, and 35-58 (Table 1).

As used herein, the term "skin" as used herein refers to mammalian or human skin, or substitutes for human skin, such as pig skin, VITRO-SKIN® (Innovative Measurement Solutions Inc., Milford, Conn.) and EPIDERM™ (MatTek Corporation, Ashland, Mass.). Skin, as used herein, will refer to a body surface generally comprising a layer of epithelial cells and may additionally comprise a layer of endothelial cells.

As used herein, "SBP" means skin-binding peptide. As used herein, the term "skin-binding peptide" refers to peptide sequences that bind with high affinity to skin. Examples of skin binding peptides have also been reported (U.S. patent application Ser. No. 11/069,858 to Buseman-Williams; Rothe et. al., WO 2004/000257; and U.S. patent application Ser. No. 11/696,380). Examples of skin-binding peptides are provided as SEQ ID NOs: 38-42 and 59-71 (Table 1).

As used herein, the term "nails" as used herein refers to mammalian or human fingernails and toenails.

As used herein, "NBP" means nail-binding peptide. As used herein, the term "nail-binding peptide" refers to peptide sequences that bind with high affinity to the surface of fingernail or toenail tissue. Examples of nail binding peptides have been reported (U.S. patent application Ser. No. 11/696,380). Examples of nail-binding peptides are provided as SEQ ID NOs: 72-73 (Table 1).

As used herein, "TBP" means tooth-binding peptide. A tooth-binding peptide is a peptide that binds with high affinity to a mammalian or human tooth surface.

The term "tooth surface" will refer to a surface comprised of tooth enamel (typically exposed after professional cleaning or polishing) or tooth pellicle (an acquired surface comprising salivary glycoproteins). Hydroxyapatite can be coated with salivary glycoproteins to mimic a natural tooth pellicle surface (tooth enamel is predominantly comprised of hydroxyapatite).

As used herein, the terms "pellicle" and "tooth pellicle" will refer to the thin film (typically ranging from about 1 μm to about 200 μm thick) derived from salivary glycoproteins which forms over the surface of the tooth crown. Daily tooth brushing tends to only remove a portion of the pellicle surface while abrasive tooth cleaning and/or polishing (typically by a dental professional) will exposure more of the tooth enamel surface.

As used herein, the terms "enamel" and "tooth enamel" will refer to the highly mineralized tissue which forms the outer layer of the tooth. The enamel layer is composed primarily of crystalline calcium phosphate (i.e. hydroxyapatite; $Ca_5(PO_4)_3OH$) along with water and some organic material. In one embodiment, the tooth surface is selected from the group consisting of tooth enamel and tooth pellicle.

As used herein, the term "tooth-binding peptide" will refer to a peptide that binds to tooth enamel or tooth pellicle. In one embodiment, the tooth-binding peptides are from about 7 amino acids to about 50 amino acids in length, more preferably, from about 7 amino acids to about 25 amino acids in length, most preferably from about 7 to about 20 amino acids in length. In a preferred embodiment, the tooth-binding peptides are combinatorially-generated peptides.

Examples of tooth-binding peptides having been disclosed in co-pending and co-owned U.S. patent application Ser. No. 11/877,692 and are provided in Table 1. In a preferred embodiment, the tooth-binding peptide is selected from the group consisting of SEQ ID NOs: 185-224.

As used herein, "PBP" means polymer-binding peptide. As used herein, the term "polymer-binding peptide" refers to peptide sequences that bind with high affinity to a specific polymer (U.S. patent application Ser. No. 11/516,362). Examples include peptides that bind to poly(ethylene terephthalate) (SEQ ID NO: 135), poly(methyl methacrylate) (SEQ ID NOs:136-147), Nylon (SEQ ID NOs: 148-153), and poly (tetrafluoroethylene) (SEQ ID NOs: 154-162).

As used herein, an "antimicrobial peptide" is a peptide having the ability to kill microbial cell populations (U.S. patent application Ser. No. 11/516,362). Examples of antimicrobial peptides are provided as SEQ ID NOs: 74-102.

As used herein, "cellulose-binding peptide" refers to a peptide that binds with high affinity to cellulose. Examples of cellulose-binding peptides are provided as SEQ ID NOs: 129-134.

As used herein, "clay-binding peptide" refers to a peptide that binds with high affinity to clay (U.S. patent application Ser. No. 11/696,380). Examples of clay-binding peptides are provided as SEQ ID NOs: 163-178.

As used herein, the "benefit agent" refers to a molecule that imparts a desired functionality to a peptide complex involving the peptide of interest for a defined application. The benefit agent may be the peptide of interest itself or may be one or more molecules bound to (covalently or non-covalently), or associated with, the peptide of interest wherein the binding affinity of the polypeptide is used to selectively target the benefit agent to the targeted material. In another embodiment, the targeted polypeptide comprises at least one region having an affinity for at least one target material (e.g., polymers, biological molecules, hair, skin, nail, teeth, other biological surfaces, other peptides, etc.) and at least one region having an affinity for the benefit agent (e.g., pharmaceutical agents, particulate benefit agents, clays, calcium carbonate, pigments, conditioners, dyes, fragrances, and polymeric coatings applied to particulate benefit agents). In another embodiment, the peptide of interest comprises a plurality of regions having an affinity for the target material and a plurality of regions having an affinity for the benefit agent. In yet another embodiment, the peptide of interest comprises at least one region having an affinity for a targeted material and a plurality of regions having an affinity for a variety of benefit agents wherein the benefit agents may be the same of different. Examples of benefits agents may include, but are not limited to conditioners for personal care products, particulate benefit agents (e.g. clays), pigments, dyes, fragrances, pharmaceutical agents (e.g., targeted delivery of disease treatment agents), diagnostic/labeling agents, ultraviolet light blocking agents (i.e., active agents in sunscreen protectants), and antimicrobial agents (e.g., antimicrobial peptides), to name a few.

As used herein, the term "isolated nucleic acid molecule" is a polymer of RNA or DNA that is single- or double-stranded, optionally containing synthetic, non-natural or altered nucleotide bases. An isolated nucleic acid molecule in the form of a polymer of DNA may be comprised of one or more segments of cDNA, genomic DNA or synthetic DNA.

As used herein, the term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). In a further embodiment, the definition of "operably linked" may also be extended to describe the products of chimeric genes, such as fusion proteins. As such, "operably linked" or "linked" will also refer to the linking of an inclusion body tag to a peptide of interest to be produced and recovered. The inclusion body tag is "operably linked" to the peptide of interest if upon expression the fusion protein is insoluble and accumulates in inclusion bodies in the expressing host cell. In a preferred embodiment, the fusion peptide will include at least one cleavable peptide linker useful in separating the inclusion body tag from the peptide of interest. In a further preferred embodiment, the cleavable linker is an acid cleavable aspartic acid-proline dipeptide (D-P) moiety. The cleavable peptide linkers may be incorporated into the fusion proteins using any number of techniques well known in the art.

As used herein, the terms "polypeptide" and "peptide" will be used interchangeably to refer to a polymer of two or more amino acids joined together by a peptide bond, wherein the peptide is of unspecified length, thus, peptides, oligopeptides, polypeptides, and proteins are included within the present definition. In one aspect, this term also includes post expression modifications of the polypeptide, for example, glycosylations, acetylations, phosphorylations and the like. Included within the definition are, for example, peptides containing one or more analogues of an amino acid or labeled amino acids and peptidomimetics.

As used herein, the terms "protein of interest", "polypeptide of interest", "peptide of interest", "POI", "targeted protein", "targeted polypeptide", and "targeted peptide" will be used interchangeably and refer to a protein, polypeptide, or peptide targeted for production that is bioactive and may be expressed by the genetic machinery of a host cell. In one embodiment, the peptide of interest comprises at least one body surface-binding peptide selected from the group consisting of hair-binding peptides, skin-binding peptides, nail-binding peptides, and teeth-binding peptides.

As used herein, the terms "bioactive", "active", and "peptide of interest activity" are used interchangeably and refer to the peptides having a defined activity, function, property or use making them desirable for industrial/commercial applications. The bioactive peptides may be used in a variety of applications including, but not limited to curative agents for diseases (e.g., insulin, interferon, interleukins, anti-angiogenic peptides (U.S. Pat. No. 6,815,426), and polypeptides that bind to defined cellular targets such as receptors, channels, lipids, cytosolic proteins, membrane proteins, peptides having antimicrobial activity, peptides having an affinity for a particular material (e.g., hair-binding peptides, skin-binding peptides, nail-binding peptides, teeth-binding peptides, cellulose-binding peptides, polymer-binding peptides, clay-binding peptides, silica-binding polypeptides, carbon nanotube binding polypeptides, and peptides that have an affinity for particular animal or plant tissues) for targeted delivery of benefit agents. In one embodiment, the affinity peptide is the benefit agent (e.g., the peptide of interest is a conditioning agent).

As used herein, the term "genetic construct" refers to a series of contiguous nucleic acids useful for modulating the genotype or phenotype of an organism. Non-limiting examples of genetic constructs include but are not limited to a nucleic acid molecule, an open reading frame, a gene, a plasmid, and the like.

The term "amino acid" refers to the basic chemical structural unit of a protein or polypeptide. The following abbreviations are used herein to identify specific amino acids:

| Amino Acid | Three-Letter Abbreviation | One-Letter Abbreviation |
|---|---|---|
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |
| Any amino acid or as defined herein | Xaa | X |

As used herein, "gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. A "foreign" gene refers to a gene not normally found in the host organism, but that is introduced into the host organism by gene transfer. Foreign genes can comprise native genes inserted into a non-native organism, or chimeric genes. "Synthetic genes" can be assembled from oligonucleotide building blocks that are chemically synthesized using procedures known to those skilled in the art. These building blocks are ligated and annealed to form gene segments which are then enzymatically assembled to construct the entire gene. "Chemically synthesized", as related to a sequence of DNA, means that the component nucleotides were assembled in vitro. Manual chemical synthesis of DNA may be accomplished using well-established procedures, or automated chemical synthesis can be performed using one of a number of commercially available machines. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

Means to prepare the present peptides (inclusion body tags, cleavable peptide linkers, cross-linkable cysteine moieties, peptides of interest, and fusion peptides) are well known in the art (see, for example, Stewart et al., *Solid Phase Peptide Synthesis*, Pierce Chemical Co., Rockford, Ill., 1984; Bodanszky, *Principles of Peptide Synthesis*, Springer-Verlag, New York, 1984; and Pennington et al., *Peptide Synthesis Protocols*, Humana Press, Totowa, N.J., 1994). The various components of the fusion peptides (inclusion body tag, peptide of interest, and the cleavable linker) described herein can be combined using carbodiimide coupling agents (see for example, Hermanson, Greg T., *Bioconiugate Techniques*, Academic Press, New York (1996)), diacid chlorides, diisocyanates and other difunctional coupling reagents that are reactive to terminal amine and/or carboxylic acid groups on the peptides.

Standard recombinant DNA and molecular cloning techniques used herein are well known in the art and are described by Sambrook, J. and Russell, D., *Molecular Cloning: A Laboratory Manual*, Third Edition, Cold Spring Harbor Laboratory Press, Cold Spring Harbor, N.Y. (2001); and by Silhavy, T. J., Bennan, M. L. and Enquist, L. W., *Experiments with Gene Fusions*, Cold Spring Harbor Laboratory Cold Press Spring Harbor, N.Y. (1984); and by Ausubel, F. M. et. al., *Short Protocols in Molecular Biology*, 5$^{th}$ Ed. Current Protocols and John Wiley and Sons, Inc., N.Y., 2002.

Inclusion Body Tags

Fusion proteins comprising a protein tag ("inclusion body fusion partner") that facilitate the expression of insoluble proteins are well known in the art. The art typically uses inclusion body fusion partners (also referred to as "inclusion body tags" or "solubility tags") that are quite large, increasing the likelihood that the fusion protein will be insoluble. Examples of large peptide tags typically used include, but are not limited to chloramphenicol acetyltransferase (Dykes et al., *Eur. J. Biochem.*, 174:411 (1988), β-galactosidase (Schellenberger et al., *Int. J. Peptide Protein Res.*, 41:326 (1993); Shen et al., *Proc. Nat. Acad. Sci. USA* 281:4627 (1984); and Kempe et al., *Gene*, 39:239 (1985)), glutathione-S-transferase (Ray et al., *Bio/Technology*, 11:64 (1993) and Hancock et al. (WO94/04688)), the N-terminus of L-ribulokinase (U.S. Pat. No. 5,206,154 and Lai et al., *Antimicrob. Agents & Chemo.*, 37:1614 (1993), bacteriophage T4 gp55 protein (Gramm et al., *Bio/Technology*, 12:1017 (1994), bacterial ketosteroid isomerase protein (Kuliopulos et al., *J. Am. Chem. Soc.* 116:4599 (1994), ubiquitin (Pilon et al., *Biotechnol. Prog.*, 13:374-79 (1997), bovine prochymosin (Naught et al., *Biotechnol. Bioengineer.* 57:55-61 (1998), and bactericidal/permeability-increasing protein ("BPI"; Better, M. D. and Gavit, P D., U.S. Pat. No. 6,242,219). The art is replete with specific examples of this technology, see for example U.S. Pat. No. 6,613,548, describing fusion protein of proteinaceous tag and a soluble protein and subsequent purification from cell lysate; U.S. Pat. No. 6,037,145, teaching a tag that protects the expressed chimeric protein from a specific protease; U.S. Pat. No. 5,648,244, teaching the synthesis of a fusion protein having a tag and a cleavable linker for facile purification of the desired protein; and U.S. Pat. Nos. 5,215,896; 5,302,526; 5,330,902; and U.S. Patent application publication No. 2005/221444, describing fusion tags containing amino acid compositions specifically designed to increase insolubility of the chimeric protein or peptide.

Shorter inclusion tags have recently been developed from the *Zea mays* zein protein (co-pending U.S. patent application Ser. No. 11/641,936), the *Daucus carota* cystatin protein (co-pending U.S. patent application Ser. No. 11/641,273), an amyloid-like hypothetical protein from *Caenorhabditis elegans* (co-pending U.S. patent application Ser. No. 11/516,362, and tags comprising a β-sheet tape architecture (Aggeli et al., *J. Amer. Chem. Soc.*, 125:9619-9628 (2003); Aggeli et al., *PNAS*, 98(21):11857-11862 (2001); Aggeli et al., *Nature*, 386:259-262 (1997); Aggeli et al., *J. Mater Chem*, 7(7):1135-1145 (1997); and co-pending U.S. patent application Ser. No. 11/782,836. The use of short inclusion body tags increases the total amount of the target peptide produced (i.e. more of the fusion protein is the peptide of interest).

However, subsequent processing to separate the smaller inclusion body tag from the peptide of interest is sometimes difficult, especially when the inclusion body tag and the peptide of interest have similar solubility characteristics. As such, the present process provides a cost effective means to separate the inclusion body tag from the peptide of interest upon cleavage.

Inclusion Body Tags Comprising Cross-Linkable Cysteine Residues

The present method uses oxidative cross-linking to selectively precipitate an inclusion body tag. The inclusion body tag generally has an effective number of cross-linkable cysteine residues while the peptide of interest is devoid of cross-linkable cysteine residues.

One of skill in the art can recombinantly engineer an effective number of cross-linkable cysteine residues into the portion of the fusion protein targeted for oxidative cross-linking. In one embodiment, the inclusion body tag comprises 3 or more cysteine residues, preferably 4 or more cysteine residues, more preferably 3 to about 20, even more preferably 3 to about 10, more preferably 3 to about 5, and most preferably 4 or 5 cross-linkable cysteine residues. The inclusion body tags previously reported in the art that do not contain at least 3 cysteine residues can be modified to include an effective amount of cysteine residues to facilitate selective cross-linking. As such, any inclusion body tag previously reported can be easily modified to include an effective number of cysteine residues using any number of well-known techniques known in the art of molecular biology. In another embodiment, previously reported inclusion body tags can be modified to comprise 3 or more cysteine residues, preferably 4 or more cysteine residues, more preferably 3 to about 20, even more preferably 3 to about 10, more preferably 3 to about 5, and most preferably 4 or 5 cross-linkable cysteine residues.

In a preferred embodiment, the length of the inclusion body tag is minimized to increase the amount of the peptide of interest in the fusion protein. In one embodiment, the inclusion body tag comprising an effective number of cross-linkable cysteine residues is less than 125 amino acids in length, preferably less than 100 amino acids in length, more preferably less than 75 amino acids in length, even more preferably less than 50 amino acids in lengths, yet even more preferably less than 25 amino acids in length, and most preferably less than about 15 amino acids in length. Means to identify small inclusion body tags have been reported in the art (U.S. patent application Ser. Nos. 11/641,936, 11/641,273, 11/641,981, and 11/516,362).

The cysteine residues can be dispersed throughout the inclusion body tag and/or may be located on the amino and/or carboxy terminus of the inclusion body tag. In one embodiment, an effective number of cross-linkable cysteine residues are added to a short inclusion body tag (e.g., no more than 125 amino acids in length). In another embodiment, a cross-linkable cysteine motif may also be incorporated into the portion of the fusion protein comprising the inclusion body tag to provide an effective number of cross-linkable cysteine residues. When adding a cross-linkable cysteine motif to an inclusion body tag (i.e. one that previously did not contain an effective number of cross-linkable cysteine residues), it is desirable to use a motif that is relatively short in order to minimize the impact on peptide yield. In one embodiment, the cross-linkable cysteine motif is operably linked to the inclusion body tag and comprises 3 or more cysteine residues, preferably 4 or more cysteine residues, more preferably 3 to about 20, even more preferably 3 to about 10, more preferably 3 to about 5, and most preferably 4 or 5 cross-linkable cysteine residues wherein the addition of the cross-linkable cysteine motif provides and effective number of cross-linkable cysteine residue to the inclusion body tag. In a preferred embodiment, the inclusion body tag is comprises the tetra-cysteine moiety (Cys-Cys-Xaa$_1$-Xaa$_2$-Cys-Cys; SEQ ID NO: 30) wherein Xaa$_1$ and Xaa$_2$ is any amino acid. In a preferred embodiment, Xaa$_1$ is Pro and Xaa$_2$ is Gly (Cys-Cys-Pro-Gly-Cys-Cys; SEQ ID NO: 32).

In one embodiment, the fusion peptide includes at least one cleavage site (CS) useful in separating the peptide of interest from the inclusion body tag(s). In another embodiment, the cleavage site is provided by a cleavable peptide linker. The CS can be an enzymatic cleavage sequence or a chemical cleavage sequence. In another preferred embodiment, the cleavable peptide linker comprises at least one acid cleavable aspartic acid-proline moiety (i.e. a "DP" acid cleavage moiety).

Peptides of Interest (POIs) Comprising Cross-Linkable Cysteine Residues

The peptide of interest may contain (or be modified to contain) an effective number of cross-linkable cysteine residues. In this embodiment, the inclusion body tags are designed to be devoid of any cross-linkable cysteine residues. The cross-linkable cysteine residues may be dispersed throughout the peptide of interest or may be incorporated into the portion of the fusion protein comprising the peptide of interest in the form of a cross-linkable cysteine moiety. In a further embodiment, a cross-linkable cysteine moiety may also be added to the amino or carboxy terminus of the peptide of interest (for example, to provide an effective number of cross-linkable cysteine residues to the peptide of interest) when the portion comprising the inclusion body tag is devoid of cysteine residues so long as the addition of the cross-linkable cysteine moiety does not adversely impact the activity/functionality of the peptide of interest. Means to determine the impact of incorporating one or more additional cysteine residues to the portion of the fusion protein encoding the peptide of interest are well known in the art and will depend upon the nature of the peptide of interest (e.g. enzymatic activity, binding affinity, etc.). One of skill in the art can compare the functionality of the cysteine-modified POI versus the unmodified version to determine the impact on the desired functionality of the POI.

Expressible Peptides of Interest

The peptide of interest ("expressible peptide" or "POI") targeted for production using the present method is one that is appreciably soluble in the host cell and/or host cell liquid lysate under normal physiological conditions. In a preferred aspect, the peptides of interest are generally short (<300 amino acids in length) and difficult to produce in sufficient amounts due to proteolytic degradation and/or difficult to isolate due to their high solubility. Fusion of the peptide of interest to at least one inclusion body tag creates a fusion peptide that is typically insoluble in the host cell and/or host cell lysate under normal physiological conditions. Production of the peptide of interest is typically increased when expressed and accumulated in the form of an insoluble inclusion body as the peptide is generally more protected from proteolytic degradation. Furthermore, the insoluble fusion protein (typically in the form of an inclusion body) can be easily separated from the host cell lysate using centrifugation or filtration.

Inclusion body tags can be used in a process to produce any peptide of interest that is (1) typically soluble in the cell and/or cell lysate under typical physiological conditions and/or (2) those that can be produced at significantly higher levels when expressed in the form of an inclusion body. In a preferred embodiment, the peptide of interest is appreciably soluble in the host cell and/or corresponding cell lysate under normal physiological and/or process conditions.

The length of the peptide of interest may vary as long as (1) the peptide is appreciably soluble in the host cell and/or cell lysate, and/or (2) the amount of the targeted peptide produced is increased when expressed in the form of an insoluble fusion peptide/inclusion body (i.e. expression in the form of a fusion protein protect the peptide of interest from proteolytic degradation). Typically the peptide of interest is less than 300 amino acids in length, preferably less than 200 amino acids in length, preferably less than 150 amino acids in length, more preferably less than 100 amino acids in length, even more preferably less than 80 amino acids in length, and most preferably less than 50 amino acids in length.

The function of the peptide of interest is not limited by the present method and may include, but is not limited to bioactive molecules such as curative agents for diseases (e.g., insulin, interferon, interleukins, peptide hormones, anti-angiogenic peptides, and peptides that bind to and affect defined cellular targets such as receptors, channels, lipids, cytosolic proteins, and membrane proteins; see U.S. Pat. No. 6,696, 089), peptides having an affinity for a particular material (e.g., biological tissues, biological molecules, hair-binding peptides (U.S. Pat. No. 7,220,405; U.S. patent application Ser. No. 11/074,473; WO 0179479; U.S. Patent Application Publication No. 2002/0098524; U.S. Patent Application Publication No. 2003/0152976; WO 04048399; U.S. patent application Ser. Nos. 11/512,910; and 11/696,380), skin-binding peptides (U.S. Pat. No. 7,220,405; U.S. patent application Ser. No. 11/069,858; WO 2004/000257; and U.S. patent application Ser. No. 11/696,380), nail-binding peptides (U.S. Pat. No. 7,220,405; U.S. patent application Ser. No. 11/696,380), teeth-binding peptide (U.S. patent application Ser. No. 11/877,692), cellulose-binding peptides, polymer-binding peptides (nylon-binding peptides (U.S. patent application Ser. No. 11/607,723); polytetrafluoroethylene-binding peptides (U.S. patent application Ser. No. 11/607, 734); polyethylene-binding peptides (U.S. patent application Ser. No. 11/607,672); polystyrene-binding peptides (U.S. patent application Ser. No. 11/607,673); polypropylene-binding peptides (U.S. patent application Ser. No. 11/607,792); polymethylmethacrylate-binding peptides (U.S. patent application Ser. No. 11/607,732)), clay binding peptides (U.S. patent application Ser. No. 11/696,380), silicon binding peptides, and carbon nanotube binding peptides (U.S. patent application Ser. Nos. 11/093,533 and 11/093,873) for targeted delivery of at least one benefit agent (see U.S. Pat. No. 7,220,405; U.S. patent application Ser. Nos. 10/935,642; and 11/074,473).

In one embodiment, the peptide of interest is selected from the group consisting of antimicrobial peptides (SEQ ID NOs: 74-102), polymer-binding peptides (SEQ ID NOs: 135-162), and the clay-binding peptides (SEQ ID NOs: (163-178).

Peptides of Interest—Body Surface-Binding Peptides: Hair-Binding Peptides, Nail-Binding Peptides, Skin-Binding Peptides, and Teeth-Binding Peptides Hair-binding peptides (HBPs), nail-binding peptides (NBPs), skin-binding peptides (SBPs), and teeth-binding peptides (TBPs) as defined herein are peptide sequences that bind with high affinity to hair, nail, skin or teeth; respectively. The hair-binding peptides, nail-binding peptides, skin-binding peptides, and teeth-binding peptides are typically from about 7 amino acids to about 100 amino acids in length, more preferably about 7 amino acids to about 50 amino acids in length, and most preferably about 7 to about 30 amino acids in length. Suitable hair-, nail-, skin-, and teeth-binding peptides may be selected using methods that are well known in the art or may be empirically generated The hair-, nail-, skin- or teeth-binding peptides may be generated randomly and then selected against a specific hair, nail, skin, or tooth surface sample based upon their binding affinity for the substrate of interest, as described by Huang et al. in U.S. Patent Application Publication No. 2005/0050656 or O'Brien et al. in U.S. patent application Ser. No. 11/877, 692 or by a method using mRNA-display as described in U.S. patent application Ser. No. 11/696,380, each incorporated herein by reference. The generation of random libraries of peptides is well known and may be accomplished by a variety of techniques including, bacterial display (Kemp, D. J.; Proc. Natl. Acad. Sci. USA 78(7):4520-4524 (1981), and Helfman et al., Proc. Natl. Acad. Sci. USA 80(1):31-35, (1983)), yeast display (Chien et al., Proc Natl Acad Sci USA 88(21):9578-82 (1991)), combinatorial solid phase peptide synthesis (U.S. Pat. Nos. 5,449,754, 5,480,971, 5,585,275, 5,639,603), phage display technology (U.S. Pat. Nos. 5,223,409, 5,403,484, 5,571,698, 5,837,500), ribosome display technology (U.S. Pat. Nos. 5,643,768; 5,658,754; and 7,074,557), and mRNA display technology (U.S. Pat. Nos. 6,258,558; 6,518,018; 6,281,344; 6,214,553; 6,261,804; 6,207,446; 6,846,655; 6,312,927; 6,602,685; 6,416,950; 6,429,300; 7,078,197; 6,436,665; 6,361,943; and 6,228,994).

Any hair-binding, skin-binding, nail-binding or teeth-binding peptide may be used, such as those reported in co-pending and commonly owned U.S. Patent Application Publication No. 2005/0050656; U.S. Patent Application Publication No. 2005/0226839, and U.S. patent application Ser. No. 11/877,692; Estell et al. (WO 0179479); Murray et al., (U.S. Patent Application Publication No. 2002/0098524); Janssen et al., (U.S. Patent Application Publication No. 2003/ 0152976); Janssen et al., (WO 04048399), O'Brien et al. (co-pending and commonly owned U.S. Patent Application Publication No. 2006/0073111), Wang et al. (co-pending and commonly owned U.S. patent application Ser. No. 11/359, 163) and Wang et al. (co-pending and commonly owned U.S. patent application Ser. No. 11/359,162), all of which are incorporated herein by reference.

In another preferred aspect, the hair-binding peptide is selected from the group consisting of SEQ ID NOs: 9, 10, 12, 15, 17, 22, and 35-58; the skin-binding peptide is selected from the group consisting of SEQ ID NOs: 38-42 and 59-71; the nail-binding peptide is selected from the group consisting of SEQ ID NOs: 72-73, and the teeth-binding peptides is selected from the group consisting of SEQ ID NOs: 185-224. In another embodiment, the peptide of interest is a non-naturally occurring peptide identified from a combinatorially-generated library of peptides.

Alternatively, hair-, nail-, and skin-binding peptide sequences may also be generated empirically by designing peptides that comprise positively charged amino acids, which can bind to hair and skin via electrostatic interaction, as described by Rothe et al. (WO 2004/000257). The empirically generated hair, nail, and skin-binding peptides have between about 7 amino acids to about 50 amino acids, and comprise at least about 40 mole % positively charged amino acids, such as lysine, arginine, and histidine. Peptide sequences containing tripeptide motifs such as HRK, RHK, HKR, RKH, KRH, KHR, HKX, KRX, RKX, HRX, KHX and RHX are most preferred where X can be any natural amino acid but is most preferably selected from neutral side chain amino acids such as glycine, alanine, proline, leucine, isoleucine, valine and phenylalanine. In addition, it should be understood that the peptide sequences must meet other functional requirements in the end use including solubility, viscosity and compatibility with other components in a formulated product and will therefore vary according to the needs of the application. In some cases the peptide may contain up to 60 mole % of amino acids not comprising histidine, lysine or arginine. Suitable empirically generated hair-binding, nail-binding, and skin-binding peptides include, but are not limited to, SEQ ID NOs: 38-42 (see Table 1).

It may also be beneficial to use a mixture of different hair-binding, nail-binding, or skin-binding peptides. The peptides in the mixture need to be chosen so that there is no interaction between the peptides that mitigates the beneficial effect. Suitable mixtures of hair-binding, nail-binding or skin-binding peptides may be determined by one skilled in the art using routine experimentation. Additionally, it may be desirable to link two or more hair-binding peptides, nail-binding peptides or skin-binding peptides together, either directly or through a spacer, to enhance the interaction of the peptide to the substrate. Methods to prepare the multiple peptide compositions and suitable spacers are described below. Non-limiting examples are given in Table 1.

TABLE 1

Examples of Hair-Binding Peptides, Nail-Binding Peptides, Skin-Binding Peptides, and Teeth-Binding Peptides

| Body Surface | SEQ ID NO: | Sequence |
|---|---|---|
| Hair (Shampoo Resistant) | 35 | TPPELLHGDPRS |
| Hair (Shampoo Resistant) | 9 | NTSQLST (also referred to herein as KF11) |
| Hair | 10 | RTNAADHP (also referred to herein as D21) |
| Hair | 36 | RTNAADHPAAVT |
| Hair | 15 | IPWWNIRAPLNA (also referred to herein as A09) |
| Hair | 37 | DLTLPFH |
| Hair and Skin (empirical) | 38 | KRGRHKRPKRHK |
| Hair and Skin (empirical) | 39 | RLLRLLR |
| Hair and Skin (empirical) | 40 | HKPRGGRKKALH |
| Hair and Skin (empirical) | 41 | KPRPPHGKKHRPKHRPKK |
| Hair and Skin (empirical) | 42 | RGRPKKGHGKRPGHRARK |
| Hair (Multi-copy) (also referred to herein as "HC77607") | 12 | GSDPNTSQLSTGGGRTNAADHPKCGGGNTSQLSTGGGRTNAADHPKCGGGNTSQLSTGGGRTNAADHPKC |
| Hair (Multi-copy) | 43 | PRTNAADHPAAVTGGGCGGGRTNAADHPAAVTGGGCGGGRTNAADHPAAVTGGGC |
| Hair (Multi-copy) | 44 | PRTNAADHPAAVTGGGCGGGIPWWNIRAPLNAGGGCGGGDLTLPFHGGGC |
| Hair (Multi-copy) | 45 | PRTNAADHPGGGTPPELLHGDPRSKCGGGRTNAADHPGGGTPPELLHGDPRSKCGGGRTNAADHPGGGTPPELLHGDPRSKC |
| Hair (Multi-copy) | 46 | PTPPTNVLMLATKGGGRTNAADHPKCGGGTPPTNVLMLATKGGGRTNAADHPKCGGGTPPTNVLMLATKGGGRTNAADHPKC |
| Hair (Multi-copy) | 47 | PRTNAADHPGGGTPPTNVLMLATKKCGGGRTNAADHPGGGTPPTNVLMLATKKCGGGRTNAADHPGGGTPPTNVLMLATKKC |
| Hair (with cysteine at C-terminus) | 48 | TPPELLHGDPRSC |
| Hair | 49 | EQISGSLVAAPW |
| Hair | 50 | TDMQAPTKSYSN |
| Hair | 51 | ALPRIANTWSPS |
| Hair | 52 | LDTSFPPVPFHA |
| Hair (Shampoo Resistant) | 53 | TPPTNVLMLATK |
| Hair (Conditioner Resistant) | 54 | STLHKYKSQDPTPHH |
| Hair (Shampoo and Conditioner Resistant) | 55 | GMPAMHWIHPFA |
| Hair (Shampoo and Conditioner Resistant) | 56 | HDHKNQKETHQRHAA |
| Hair (Shampoo and Conditioner Resistant) | 57 | HNHMQERYTDPQHSPSVNGL |
| Hair (Shampoo and Conditioner Resistant) | 58 | TAEIQSSKNPNPHPQRSWTN |

TABLE 1-continued

Examples of Hair-Binding Peptides, Nail-Binding Peptides, Skin-Binding Peptides, and Teeth-Binding Peptides

| Body Surface | SEQ ID NO: | Sequence |
|---|---|---|
| Skin | 59 | TPFHSPENAPGS |
| Skin (Body Wash Resistant) | 60 | TMGFTAPRFPHY |
| Skin (Body Wash Resistant) | 61 | SVSVGMKPSPRP |
| Skin (Body Wash Resistant) | 62 | NLQHSVGTSPVW |
| Skin (Body Wash Resistant) | 63 | QLSYHAYPQANHHAP |
| Skin (Body Wash Resistant) | 64 | SGCHLVYDNGFCDH |
| Skin (Body Wash Resistant) | 65 | ASCPSASHADPCAH |
| Skin (Body Wash Resistant) | 66 | NLCDSARDSPRCKV |
| Skin (Body Wash Resistant) | 67 | NHSNWKTAADFL |
| Skin (Body Wash Resistant) | 68 | SDTISRLHVSMT |
| Skin (Body Wash Resistant) | 69 | SPYPSWSTPAGR |
| Skin (Body Wash Resistant) | 70 | DACSGNGHPNNCDR |
| Skin (Body Wash Resistant) | 71 | DWCDTIIPGRTCHG |
| Nail | 72 | ALPRIANTWSPS |
| Nail | 73 | YPSFSPTYRPAF |
| Tooth (pellicle) | 185 | AHPESLGIKYALDGNSDPHA |
| Tooth (pellicle) | 186 | ASVSNYPPIHHLATSNTTVN |
| Tooth (pellicle) | 187 | DECMEPLNAAHCWR |
| Tooth (pellicle) | 188 | DECMHGSDVEFCTS |
| Tooth (pellicle) | 189 | DLCSMQMMNTGCHY |
| Tooth (pellicle) | 190 | DLCSSPSTWGSCIR |
| Tooth (pellicle) | 191 | DPNESNYENATTVSQPTRHL |
| Tooth (pellicle) | 192 | EPTHPTMRAQMHQSLRSSSP |
| Tooth (pellicle) | 193 | GNTDTTPPNAVMEPTVQHKW |
| Tooth (pellicle) | 194 | NGPDMVQSVGKHKNS |
| Tooth (pellicle) | 195 | NGPEVRQIPANFEKL |
| Tooth (pellicle) | 196 | NNTSADNPPETDSKHHLSMS |
| Tooth (pellicle) | 197 | NNTWPEGAGHTMPSTNIRQA |
| Tooth (pellicle) | 198 | NPTATPHMKDPMHSNAHSSA |
| Tooth (pellicle) | 199 | NPTDHIPANSTNSRVSKGNT |
| Tooth (pellicle) | 200 | NPTDSTHMMHARNHE |
| Tooth (pellicle) | 201 | QHCITERLHPPCTK |
| Tooth (pellicle) | 202 | TPCAPASFNPHCSR |
| Tooth (pellicle) | 203 | TPCATYPHFSGCRA |
| Tooth (pellicle) | 204 | WCTDFCTRSTPTSTSRSTTS |
| Tooth (enamel) | 205 | APPLKTYMQERELTMSQNKD |
| Tooth (enamel) | 206 | EPPTRTRVNNHTVTVQAQQH |
| Tooth (enamel) | 207 | GYCLRGDEPAVCSG |
| Tooth (enamel) | 208 | LSSKDFGVTNTDQRTYDYTT |
| Tooth (enamel) | 209 | NFCETQLDLSVCTV |
| Tooth (enamel) | 210 | NTCQPTKNATPCSA |
| Tooth (enamel) | 211 | PSEPERRDRNIAANAGRFNT |
| Tooth (enamel) | 212 | THNMSHFPPSGHPKRTAT |
| Tooth (enamel) | 213 | TTCPTMGTYHVCWL |
| Tooth (enamel) | 214 | YCADHTPDPANPNKICGYSH |

TABLE 1-continued

Examples of Hair-Binding Peptides, Nail-Binding Peptides, Skin-Binding Peptides, and Teeth-Binding Peptides

| Body Surface | SEQ ID NO: | Sequence |
| --- | --- | --- |
| Tooth (enamel) | 215 | AANPHTEWDRDAFQLAMPPK |
| Tooth (enamel) | 216 | DLHPMDPSNKRPDNPSDLHT |
| Tooth (enamel) | 217 | ESCVSNALMNQCIY |
| Tooth (enamel) | 218 | HNKADSWDPDLPPHAGMSLG |
| Tooth (enamel) | 219 | LNDQRKPGPPTMPTHSPAVG |
| Tooth (enamel) | 220 | NTCATSPNSYTCSN |
| Tooth (enamel) | 221 | SDCTAGLVPPLCAT |
| Tooth (enamel) | 222 | TIESSQHSRTHQQNYGSTKT |
| Tooth (enamel) | 223 | VGTMKQHPTTTQPPRVSATN |
| Tooth (enamel) | 224 | YSETPNDQKPNPHYKVSGTK |

Cleavable Peptide Linkers

The use of cleavable peptide linkers is well known in the art. Fusion peptides comprising the present inclusion body tags will typically include at least one cleavable peptide sequence (i.e. cleavage site or "CS") separating the inclusion body tag from the polypeptide of interest. The cleavable sequence facilitates separation of the inclusion body tag(s) from the peptide(s) of interest. In one embodiment, the cleavable sequence may be provided by a portion of the inclusion body tag and/or the peptide of interest (e.g., inclusion of an acid cleavable aspartic acid-proline moiety). In a preferred embodiment, the cleavable sequence is provided by including (in the fusion peptide) at least one cleavable peptide linker between the inclusion body tag and the peptide of interest.

Means to cleave the peptide linkers are well known in the art and may include chemical hydrolysis, enzymatic cleavage agents, and combinations thereof. In one embodiment, one or more chemically cleavable peptide linkers are included in the fusion construct to facilitate recovery of the peptide of interest from the inclusion body fusion protein. Examples of chemical cleavage reagents include cyanogen bromide (cleaves methionine residues), N-chloro succinimide, iodobenzoic acid or BNPS-skatole [2-(2-nitrophenylsulfenyl)-3-methylindole] (cleaves tryptophan residues), dilute acids (cleaves at aspartyl-prolyl bonds), and hydroxylamine (cleaves at asparagine-glycine bonds at pH 9.0); see Gavit, P. and Better, M., *J. Biotechnol.*, 79:127-136 (2000); Szoka et al., *DNA*, 5(1):11-20 (1986); and Walker, J. M., *The Proteomics Protocols Handbook,* 2005, Humana Press, Totowa, N.J.)). In a preferred embodiment, one or more aspartic acid-proline acid cleavable recognition sites (i.e., a cleavable peptide linker comprising one or more D-P dipeptide moieties) are included in the fusion protein construct to facilitate separation of the inclusion body tag(s) form the peptide of interest. In another embodiment, the fusion peptide may include multiple regions encoding peptides of interest separated by one or more cleavable peptide linkers wherein the regions are separated by one or more cleavable peptide linkers.

In another embodiment, one or more enzymatic cleavage sequences are included in the fusion protein construct to facilitate recovery of the peptide of interest. Proteolytic enzymes and their respective cleavage site specificities are well known in the art. In a preferred embodiment, the proteolytic enzyme is selected to specifically cleave only the peptide linker separating the inclusion body tag and the peptide of interest. Examples of enzymes useful for cleaving the peptide linker include, but are not limited to Arg-C proteinase, Asp-N endopeptidase, chymotrypsin, clostripain, enterokinase, Factor Xa, glutamyl endopeptidase, Granzyme B, *Achromobacter* proteinase I, pepsin, proline endopeptidase, proteinase K, Staphylococcal peptidase I, thermolysin, thrombin, trypsin, and members of the Caspase family of proteolytic enzymes (e.g. Caspases 1-10) (Walker, J. M., supra). An example of a cleavage site sequence is provided by SEQ ID NO: 179 (Caspase-3 cleavage site; Thornberry et al., *J. Biol. Chem.,* 272:17907-17911 (1997) and Tyas et al., *EMBO Reports,* 1(3):266-270 (2000)).

Typically, the cleavage step occurs after the insoluble inclusion bodies and/or insoluble fusion peptides have been separated from the cell lysate. The cells can be lysed using any number of means well known in the art (e.g. mechanical and/or chemical lysis). Methods to collect and/or isolate the insoluble inclusion bodies/fusion peptides from the cell lysate are well known in the art (e.g., centrifugation, filtration, and combinations thereof). Once recovered from the cell lysate, the insoluble inclusion bodies and/or fusion peptides can be treated with a cleavage agent (chemical or enzymatic) to cleavage the inclusion body tag from the peptide of interest. In one embodiment, the fusion protein and/or inclusion body is diluted and/or dissolved in a suitable solvent (e.g., water) prior to treatment with the cleavage agent. The cleavage step is preferably conducted in an aqueous environment.

The inclusion body tag is separated from the peptide of interest using oxidative cross-linking of cysteine residues incorporated into the inclusion body tag or the peptide of interest with the provision that both fragments cannot simultaneously contain an effective number of cross-linkable cysteine residues. Cross-linking of the cysteine residues under oxidative conditions induces the formation of higher molecule weight, insoluble protein agglomerates. The conditions are adjusted so that the portion that does not contain the cross-linked cysteine residues is appreciably soluble under the oxidizing conditions. As such, the portion of fusion protein comprising the inclusion body tag can be easily and efficiently separated from the peptide of interest using simple separation techniques such as centrifugation and/or filtration.

In one embodiment, the peptide of interest is soluble while the inclusion body tag and/or fusion protein is insoluble in the defined process matrix (typically an aqueous matrix). In another embodiment, the peptide of interest is insoluble while the inclusion body tag is soluble in the defined process matrix. When the peptide on interest is cross-linked using the present process, an optional step may be added to reduce the cysteine cross-linking so that the peptide of interest can be isolated/purified in a monomeric and/or soluble form.

In an optional embodiment, the peptide of interest (once isolated after the present cross-linking step) may be further purified using any number of well known purification techniques in the art such as ion exchange, gel purification techniques, and column chromatography (see U.S. Pat. No. 5,648, 244), to name a few.

Fusion Peptides

The fusion peptide should include at least one inclusion body tag (IBT) operably linked to at least one peptide of interest. Typically, the fusion peptide includes at least one cleavable peptide linker having a cleavage site between the inclusion body tag and the peptide of interest. In one embodiment, the inclusion body tag may include a cleavage site whereby inclusion of a separate cleavable peptide linker may not be necessary. In a preferred embodiment, the cleavage method is chosen to ensure that the peptide of interest is not adversely affected by the cleavage agent(s) employed. In a further embodiment, the peptide of interest may be modified to eliminate possible cleavage sites (and/or amino acid residues sensitive to the cleavage agent) with the peptide so long as the desired activity of the peptide is not adversely affected.

One of skill in the art will recognize that the elements of the fusion protein can be structured in a variety of ways. Typically, the fusion protein will include at least one IBT, at least one peptide of interest (POI), and at least one cleavage site (CS; typically in the form of a cleavable linker; CL) located between the IBT and the POI. The inclusion body tag may be organized as a leader sequence or a terminator sequence relative to the position of the peptide of interest within the fusion peptide. In another embodiment, a plurality of IBTs, POIs, and cleavage sites are used when engineering the fusion peptide. In a further embodiment, the fusion peptide may include a plurality of IBTs (as defined herein), POIs, and cleavage sites that are the same or different.

The fusion peptide is typically insoluble in an aqueous matrix at a temperature of 10° C. to 50° C., preferably 10° C. to 40° C. under normal physiological conditions. The aqueous matrix typically comprises a pH range of 5 to 12, preferably 6 to 10, and most preferably 6 to 8. The temperature, pH, and/or ionic strength of the aqueous matrix can be adjusted to obtain the desired solubility characteristics of the fusion peptide. For example, prior to acid cleavage, the conditions may be adjusted to solubilize the isolated fusion protein.

Method to Make a Peptide of Interest Using Insoluble Fusion Peptides

Chimeric genes are constructed using techniques well known in the art. The chimeric constructs are designed to encode at least one peptide of interest operably linked (via a cleavable peptide linker) to at least one inclusion body tag. Expression of the chimeric genetic construct produces an insoluble form of the peptide of interest that accumulates in the form of inclusion bodies within the host cell. The host cell is grown for a period of time sufficient for the insoluble fusion peptide to accumulate in the form of inclusion bodies within the cell.

The host cell is subsequently lysed using any number of techniques well known in the art. The insoluble fusion peptides/inclusion bodies are then separated from the other components of the cell lysate using a simple and economical technique such as centrifugation and/or membrane filtration. The insoluble fusion peptide/inclusion body can then be further processed in order to isolate the peptide of interest. Typically, this will include resuspension of the fusion peptide/inclusion body in a liquid matrix suitable for cleaving the fusion peptide. The cleavage step can be conducted using any number of techniques well known in the art (chemical cleavage, enzymatic cleavage, and combinations thereof) wherein acid cleavage is preferred.

After cleavage, the mixture of fusion peptide fragments is subjected to oxidative cross-linking whereby one of the components is selectively cross-linked to facilitate separation. The cross-linked component is separated from the soluble component(s) using any numbers of techniques known in the art. In a preferred embodiment, centrifugation and/or filtration is used to separate the cross-linked material from the non-cross-linked material.

Transformation and Expression

Recombinant expression of the chimeric genes encoding the desired fusion protein can be prepared using techniques well known in the art. Typically, the chimeric constructs are engineered and expressed from a vector transformed into an appropriate host cell. Typically, the vector or cassette contains sequences directing transcription and translation of the relevant chimeric gene, a selectable marker, and sequences allowing autonomous replication or chromosomal integration. Suitable vectors comprise a region 5' of the gene which harbors transcriptional initiation controls and a region 3' of the DNA fragment which controls transcriptional termination. It is most preferred when both control regions are derived from genes homologous to the transformed host cell, although it is to be understood that such control regions need not be derived from the genes native to the specific species chosen as a production host.

Initiation control regions or promoters, which are useful to drive expression of the genetic constructs encoding the fusion peptide in the desired host cell, are numerous and familiar to those skilled in the art. Virtually any promoter capable of driving these constructs is suitable for the present invention including but not limited to CYC1, HIS3, GAL1, GAL10, ADH1, PGK, PHO5, GAPDH, ADC1, TRP1, URA3, LEU2, ENO, TPI (useful for expression in *Saccharomyces*); AOX1 (useful for expression in *Pichia*); and lac, ara (pBAD), tet, trp, $IP_L$, $IP_R$, T7, tac, and trc (useful for expression in *Escherichia coli*) as well as the amy, apr, npr promoters and various phage promoters useful for expression in *Bacillus*.

Termination control regions may also be derived from various genes native to the preferred hosts. Optionally, a termination site may be unnecessary, however, it is most preferred if included.

Preferred host cells for expression of the fusion peptide are microbial hosts that can be found broadly within the fungal or bacterial families and which grow over a wide range of temperature, pH values, and solvent tolerances. For example, it is contemplated that any of bacteria, yeast, and filamentous fungi will be suitable hosts for expression of the nucleic acid molecules encoding fusion peptides. Because of transcription, translation, and the protein biosynthetic apparatus is the same irrespective of the cellular feedstock, genes are expressed irrespective of the carbon feedstock used to generate the cellular biomass. Large-scale microbial growth and functional gene expression may utilize a wide range of simple or complex carbohydrates, organic acids and alcohols (i.e. methanol), saturated hydrocarbons such as methane or carbon dioxide in the case of photosynthetic or chemoautotrophic hosts. However, the functional genes may be regulated, repressed or depressed by specific growth conditions, which may include the form and amount of nitrogen, phosphorous, sulfur, oxygen, carbon or any trace micronutrient including small inorganic ions. In addition, the regulation of functional genes may be achieved by the presence or absence of specific regulatory molecules that are added to the culture and are not typically considered nutrient or energy sources. Growth rate may also be an important regulatory factor in gene expression. Examples of host strains include, but are not limited to fungal or yeast species such as *Aspergillus, Trichoderma, Saccharomyces, Pichia, Yarrowia, Candida, Hansenula*, or bacterial species such as *Salmonella, Bacillus,*

*Acinetobacter, Zymomonas, Agrobacterium, Erythrobacter, Chlorobium, Chromatium, Flavobacterium, Cytophaga, Rhodobacter, Rhodococcus, Streptomyces, Brevibacterium, Corynebacteria, Mycobacterium, Deinococcus, Escherichia, Erwinia, Pantoea, Pseudomonas, Sphingomonas, Methylomonas, Methylobacter, Methylococcus, Methylosinus, Methylomicrobium, Methylocystis, Alcaligenes, Synechocystis, Synechococcus, Anabaena, Thiobacillus, Methanobacterium, Klebsiella*, and *Myxococcus*. Preferred bacterial host strains include *Escherichia, Pseudomonas*, and *Bacillus*. In a preferred aspect, the bacterial host strain is *Escherichia coli*.

Fermentation Media

Fermentation media in the present invention must contain suitable carbon substrates. Suitable substrates may include, but are not limited to monosaccharides such as glucose and fructose, oligosaccharides such as lactose or sucrose, polysaccharides such as starch or cellulose or mixtures thereof and unpurified mixtures from renewable feedstocks such as cheese whey permeate, cornsteep liquor, sugar beet molasses, and barley malt. Additionally the carbon substrate may also be one-carbon substrates such as carbon dioxide, or methanol for which metabolic conversion into key biochemical intermediates has been demonstrated. In addition to one and two carbon substrates methylotrophic organisms are also known to utilize a number of other carbon containing compounds such as methylamine, glucosamine and a variety of amino acids for metabolic activity. For example, methylotrophic yeast are known to utilize the carbon from methylamine to form trehalose or glycerol (Bellion et al., *Microb. Growth C1 Compd.*, [Int. Symp.], 7th (1993), 415-32. Editor (s): Murrell, J. Collin; Kelly, Don P. Publisher: Intercept, Andover, UK). Similarly, various species of *Candida* will metabolize alanine or oleic acid (Sulter et al., *Arch. Microbiol.* 153:485-489 (1990)). Hence it is contemplated that the source of carbon utilized in the present invention may encompass a wide variety of carbon containing substrates and will only be limited by the choice of organism.

Although it is contemplated that all of the above mentioned carbon substrates and mixtures thereof are suitable in the present invention, preferred carbon substrates are glucose, fructose, and sucrose.

In addition to an appropriate carbon source, fermentation media must contain suitable minerals, salts, cofactors, buffers and other components, known to those skilled in the art, suitable for the growth of the cultures and promotion of the expression of the present fusion peptides.

Culture Conditions

Suitable culture conditions can be selected dependent upon the chosen production host. Typically, cells are grown at a temperature in the range of about 25° C. to about 40° C. in an appropriate medium. Suitable growth media in the present invention are common commercially prepared media such as Luria Bertani (LB) broth, Sabouraud Dextrose (SD) broth or Yeast medium (YM) broth. Other defined or synthetic growth media may also be used and the appropriate medium for growth of the particular microorganism will be known by one skilled in the art of microbiology or fermentation science. The use of agents known to modulate catabolite repression directly or indirectly, e.g., cyclic adenosine 2':3'-monophosphate, may also be incorporated into the fermentation medium.

Suitable pH ranges for the fermentation are typically between pH 5.0 to pH 9.0, where about pH 6.0 to about pH 8.0 is preferred.

Fermentations may be performed under aerobic or anaerobic conditions wherein aerobic conditions are preferred.

Process Steps Prior to Cysteine Cross-Linking

Recombinant production of fusion peptides/proteins in the form of inclusion bodies is well known in the art. Typically, the recombinant cells (comprising the fusion protein) are homogenized to release the insoluble inclusion bodies. Isolation of inclusion bodies from a cell lysate are based on well known techniques including, but not limited to centrifugation and/or filtration. The process typically involves several cycles of each process step (i.e. homogenization, centrifugation, washing etc.) for optimal processing. Washing and/or concentration adjustments using water are typically employed between each process step/cycle. The pH is adjusted, as needed, for optimal processing. In general, the following basic processing options may be used to obtain a semi-purified and/or purified inclusion body paste.

The process begins with a fermentation broth comprising a population of recombinant microbial host cells comprising insoluble fusion protein in the form of an inclusion body.

Option 1—Using Initial Cell Separation from Fermentation Broth as a First Step.

The fermentation broth is either centrifuged or passed through a membrane filtration process to separate and recover cells containing inclusion bodies of the peptide to be recovered. Water and dissolved impurities and salts are removed. The recovered cell mass is re-suspended in water at a concentration of about 10 to about 250 g/L wet cells. The pH of the mixture is adjusted to a pH of about 9 to about 12, more preferentially about 10 to about 11 using a simple strong base like NaOH. The mixture is then cooled to about 0° to about 10° C. The mixture is passed through a mechanical high pressure homogenization device like a Mouton-Gaulin homogenizer at from about 8,000 psi (approximately 55.2 mPa) to about 25,000 psi (approximately 172 mPa), more preferentially about 10,000 psi (approximately 69.0 mPa) to about 15,000 psi (approximately 103 mPa), nominally about 12,000 psi (approximately 82.8 mPa) for several passes. The number of passes through the homogenizer may be varied as needed. In one embodiment, the number of passes through the homogenizer is about 1 to about 5, preferably 1 to 3, and most preferably about 3. The temperature of liquid during homogenization is preferably maintained at a temperature of about 0° C. to about 30° C., preferably about 0° C. to about 10° C.

After the final homogenization pass, the homogenized mixture is subjected to centrifugation and/or filtration. In a preferred embodiment, centrifugation (e.g. stacked disc centrifugation) is used to separate the insoluble inclusion bodies from the lysate. The concentration of lysed cell biomass is optionally adjusted to a lower concentration with water prior to centrifugation to 10 to 200 g/L, preferably 50 to 150 g/L, and most preferably about 75 g/L.

Differential settling of the inclusion bodies to a paste occurs and the overflow of the centrifuge contains the cell debris containing fraction. The recovered inclusion body rich paste is then re-suspended in water. The suspension is well mixed and re-centrifuged or membrane filtered to remove dissolved salts and residual contaminants. If needed, additional water washes may be used.

Option 2—Direct Processing of the Fermentation Broth

Direct process of the fermentation broth may also be used. The process is essentially identical to Option 1, except that the fermentation broth is directly processed (no prior centrifugation and/or filtration steps used to isolate the cells prior to homogenization).

Option 3—The Fermentation Broth is pH Adjusted Before Homogenization

In another embodiment, pH of the fermentation broth may be adjusted prior to homogenization. This option is similar to Option 2, except that the pH of the fermentation broth is adjusted to a pH of about 9 to about 12, more preferentially about 10 to about 11 prior to homogenization.

High pH Wash Followed by Water Wash

A high pH wash may be used to further purify the inclusion body paste. The concentrated inclusion body paste obtained after centrifugation is adjusted using a 1 M $NaHCO_3$ pH10 buffer to a final concentration of about 50 mM buffer. The suspension is mixed and centrifuged using a centrifuge (e.g. a stacked disk centrifuge) to separate the dissolved and suspended impurities from the inclusion bodies.

The inclusion body slurry is diluted and washed in water to remove the buffer. Centrifugation is repeated to isolate the washed inclusion body paste.

Cleavage and Oxidative Cross-Linking

In one embodiment, the semi-purified insoluble fusion protein (inclusion body paste) is re-suspended in water and subjected to a cleavage step whereby the fusion protein is cleaved into a mixture of free inclusion body tag(s), free peptides of interest. The mixture may also include some partially-cleaved and/or whole fusion proteins. As described previously, the fusion protein comprises one or more cleavable peptide sequences (e.g. cleavable peptide linkers) separating the inclusion body tags from the peptides of interest. The cleavable peptide linker may be cleaved enzymatically and/or chemically (e.g. acid cleavage).

In a preferred embodiment, acid cleavage is used. The inclusion body slurry is adjusted to the desired solids concentration (typically about 25 g/L on a dry weight basis). The pH of the aqueous solution of fusion peptides is adjusted so that the acid labile D-P moieties are cleaved. A reducing agent, such as dithiothreitol (DTT, 10 mM) may also be used during acid hydrolysis to break disulfide bonds and to promote acid cleavage. Any suitable acid may be used including, but not limited to HCl, formic acid, nitric acid, sulfuric acid, phosphoric acid, citric acid, trifluoroacetic acid, and mixtures thereof. One of skill in the art can adjust the time, temperature, and pH for optimal cleavage. Typically, the acid treatment is conducted at a pH range of about 0.5 to about 3, more preferably 1.5 to 2.6, most preferably 1.8 to 2.2. The mixture is heated to a temperature of about 40° C. to about 90° C., preferably 50° C. to about 90° C., more preferably 60° C. to about 80° C., and most preferably about 70° C. The heated acidic mixture is held for a period of time from 30 minutes to 48 hours, preferably less than 24 hours, even more preferably less than 12 hours, and most preferably less than 8 hours to achieve effective cleavage.

The cleaved peptide mixture is then cooled to a temperature of about 25° C. and the pH is adjusted to about 5.1 (or the corresponding isoelectric point [pI] of the portion containing the plurality of cross-linkable cysteine residues). The pH adjusted solution is further cooled to a temperature of about 0° C. to about 20° C., more preferably about 0° C. to about 10° C., and most preferably about 5° C. and slowly agitated with a slow bubbling of filtered air to create an oxidizing environment. The mixture is allowed to cross-link and precipitate for a period of time sufficient to achieve effective cross-linking. The optimal time required for effective cross-linking step can be easily determined by one of skill in the art. Typically, the cross-linking step typically ranges in time from 5 minutes to about 48 hours, preferably 30 minutes to 24 hours, more preferably about 1 hour to about 12 hours, and most preferably about 2 to about 8 hours. The sediment (i.e. the cross-linked peptide aggregate) is separated from the supernatant by centrifugation and/or filtration (including microfiltration).

The next processing step is dependent upon which element (i.e. inclusion body tag or peptide of interest) was cross-linked:

1. A Cross-Linked Fusion Tag

The isolated supernatant containing the dissolved peptide of interest is pH adjusted as required to precipitate the peptide of interest. An organic solvent like acetone, ethanol or methanol may be used to induce precipitation of the target peptide or impurities. The mixture may be cooled to further increase precipitation. The product precipitate is then recovered by centrifugation or filtration. The precipitate may then be washed by chilled solvents or aqueous solvent mixtures. The product may be dried, re-suspended or dissolved as required for final use.

2. A Cross-Linked Peptide of Interest

The isolated insoluble precipitate (cross-linked peptide of interest) may be further processed into an appropriate product form. In one embodiment, the isolated precipitate is subjected to reducing conditions for a period of time whereby the intermolecular disulfide bonds are broken. A nitrogen purge and/or a reducing agent such as $Na_2SO_3$ may be used. Other chemical reducing agents selected from the group consisting of DTT (dithiothreitol), TCEP (Tris(2-carboxyethyl)phosphine), 2-mercaptoethanol and 2-mercaptoethylamine. Generally reducing agents include those that contain thiol groups, those that are phosphines and their derivatives as well as sulfites and thiosulfites may also be used. In a preferred embodiment, a nitrogen purge is used. The free peptide of interest may be subject to additional washing and/or precipitation steps in order to further purify the material prior to packaging and/or final use.

Applicants specifically incorporate the entire contents of all cited references in this disclosure. Further, when an amount, concentration, or other value or parameter is given either as a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

The meaning of abbreviations used is as follows: "min" means minute(s), "h" means hour(s), "µL" means microliter(s), "mL" means milliliter(s), "L" means liter(s), "nm" means nanometer(s), "mm" means millimeter(s), "cm" means centimeter(s), "µm" means micrometer(s), "mM" means millimolar, "M" means molar, "mmol" means millimole(s), "µmole" means micromole(s), "g" means gram(s), "µg" means microgram(s), "mg" means milligram(s), "g"

means the gravitation constant, "rpm" means revolutions per minute, "psi" means pounds per square inch, and "mPa" means megapascal(s).

General Methods

Standard recombinant DNA and molecular cloning techniques used herein are well known in the art and are described by Sambrook, J. and Russell, D., *Molecular Cloning: A Laboratory Manual*, Third Edition, Cold Spring Harbor Laboratory Press, Cold Spring Harbor, N.Y. (2001); and by Silhavy, T. J., Bennan, M. L. and Enquist, L. W., *Experiments with Gene Fusions*, Cold Spring Harbor Laboratory Cold Press Spring Harbor, N.Y. (1984); and by Ausubel, F. M. et. al., *Short Protocols in Molecular Biology*, 5$^{th}$ Ed. Current Protocols and John Wiley and Sons, Inc., N.Y., 2002.

Materials and methods suitable for the maintenance and growth of bacterial cultures are also well known in the art. Techniques suitable for use in the following Examples may be found in *Manual of Methods for General Bacteriology*, Phillipp Gerhardt, R. G. E. Murray, Ralph N. Costilow, Eugene W. Nester, Willis A. Wood, Noel R. Krieg and G. Briggs Phillips, eds., American Society for Microbiology, Washington, D.C., 1994, or by Thomas D. Brock in *Biotechnology: A Textbook of Industrial Microbiology*, Second Edition, Sinauer Associates, Inc., Sunderland, Mass., 1989. All reagents, restriction enzymes and materials used for the growth and maintenance of bacterial cells were obtained from Aldrich Chemicals (Milwaukee, Wis.), BD Diagnostic Systems (Sparks, Md.), Gibco BRL Life Technologies (Rockville, Md.), Invitrogen (Carlsbad, Calif.) or Sigma Aldrich Chemical Company (St. Louis, Mo.), DIFCO Labs (Detroit, Mich.), Promega (Madison, Wis.), QIAgen (Valencia, Calif.), or DNA 2.0 Inc. (Menlo Park, Calif.) unless otherwise specified.

Growth Conditions:

*E. coli* cells were fermented in a 10-L vessel unless otherwise noted. The fermentation proceeded in three stages:
1. Preparation of 125-mL of seed inoculum. Cells containing the construct of interest were inoculated in 125-mL of 2YT seed medium (10 g/L yeast extract, 16 g/L tryptone, 5 g/L NaCl and appropriate antibiotic) and grown for several hours at 37° C.
2. Growth in batch phase. The 125-mL of inoculum was added to 6 L of batch medium (9 g/L $KH_2PO_4$, 4 g/L $(NH_4)_2HPO_4$ 1.2 g/L $MgSO_4.7H_2O$, 1.7 g/L citric acid, 5 g/L yeast extract, 0.1 mL/L Biospumex 153K antifoam, 4.5 mg/L Thiamine.HCl, 23 g/L glucose, 10 mL/L trace elements, 50 mg/L uracil, appropriate antibiotic, pH 6.7) at 37° C.
3. Growth in fed batch phase. After about 12 hours of growth in the batch phase, the fed-batch phase was initiated. Fed-batch medium (2 g/L $MgSO_4.7H_2O$, 4 g/L $(NH_4)_2HPO_4$ 9 g/L $KH_2PO_4$, 1-2 g/min Glucose) was added at a constant rate to the reactor for about 15 hours at 37° C. 4 hours before the end of the fed-batch phase the cells were induced to express the POI by adding 2 g/L L-arabinose.

Method to Determine Inclusion Body Formation

To test for the presence of inclusion bodies in the cells, the cells were lysed with 50 mg of CELLYTIC™ Express (a mixture of non-denaturing detergents and enzymes available from Sigma, St. Louis, USA) per mL of growth. The inclusion bodies remain insoluble and are spun out with a micro-centrifuge. For large scale isolation after homogenization, a stacked-disk centrifugation process was used to isolate the insoluble inclusion bodies.

Example 1

Construction of Expression Plasmids

Figure 2:
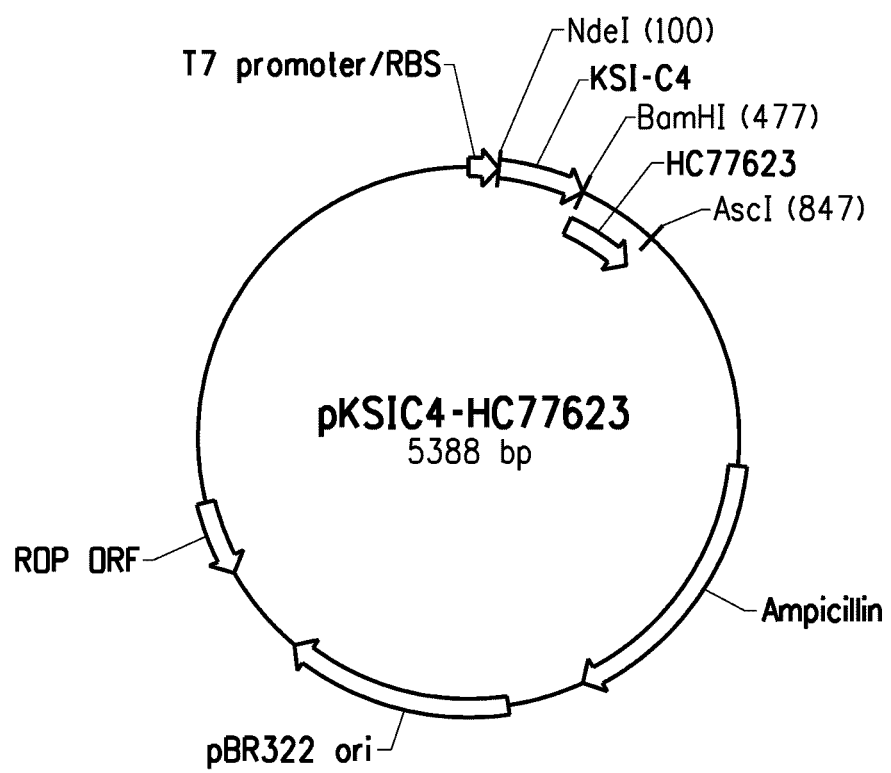
FIG. 2 is a diagram of expression plasmid pKSIC4-HC7723.
Figure 3:
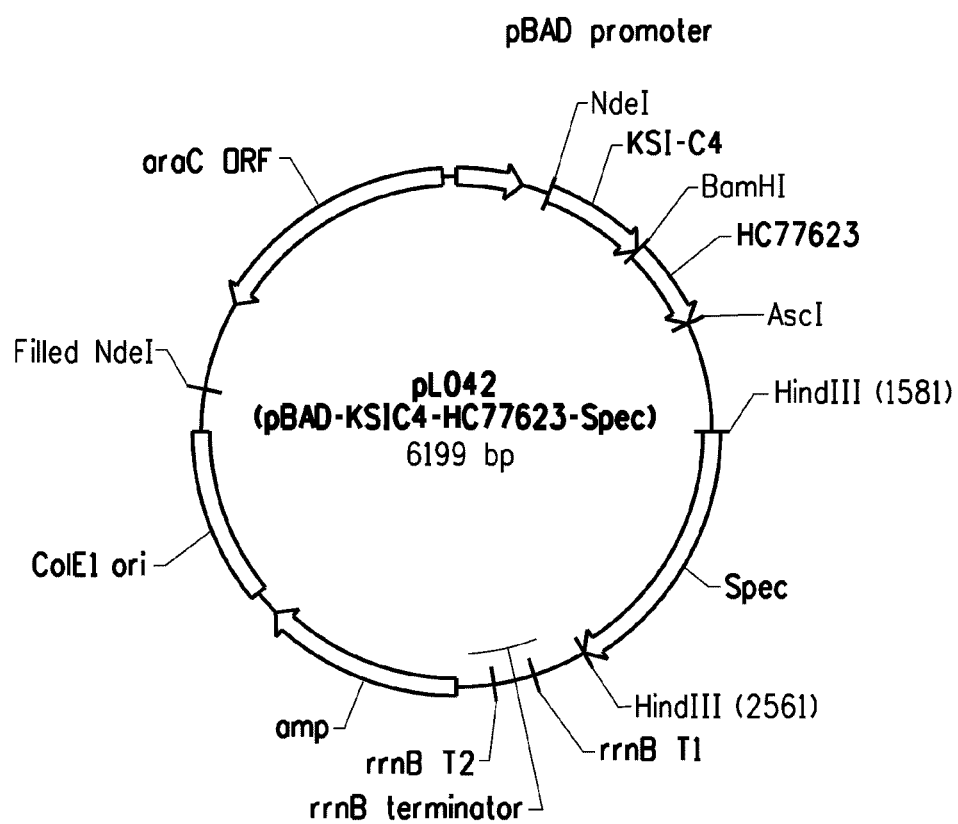
FIG. 3 is a diagram of expression plasmid pLR042.
Figure 4:
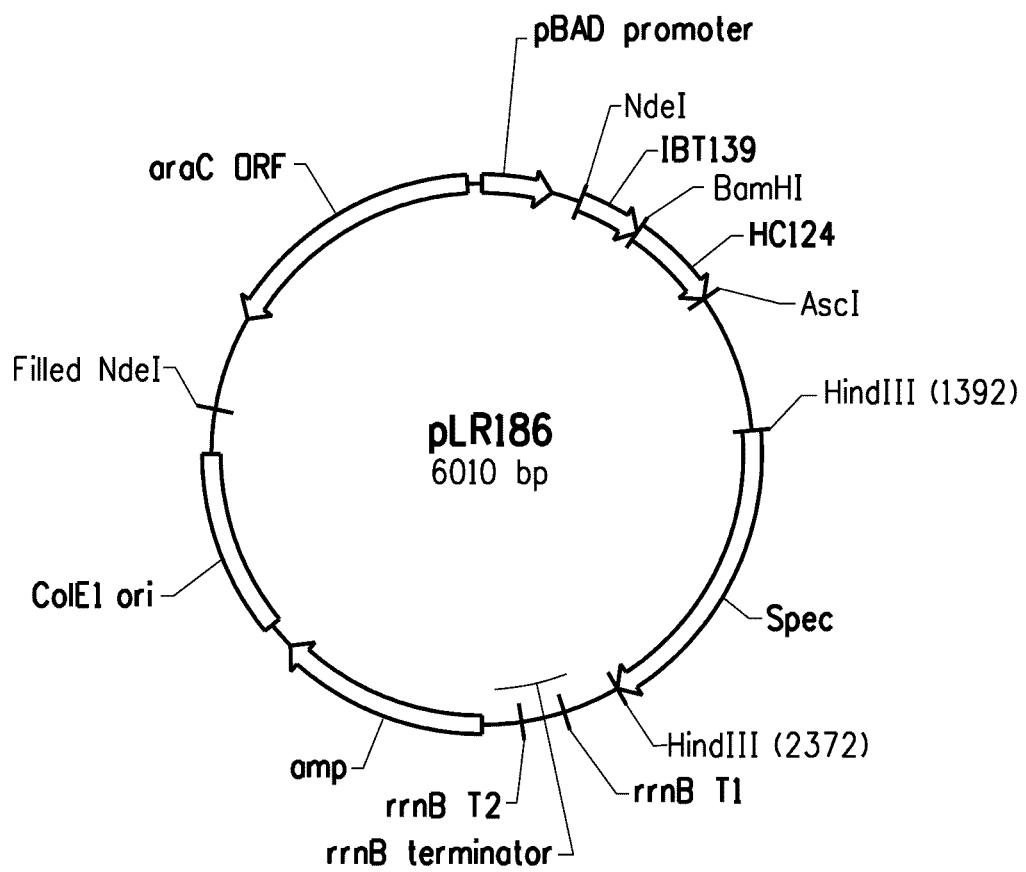
FIG. 4 is a diagram of expression plasmid pLR186.

Several expression systems were used to produce the fusion proteins in an *E. coli* host cell. One expression system was based on *E. coli* strain BL21-AI (Invitrogen) in combination with a T7-based expression vector (pLX121; SEQ ID NO: 1; FIG. 1, and pKSIC4-HC7723; FIG. 2; SEQ ID NO: 2) wherein expression of the T7 RNA polymerase is controlled by the araBAD promoter. The other expression system was based on *E. coli* MG1655 (ATCC 46076™) derived strain in combination with a pBAD-based expression vector (pLR042; FIG. 3; SEQ ID NO: 3, and pLR186; FIG. 4; SEQ ID NO: 4) wherein the endogenous chromosomal copy of the araBAD operon was deleted (the modified *E. coli* MG1655 strain comprising a disruption in the endogenous araBAD operon is referred to herein as *E. coli* strain KK2000). The 3' region downstream and operably linked to the respective promoter in each of the vectors was designed to facilitate simple swapping of the DNA encoding the respective inclusion body tag and/or the peptide of interest. NdeI and BamHI restriction sites flanked the region encoding the inclusion body tag (IBT). BamHI and AscI restriction sites flanked the region encoding the peptide of interest (POI).

The nucleic acid molecules encoding the various fusion peptides were designed to include at least one region encoding an inclusion body tag (IBT) linked to a peptide of interest (POI). As described above, the nucleic acid molecules encoding the components of the fusion peptide were designed to include the appropriate NdeI/BamHI (region encoding the inclusion body tag) and BamHI/AscI restriction sites (region encoding the peptide of interest) to facilitate insertion in the expression vector. Insertion of the nucleic acid molecules created a chimeric gene encoding a fusion peptide operably linked to the respective promoter. The fusion peptide was designed to have an inclusion body tag (IBT) linked to a peptide of interest (POI) where the two components were separated by a cleavable peptide linker (CS; for example, an acid cleavable DP moiety):

Construction of pLX121 Expression Plasmid (T7-Based Expression):

A genetic construct was prepared for evaluating the performance of the cross-linkable inclusion body tags when fused to a soluble peptide of interest. A plasmid (pLX121; FIG. 1; SEQ ID NO: 1) containing a pBR322 origin of replication and the bla gene to confer ampicillin resistance was used. Expression of the chimeric gene was driven by a T7 promoter. Construction of this plasmid is previously described in co-pending U.S. patent application Ser. No. 11/516,362, herein incorporated by reference.

Briefly, the pLX121 expression vector was designed from the destination plasmid pDEST17 (Invitrogen. Carlsbad, Calif.). The expression vector was modified so that the chimeric gene encoding the fusion protein was expressed under the control of the T7 promoter. NdeI and BamHI restriction sites were used for easy swapping of the various inclusion body tags. BamHI and AscI restriction sites were used to facilitate swapping of various peptides of interest. The sequence encoding the junction between the inclusion body tag and the peptide of interest was designed to encode an acid cleavable D-P moiety.

Construction of Expression Vector pKSIC4-HC77623

The vector pKSIC4-HC77623 (SEQ ID NO: 2; FIG. 2) was also derived from the commercially available vector pDEST17 (Invitrogen). Construction of this vector has been previously described in co-pending U.S. patent application Ser. No. 11/389,948, herein incorporated by reference. It includes sequences derived from the commercially available vector pET31b (Novagen, Madison, Wis.) that encode a fragment of the enzyme ketosteroid isomerase (KSI; Kuliopulos, A. and Walsh, C. T., *J. Am. Chem. Soc.* 116:4599-4607 (1994)). The KSI fragment used as an inclusion body tag to promote partition of the peptides into insoluble inclusion bodies in *E. coli*. The nucleic acid molecule encoding the KSI sequence from pET31 b was modified using standard mutagenesis procedures (QuickChange II, Stratagene, La Jolla, Calif.) to include three additional cysteine codons, in addition to the one cysteine codon found in the wild type KSI sequence, resulting in the inclusion body tag KSI4C (SEQ ID NOs: 5 and 6). The plasmid pKSIC4-HC77623 was constructed using standard recombinant DNA methods well known to those skilled in the art. The BamHI and AscI restriction sites facilitated swapping of nucleic acid molecules encoding the various peptides of interest. The inserts were designed to encode an acid cleavable DP moiety useful in separating the inclusion body tag from the peptide of interest.

Construction of pLR042 Expression Plasmid (pBAD Based Expression)

Plasmid pLR042 (SEQ ID NO: 3; FIG. 3) contains a ColE1 type origin of replication, the bla gene to confer ampicillin resistance and the aadA-1 gene to confer spectinomycin (Spec) resistance. The tag/peptide fusion construct is driven by the pBAD promoter. The plasmid also encodes the gene for the araC regulator.

Plasmid pLR042 was derived from the commercially available plasmid pBAD-HisA (Invitrogen). Briefly, a modified multiple cloning site (MCS) was cloned in pBAD-HisA and the NdeI restriction site at position 2844 was removed to create a single NdeI site downstream of the pBAD promoter. The resulting plasmid was named pBAD-HisA_MCSmod. The NdeI/EcoRI fragment of plasmid pKSIC4-HC 77623 was inserted into the NdeI/EcoRI site of pBAD-HisA_MCSmod, creating plasmid pSF004_pBAD-KSIC4-HC77623. The HindIII fragment of plasmid pCL1920 (Lerner and Inouye, *Nucleic Acids Research*, 18:4631 (1990); GENBANK® Accession No. AB236930) comprising the spectinomycin resistance gene (aadA-1) was inserted into pSF004_pBAD-KSI4-HC77623, creating plasmid pLR042 (FIG. 4; SEQ ID NO: 3).

Construction of pLR186 Expression Plasmid:

Plasmid pLR186 (FIG. 4; SEQ ID NO: 4) was created from plasmid pLR042 (SEQ ID NO: 3; FIG. 3) by removing the coding region for the KSIC4-HC77623 fusion peptide and inserting the coding region for fusion peptide IBT139-HC776124 (i.e. a fusion peptide comprising inclusion body tag IBT-139 linked to the HC776124 peptide of interest; see Example 5).

Example 2

KSI Inclusion Body Tag without an Effective Number of Cross-Linkable Cysteines Cannot be Easily Separated from the Cleaved Peptide by Simple Physical Methods The purpose of this example is to show that separation of the inclusion body tag and peptide is more difficult if the tag is not selectively cross-linked via cysteines and subsequently precipitated. In this example the peptide and IB-tag were separated using preparative HPLC.

Construct: KSI.HC77607 (SEQ ID NOs: 7 and 8; Table 2). Peptide HC77607 does have cysteine residues, however, in this example it was not used as a separation tool (Table 2). Peptide HC77607 (i.e. the peptide of interest) is comprised of several hair binding domains (bold) including KF11 (SEQ ID NO: 9) and D21' (RTNAADHP; SEQ ID NO: 10). The acid cleavable DP moiety is italicized.

TABLE 2

Components of hair binding peptide HC77607

| Peptide Name | Formula | Amino acid Sequence | Nucleic acid SEQ ID NO: | Amino Acid SEQ ID NO: |
|---|---|---|---|---|
| HC77607 | GSDP-KF11-GGG-D21'-KCGGG-KF11-GGG-D21'-KCGGG-KF11-GGG-D21'-KC | GSD*DP*NTSQLSTGGG RTNAADHPKCGGGN TSQLSTGGGRTNAA DHPKCGGGNTSQLS TGGGRTNAADHPKC | 11 | 12 |

Cloning of KSI-HC77607: The genes for KSI and HC77607 were synthesized by DNA2.0 (Menlo Park, Calif.) with appropriate restriction sites and cloned into pLX121 as described above.

Growth Conditions: Growth and expression of the chimeric gene encoding the fusion peptide was conducted as described above.

Isolation of Fusion Protein and HPLC Analysis:

The whole fermentation broth was passed through an APV model 2000 Gaulin type homogenizer at 12,000 psi (82,700 kPa) for three passes. The broth was cooled to below 5° C. prior to each homogenization. The homogenized broth was immediately processed through a Westfalia WHISPERFUGE™ (Westfalia Separator Inc., Northvale, N.J.) stacked disc centrifuge at 600 mL/min and 12,000 relative centrifugal force (RCF) to separate inclusion bodies from suspended cell debris and dissolved impurities. The recovered paste was re-suspended at 15 g/L (dry basis) in water and the pH adjusted to about 10.0 using NaOH. The suspension was passed through the APV 2000 Gaulin type homogenizer at 12,000 psi (82,700 kPa) for a single pass to provide rigorous mixing. The homogenized pH 10 suspension was immediately processed in a Westfalia WHISPERFUGE™ stacked disc centrifuge at 600 mL/min and 12,000 RCF to separate the washed Inclusion bodies from suspended cell debris and dissolved impurities. The recovered paste was resuspended at 15 gm/L (dry basis) in pure water. The suspension was passed through the APV 2000 Gaulin type homogenizer at 12,000 psi (82,700 kPa) for a single pass to provide rigorous washing. The homogenized suspension was immediately processed in a Westfalia WHISPERFUGE™ stacked disc centrifuge at 600 mL/min and 12,000 RCF to separate the washed Inclusion bodies from residual suspended cell debris and NaOH. The recovered paste was resuspended in pure water at 25 gm/L (dry basis) and the pH or the mixture adjusted to 2.2 using HCl. Dithiothreitol (DTT) was added to 10 mM (when processing the HC77607 peptide). The acidified suspension was heated to 70° C. for 14 hours to complete cleavage of the DP site separating the fusion peptide from the product peptide. The product was pH neutralized (note: the pH used may vary depending upon the solubility of the peptide being recovered) and cooled to ~5° C. and held for 12 hours. During this step the suspension was held in a 500-mL or 1-L bottle no more than ¾ full to ensure adequate presence of oxygen to ensure cysteine cross linking through disulfide formation. The mixture was then centrifuged at 9000 RCF for 30 minutes and the supernatant decanted for HPLC analysis.

HPLC Method

The supernatant was filtered with a 0.2 micron membrane. The filtered product was loaded in a 22×250 mm reverse phase chromatography column GRACEVYDAC® (218TP1022) containing 10 micron C18 media which was preconditioned with 10% acetonitrile (ACN), 90% water with 0.1% v/v trifluoroacetic acid (TFA). The product was recovered in a purified state by eluting the column with a gradient of water and acetonitrile (ACN) ramping from 10% to 25% acetonitrile (ACN) in water with TFA at 0.1% v/v at room temperature and approximately 10 mL/min. Spectrophotometric detection at 220 nm was used to monitor and track elution of the product peptide.

Result:

The solubility tag and peptide were separated using the preparative HPLC method described in above. The IBTs and POIs were both found in the supernatant.

Example 3

An Inclusion Body Tag KSI(C4) with an Effective Number of Cross-Linkable Cysteines is Easily Separated from a Cleaved Peptide Mixture by Precipitation The purpose of this example is to show that separation of the IBT and peptide of interest can by achieved by oxidatively cross-linking the cysteine residues within the IBT and subsequent precipitation of the tag. The peptide of interest was HC77643 (contains no cysteine residues). The remaining soluble peptide was shown to be free of the KSI(C4) tag by using HPLC.

Construct: KSI(C4).HC77643 (SEQ ID NOs: 13 and 14)

The design of peptide HC77643 is provided in Table 3 Peptide HC77643 is comprised of several hair binding domains including A09 (SEQ ID NO: 15) and KF11 (SEQ ID NO: 9) (bold). The acid cleavable DP moiety is italicized.

Cloning of KSI(C4).HC77643: The genes for KSI(C4) (SEQ ID NO: 5) and HC77643 (SEQ ID NO:16) were synthesized by DNA2.0 (Menlo Park, Calif.) with appropriate restriction sites and cloned into pLX121 as mentioned above.

Production of Product Protein:

Growth and expression of the chimeric gene were conducted as described above. The protein was purified as described in above. After the acid cleavage and pH neutralization, the mixture was stored at approximately 5° C. for about 6 hours to allow the cysteines to form cross-linked bonds. Oxygen to drive the cysteine cross-linking was provided by a 30% bottle air volume. The mixture was centrifuged at 9000 RCF for 30 minutes and the precipitated tag was separated from the soluble peptide.

Results:

SDS-PAGE gel analysis of both the precipitated paste (comprised of cross-linked IBTs) and the remaining soluble fraction showed the presence of KSI(C4) in the insoluble paste, and HC77643 remaining in the soluble fraction. This was further confirmed by HPLC (using the HPLC method described in Example 2), which showed only the presence of HC77643 in the soluble fraction. The results of the cross-linking experiments are summarized in Table 5.

Example 4

Small Inclusion Body Tag (IBT139) without Cysteines

The large KSI tag used in the previous examples is effective in inducing inclusion body formation. However, the use of a smaller IBT increases the relative yield of the peptide of interest when prepared as a fusion peptide. The purpose of this example is to show that a small inclusion body tag (for example, a small inclusion body tag herein referred to as IBT139; SEQ ID NO: 18) can drive the fusion peptides into inclusion bodies.

Construct: IBT139.HC776124 (pLR186) (SEQ ID NOs: 19 and 20). The design of peptide HC776124 is provided in Table 4. Peptide HC776124 (a dimer of HC77643) is comprised of several hair binding domains including A09 (SEQ ID NO: 15) and KF11 (SEQ ID NO: 9) (bold). The acid cleavable DP moieties are italicized (Table 4).

TABLE 3

Components of Multi-block Hair-binding Peptide HC77643

| Peptide Name | Formula | Amino acid Sequence | Nucleic acid SEQ ID NO: | Amino Acid SEQ ID NO: |
|---|---|---|---|---|
| HC77643 | DPG-A09-GAG-A09-GGSGPGSGG-KF11-GGG-KF11-GGPKK | *DP*GIPWWNIRAPLNA GAGIPWWNIRAPLNA GGSGPGSGGNTSQL STGGGNTSQLSTGG PKK | 16 | 17 |

TABLE 4

| Peptide Name | Formula | Amino acid Sequence | Nucleic Acid SEQ ID NO: | Amino Acid SEQ ID NO: |
|---|---|---|---|---|
| HC776124 | D(PG-A09-GAG-A09-GGSGPGSGG-KF11-GGG-KF11-GGPKKPGD)2 | D*PG*IPWWNIRAPLNAGAGIP WWNIRAPLNAGGSGPGSGG NTSQLSTGGGNTSQLSTGGP KKPGD*PG*IPWWNIRAPLNAG AGIPWWNIRAPLNAGGSGPG SGGNTSQLSTGGGNTSQLST GGPKKPGD | 21 | 22 |

Cloning and Initial Analysis of IBT139.HC776124:

A 56 amino acid tag IBT139 (SEQ ID NO: 18), was identified as being effective in driving the fusion peptides into inclusion bodies. HC776124 (i.e. the POI) was synthesized by DNA2.0 (Menlo Park, Calif.) and cloned into restriction sites BamHI (5') and AscI (3') of plasmid pLR042 (see Example 1). The resulting plasmid was designated as pLR186 (FIG. 2; SEQ ID NO: 4).

The pLR186 construct was transformed into *E. coli* MG1655 (ATCC 46076™) with the endogenous chromosomal araBAD operon deleted. A 3-mL growth in LB (plus 100 µg/mL of ampicillin) was inoculated with 30 µL of an overnight culture. The culture was grown to $OD_{600}$ of about 0.4 and induced with 0.2% arabinose and grown for 3 hours. To determine soluble versus insoluble cell content, the cells were lysed and soluble and insoluble fractions were run on an SDS-PAGE gel. The fusion protein produced was made in the form of insoluble inclusion bodies.

Production of Product Protein:

The fusion protein was produced and processed as described above.

Results:

IBT139 was effective in promoting inclusion body formation.

Example 5

Small Inclusion Body Tag (IBT186) Comprising an Effective Amount of Cross-Linkable Cysteines can be Separated from the Cleaved Peptide Mixture by Oxidative Cross-Linking and Precipitation The purpose of this example is to show that a small tag inclusion body tag (e.g. IBT186; SEQ ID NOs: 23 and 24) containing an effective number of cross-linkable cysteine residues (IBT186 contains 4 cysteine residues) can drive both inclusion body formation while being easy to separate using oxidative cross-linking. The example also shows that a small inclusion body tag previous shown to be effective in inducing inclusion body formation can be modified to contain an effective amount of cross-linkable cysteine residues (IBT186 is derived from small tag IBT139 (Example 4) with four cysteines distributed within its sequence) while maintaining its ability to effectively drive inclusion body formation. The presence of four cysteines allows simple precipitation of the tag after cleavage of tag and peptide.

Construct: IBT186-HC776124 (pLR238) (SEQ ID NOs: 25 and 26)

Cloning and Initial Analysis of IBT186.HC776124:

The coding sequence (SEQ ID NO: 23) encoding IBT186 was synthesized by DNA2.0 (Menlo Park, Calif.) and cloned into restriction sites NdeI (5') and BamHI (3') of plasmid pLR186 (expression driven off pBAD promoter) to make a fusion with the HC776124 construct, creating plasmid pLR238. The plasmid was transformed into *E. coli* MG1655 (ATCC 46076™) with the araBAD operon deleted.

A 3-mL growth in LB (plus 100 µg/mL of ampicillin) was inoculated with 30 µL of an overnight culture. The culture was grown to $OD_{600}$ of about 0.4 and induced with 0.2% arabinose and grown for 3 hours. To determine soluble versus insoluble cell content, the cells were lysed and soluble and insoluble fractions were run on an SDS-PAGE gel. The fusion protein produced was again made as insoluble inclusion bodies.

Production of Product Protein:

The protein was produced and processed as described above. After the acid cleavage and pH neutralization, the mixture was stored at ~5° C. for about 6 hours to allow the cysteines to form cross-linked bonds. Ambient air exposure provided oxygen to cause cysteine cross-linking. The mixture was centrifuged at 9000 RCF for 30 minutes and the precipitated inclusion body tag was separated from the soluble peptide of interest.

Results:

SDS-PAGE gel analysis of both the precipitate paste and the remaining soluble fraction showed the presence of IBT186 in the insoluble paste and HC776124 remaining in the soluble fraction. This was further confirmed by HPLC (see method described in Example 2), which showed only the presence of HC776124 in the soluble fraction. The results of the cross-linking experiments are summarized in Table 5.

Example 6

Small Inclusion Body Tag IBT139(5C) Comprising an Effective Amount of Cross-Linkable Cysteines can be Separated from the Cleaved Peptide Mixture by Oxidative Cross-Linking and Precipitation The purpose of this example is to show that another small tag inclusion body tag (e.g. IBT139(5C); SEQ ID NOs: 181-192) containing an effective number of cross-linkable cysteine residues (IBT139(5C) contains 5 cysteine residues) can drive both inclusion body formation while being easy to separate using oxidative cross-linking. The example also shows that a small inclusion body tag previous shown to be effective in inducing inclusion body formation can be modified to contain an effective amount of cross-linkable cysteine residues (IBT139(5C) is derived from small tag IBT139 (Example 4) with five cysteines distributed within its sequence) while maintaining its ability to effectively drive inclusion body formation. The presence of five cysteines allows simple precipitation of the tag after cleavage of tag and peptide of interest.

Construct: IBT139(5C)-HC776124 (pLR435) (SEQ ID NOs: 183-184)

Cloning and Initial Analysis of IBT139(5C).HC776124:

The coding sequence (SEQ ID NO: 181) encoding IBT139 (5C) (SEQ ID NO: 182) was synthesized by DNA2.0 (Menlo Park, Calif.) and cloned into restriction sites NdeI (5') and BamHI (3') of plasmid pLR186 (expression driven off pBAD promoter) to make a fusion with the HC776124 (SEQ ID NO: 22) construct, creating plasmid pLR435 (SEQ ID NO: 180). The plasmid was transformed into *E. coli* MG1655 (ATCC 46076™) with the native araBAD operon deleted. The sequence of IBT139(5C) comprising the 5 cysteine residues (bold) is provided below.

```
IBT139(5C):
                                    (SEQ ID NO: 182)
MASCGQQRFQWQFEQQPRCGQQRFQWQFEQQPRCGQQRFQWQ

FEQQPECGQQRFQWQFEQQPC.
```

A 3-mL growth in LB (plus 100 µg/mL of ampicillin) was inoculated with 30 µL of an overnight culture. The culture was grown to $OD_{600}$ of about 0.4 and induced with 0.2% arabinose and grown for 3 hours. To determine soluble versus insoluble cell content, the cells were lysed and soluble and insoluble fractions were run on an SDS-PAGE gel. The fusion protein produced was again made as insoluble inclusion bodies.

Production of Product Protein:

The protein was produced and processed as described above. After the acid cleavage and pH neutralization, the mixture was stored at ~5° C. for about 6 hours to allow the cysteine residues to oxidize and form cross-linked bonds. Ambient air exposure provided sufficient oxygen to cause cysteine cross-linking. The mixture was subsequently centrifuged at 9000 RCF for 30 minutes and the precipitated inclusion body tag was separated from the soluble peptide of interest.

Results:

SDS-PAGE gel analysis of both the precipitate paste and the remaining soluble fraction showed the presence of IBT139(5C) in the insoluble paste and HC776124 remaining in the soluble fraction. This was further confirmed by HPLC (see method described in Example 2), which showed only the presence of HC776124 in the soluble fraction. The results of the cross-linking experiments are summarized in Table 5.

Example 7

Introduction of Multiple Cysteines to the Terminus of an Inclusion Body Tag Promotes Oxidative Cross-Linking while Retaining the Ability to Effectively Drive Fusion Peptides into Inclusion Bodies The purpose of this example is to show that the addition of a cross-linkable cysteine motif comprising effective number of cysteine residues to the terminus of an inclusion body tag creates a cross-linkable IBT, even when the cysteines are spaced closely together. A cross-linkable cysteine motif was added to an inclusion body tag normally devoid of cross-linkable cysteine residues (i.e. IBT139; SEQ ID NO: 18), creating cysteine modified tag "IBT139.CCPGCC" (SEQ ID NO: 27). The addition of the motif did not alter the IBT's ability to drive inclusion body formation while the modification facilitated simple separation of the tag using oxidative cross-linking. The results of the cross-linking experiments are summarized in Table 5.

Construct: IBT139.CCPGCC. HC776124 (SEQ ID NOs: 28 and 29).

Cloning and Initial Analysis:

To facilitate crosslinking, the tetracysteine tag CCPGCC (SEQ ID NO: 31) was introduced at the end of the inclusion body promoting sequence IBT139 (SEQ ID NO: 18) which does not naturally contain cysteine residues. The CCPGCC tetracysteine tag is the LUMIO™ biarsenical dye binding motif. The LUMIO™ Green detection kit was obtained from Invitrogen (Invitrogen, Carlsbad, Calif.)

The oligonucleotides encoding the tetracysteine tag CCPGCC (SEQ ID NO:30) were synthesized by Sigma Genosys. The top strand oligo 5'-GATCTTGCTGTC-CGGGCTGTTGCG-3' (SEQ ID NO: 32) and the bottom strand oligo 5'-GATCCGCAACAGCCCGGACAGCAA-3' (SEQ ID NO: 33) were annealed with a BglII overhang at the 5' end and a BamHI overhang at the 3' end. The annealed double stranded fragment was cloned into the BamHI site of a peptide expression plasmid pLR186, creating plasmid pLR199. Plasmid pLR199 contained the peptide of interest HC776124 fused to the inclusion body promoting sequence IBT139 expressed by the $P_{BAD}$ promoter. The resulting clone contained the tetracysteine tag CCPGCC (SEQ ID NO: 31) inserted after the inclusion body promoting sequence and before the acid cleavage site. It was shown that the introduction of the tetracysteine moiety did not affect expression or localization of the peptides by running an equivalent number of cells on a protein gel and seeing same levels of expression. The overexpressed protein was shown to be in the form of inclusion bodies by treating the cells with CELLYTIC™ Express and verifying that they were in the insoluble fraction. The inclusion body tag promoting sequence IBT139 with addition of the cross-linkable CCPGCC tag did not alter the inclusiobn body tag's ability to form inclusion bodies (Table 5).

Production of Product Protein:

The protein was produced and processed as described above. After the acid cleavage and pH neutralization, the mixture was stored at ~5° C. for at least 6 hours to allow the cysteines to form cross-linked bonds. Ambient air exposure provided oxygen to cause cysteine cross-linking. The mixture was centrifuged at 9000 RCF for 30 minutes and the precipitated tag was separated from the soluble peptide.

Results:

SDS-PAGE gel analysis of both the precipitated paste and the remaining soluble fraction showed the presence of the inclusion body tag (IBT139.CCPGCC) in the insoluble paste and the peptide of interest (HC776124) remaining in the soluble fraction. This was further confirmed by HPLC analysis (see Example 2), which showed only the presence of HC776124 in the soluble fraction. The results of the cross-linking experiments are summarized in Table 5.

TABLE 5

Summary of Cross-Linking Results

| Construct Evaluated | IBT Induces IB Formation in Cell | Number of Cysteines in the inclusion body tag | Separation via Oxidative Cross-linking and Centrifugation |
|---|---|---|---|
| KSI.HC77607 | Yes | None | No |
| KSI(C4).HC77643 | Yes | 4 | Yes |
| IBT139.HC776124 | Yes | None | No |
| IBT186.HC776124 | Yes | 4 | Yes |
| IBT139.CCPGCC.HC776124 | Yes | 4 | Yes |
| IBT139(5C).HC776124 | Yes | 5 | Yes |

What is claimed is:

1. A process to obtain a peptide of interest from a fusion peptide comprising:
   a) providing a population of fusion peptides comprising the general structure:

IBT-CS-POI or

POI-CS-IBT wherein;
   i) IBT is an inclusion body tag that does not include a cysteine residue;
   ii) CS is a cleavage site; and
   iii) POI is a peptide of interest comprising an effective number of cysteine residues;
   b) cleaving the population of fusion peptides at said cleavage site whereby the inclusion body tag is no longer linked to the peptide of interest and whereby a mixture of peptide molecules is produced comprising a plurality of inclusion body tags and a plurality of peptides of interest;
   c) subjecting the mixture of peptide molecules of step (b) to oxidizing conditions whereby the peptides of interest are cross-linked; and
   d) recovering the peptide of interest.

2. A process according to claim 1 wherein the population of fusion peptides is produced in a recombinant host cell comprising a nucleic acid molecule encoding said fusion peptides.

3. The process of claim 1 wherein the effective number of cysteine residues in the peptide of interest is at least 3.

4. The process of claim 1 or 3 wherein the population of fusion peptides is cleaved by a cleavage reagent selected from the group consisting of chemical cleavage reagents and enzymatic cleavage reagents.

5. The process of claim 4 wherein the chemical cleavage reagent is an effective amount of an acid cleavage reagent.

6. The process of claim 1 wherein inclusion body tag is less than 125 amino acids in length.

7. The process of claim 1 wherein the peptide of interest is less than 300 amino acids in length.

8. The process of claim 7 wherein the peptide of interest is selected from the group consisting of body surface-binding peptides, hair-binding peptides, skin-binding peptides, nail-binding peptides, teeth-binding peptides, cellulose-binding peptides, polymer-binding peptides, clay-binding peptides, pigment-binding peptides, and antimicrobial peptides.

9. The process of claim 2 wherein the recombinant host cell is a microbial host cell.

10. The process of claim 9 wherein the microbial host cell is selected from the group consisting of bacteria, fungi, and yeast.

11. The process of claim 10 wherein the microbial host cell is selected from the group consisting of *Aspergillus, Trichoderma, Saccharomyces, Pichia, Yarrowia, Candida, Hansenula, Salmonella, Bacillus, Acinetobacter, Zymomonas, Agrobacterium, Erythrobacter, Chlorobium, Chromatium, Flavobacterium, Cytophaga, Rhodobacter, Rhodococcus, Streptomyces, Brevibacterium, Corynebacteria, Mycobacterium, Deinococcus, Escherichia, Erwinia, Pantoea, Pseudomonas, Sphingomonas, Methylomonas, Methylobacter, Methylococcus, Methylosinus, Methylomicrobium, Methylocystis, Alcaligenes, Synechocystis, Synechococcus, Anabaena, Thiobacillus, Methanobacterium, Klebsiella*, and *Myxococcus*.

12. The process of claim 1 wherein the oxidizing conditions comprises the presence of a gas comprising an effective amount of diatomic or triatomic oxygen.

* * * * *